US012152174B2

(12) United States Patent
Messersmith et al.

(10) Patent No.: US 12,152,174 B2
(45) Date of Patent: Nov. 26, 2024

(54) ADJUSTABLY STABLE ADHESIVE COMPOSITIONS FOR MEDICAL AND NON-MEDICAL USES, AND RECYCLING

(71) Applicant: THE REGENTS OF THE UNIVERSITY OF CALIFORNIA, Oakland, CA (US)

(72) Inventors: Phillip B. Messersmith, Berkeley, CA (US); Subhajit Pal, Berkeley, CA (US); Kelsey G. Defrates, San Francisco, CA (US); Jisoo Shin, Mountain View, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

(21) Appl. No.: 18/635,583

(22) Filed: Apr. 15, 2024

(65) Prior Publication Data
US 2024/0352295 A1    Oct. 24, 2024

Related U.S. Application Data

(60) Provisional application No. 63/626,358, filed on Jan. 29, 2024, provisional application No. 63/502,429, (Continued)

(51) Int. Cl.
*C09J 181/04*    (2006.01)
*A61L 24/04*    (2006.01)
(Continued)

(52) U.S. Cl.
CPC .......... *C09J 181/04* (2013.01); *A61L 24/046* (2013.01); *C08G 75/14* (2013.01); *C08G 75/26* (2013.01)

(58) Field of Classification Search
None
See application file for complete search history.

(56) References Cited

U.S. PATENT DOCUMENTS 6,013,663 A * 1/2000 Fujita .................. A61P 25/16
    544/379
6,090,842 A * 7/2000 Packer ................ A61P 43/00
    549/39
(Continued)

FOREIGN PATENT DOCUMENTS

WO    PCT/US24/24635    4/2024

OTHER PUBLICATIONS

U.S. Appl. No. 63/459,157, Messersmith et al., Apr. 13, 2023.
(Continued)

*Primary Examiner* — Peter A Salamon
(74) *Attorney, Agent, or Firm* — Brian S. Boyer; SYNDICATED LAW, PC

(57) ABSTRACT

Adhesive compositions for medical and non-medical uses are provided. The adhesive compositions can include cyclic disulfide monomers, oligomers of reactions between the cyclic disulfides, polymers of the cyclic disulfides, solid articles formed formed from the polymers, and any combination thereof. Methods of making, using, and recycling the adhesive compositions are provided, including use of the adhesive compositions on a variety of substrates that include biological tissue; biomaterials, including synthetics and natural such as bone, wood, and cellulosics; metals and alloys; polymers, plastics, and rubbers; ceramics; composites; and, any combination of these materials. The adhesives can adhere to substrates in a variety of environmental conditions that include ambient atmospheric conditions, wet conditions that include adhering materials underwater, and in a wide variety of temperatures and pressures, such as those temperatures and pressures found in medical environ-
(Continued)

ments, including in living tissue, as well as many residential, commercial, industrial, and manufacturing environments.

22 Claims, 25 Drawing Sheets

Related U.S. Application Data filed on May 16, 2023, provisional application No. 63/459,157, filed on Apr. 13, 2023.

(51) Int. Cl.
  *C08G 75/14* (2006.01)
  *C08G 75/26* (2006.01)

(56) References Cited

U.S. PATENT DOCUMENTS

| | | | | |
|---|---|---|---|---|
| 6,127,394 | A * | 10/2000 | Pershadsingh | C07D 417/12 514/369 |
| 6,150,358 | A * | 11/2000 | Goldstein | A61P 39/06 514/231.5 |
| 6,204,288 | B1 * | 3/2001 | Pershadsingh | C07C 323/12 549/39 |
| 6,288,106 | B1 * | 9/2001 | Pearson | C07D 307/62 549/39 |
| 6,369,098 | B1 * | 4/2002 | Pershadsingh | A61K 31/426 549/39 |
| 6,387,945 | B2 * | 5/2002 | Packer | C07D 339/02 549/39 |
| 6,605,637 | B1 * | 8/2003 | Harnett | A61P 37/06 544/242 |
| 6,900,338 | B1 * | 5/2005 | Haj-Yehia | A61P 43/00 549/39 |
| 6,936,715 | B2 * | 8/2005 | Harnett | A61P 1/08 544/379 |
| 8,211,956 | B2 | 7/2012 | Bock et al. | |
| 8,318,795 | B2 * | 11/2012 | Yu | A61P 35/00 549/38 |
| 8,318,954 | B2 | 11/2012 | Singh et al. | |
| 8,349,355 | B2 | 1/2013 | Soranzo et al. | |
| 8,535,647 | B2 | 9/2013 | Lucet-Levannier et al. | |
| 8,759,482 | B2 | 6/2014 | Ting et al. | |
| 8,921,445 | B2 | 12/2014 | Turshani et al. | |
| 9,186,431 | B2 | 11/2015 | Zimnitsky et al. | |
| 9,974,753 | B2 | 5/2018 | Salman et al. | |
| 9,999,702 | B2 | 6/2018 | Zimnitsky et al. | |
| 10,080,763 | B2 | 9/2018 | Bhalani et al. | |
| 10,786,595 | B2 | 9/2020 | Zimnitsky et al. | |
| 11,090,409 | B2 | 8/2021 | Zimnitsky et al. | |
| 11,510,926 | B2 | 11/2022 | Coderre et al. | |
| 11,684,618 | B2 | 6/2023 | Brosso et al. | |
| 2014/0316006 | A1 * | 10/2014 | Greaves | C07C 323/60 562/556 |
| 2015/0139933 | A1 * | 5/2015 | Puskas | A61K 31/795 424/78.06 |
| 2022/0096467 | A1 | 3/2022 | Kandula | |
| 2022/0354808 | A1 | 7/2022 | Pan-Montojo | |
| 2023/0277520 | A1 | 9/2023 | Brosso et al. | |

OTHER PUBLICATIONS

U.S. Appl. No. 63/502,429, filed May 16, 2023, Messersmith, et al.
U.S. Appl. No. 63/626,358, filed Jan. 29, 2024, Messersmith, et al.
Adhesives and Sealants Industry (2016) https://www.adhesivesmag.com/articles/94543-construction-growth-driving-adhesive-and-sealant-demand.
Albanese, K.R., et al. Building Tunable Degradtion into High-Performance Poly(acrylate) Pressure-Sensitive Adhesives. ACS Macro Lett. 12, 787-793 (2023) https://doi.org/10.1021/acsmacrolett.3c00204.
Albanese, K.R., et al. Controlled-Radical Polymerization of α-Lipoic Acid: A General Route to Degradable Vinyl Copolymers. J. Am. Chem. Soc. 145, 22728-22734 (2023) doi: 10.1021/jacs.3c08248.
Alraddadi, M.A., et al. Renewable and recyclable covalent adaptable networks based on bio-derived lipoic acid. Polym. Chem. 12, 5796-5802 (2021) doi: 10.1039/D1PY00754H.
Angulo, A., et al. Comparative Effectiveness of Cyanoacrylate Bioadhesives and Monofilament Suture in Wound Healing: A Histopathological and Physicochemical Study in New Zealand White Rabbit. J. Cytol. Histol. 7(1): 1000395 (2016) doi:10.4172/2157-7099.1000395.
Annabi, N., et al. Engineering a highly elastic human protein-based sealant for surgical applications. Sci. Transl. Med. 9, eaai7466 (2017) doi: 10.1126/scitranslmed.aai7466.
Aoshima, S., et al. A Renaissance in Living Cationic Polymerization. Chem. Rev. 109, 5245-5287 (2009) doi: 10.1021/cr900225g.
Avilla-Royo, E., et al. Biomaterial-based treatments for the prevention of preterm birth after iatrogenic rupture of the fetal membranes, Biomater. Sci., 10, 3695-3715 (2022).
Awaja, F., et al. Adhesion of polymers. Prog. Polym. Sci. 34, 948-968 (2009) doi: 10.1016/j.progpolymsci.2009.04.007.
Bang, E.K., et al. Substrate-Initiated Synthesis of Cell-Penetrating Poly(disulfide)s. J. Am. Chem. Soc. 135, 2088-2091 (2013) doi: 10.1021/ja311961k.
Beharaj, A., et al. Sustainable polycarbonate adhesives for dry and aqueous conditions with thermoresponsive properties. Nat. Commun. 10, 5478 (2019) doi: 10.1038/s41467-019-13449-y.
Bhagat, V., et al. Degradable Adhesives for Surgery and Tissue Engineering. Biomacromolecules. 18, 3009-3039 (2017) doi: 10.1021/acs.biomac.7b00969.
Bhende, S., et al. In Vitro Assessment of Microbial Barrier Properties of Dermabond® Topical Skin Adhesive. Surg. Infect. (Larchmt). 3, 251-257 (2002) doi: 10.1089/109629602761624216.
Boerman, M.A., et al. Next Generation Hemostatic Materials Based on NHS-Ester Functionalized Poly(2-oxazoline)s. Biomacromolecules. 18, 2529-2538 (2017).
Bouten, P.J., et al. The chemistry of tissue adhesive materials. Prog. Polym. Sci. 39, 1375-1405 (2014) doi: 10.1016/j.progpolymsci.2014.02.001.
Carnaghan, H.K., et al. Presealing of the chorioamniotic membranes prior to fetoscopic surgery: Preliminary study with unfertilised chicken egg models. Eur. J. Obstet. Gynecol. Reprod. Biol. 144, S142-S145 (2009) doi: 10.1016/j.ejogrb.2009.02.026.
Chen, B., et al. Mechanism-Driven Metabolic Engineering for Bio-Based Production of Free R-Lipoic Acid in *Saccharomyces cerevisiae* Mitochondria. Front. Bioeng. Biotechnol. 8 (2020) doi:10.3389/fbioe.2020.00965.
Chen, C., et al. Tannic acid-thioctic acid hydrogel: a novel injectable supramolecular adhesive gel for wound healing. Green Chem. 23, 1794-1804 (2021) doi: 10.1039/D0GC02909B.
Chen, J., et al. Supramolecular medical antibacterial tissue adhesive prepared based on natural small molecules. Biomater. Sci. 8, 6235-6245 (2020) doi: 10.1039/D0BM01101K.
Chen, Y., et al. Bioinspired Multiscale Wet Adhesive Surfaces: Structures and Controlled Adhesion. Adv. Funct. Mater. 30, 1905287 (2020) doi: 10.1002/adfm.201905287.
Chuard, N., et al. Cell-penetrating poly(disulfide)s: the dependence of activity, depolymerization kinetics and intracellular localization on their length. Org. Biomol. Chem. 13, 64-67 (2015) doi: 10.1039/C4OB02060J.
Chung, W.J., et al. The use of elemental sulfur as an alternative feedstock for polymeric materials. Nat. Chem. 5, 518-524 (2013) doi: 10.1038/nchem.1624.
Cortes, R.A., et al. Pre-emptive placement of a presealant for amniotic access. Am. J. Obstet. Gynecol. 193, 1197-1203 (2005) doi: 10.1016/j.ajog.2005.05.062.
Cui, C., et al. Recent advances in wet adhesives: Adhesion mechanism, design principle and applications. Prog. Polym. Sci. 116, 101388 (2021) doi: 10.1016/j.progpolymsci.2021.101388.
Cui, C., et al. A self-stabilized and water-responsive deliverable coenzyme-based polymer binary elastomer adhesive patch for treating oral ulcer. Nat. Commun. 14, 7707 (2023) doi: 10.1038/s41467-023-43571-x.

(56) References Cited

OTHER PUBLICATIONS

Deng, Y., et al. Toughening a Self-Healable Supramolecular Polymer by Ionic Cluster-Enhanced Iron-Carboxylate Complexes. Angew. Chem. Int. Ed. 132, 5316-5321 (2020) doi: 10.1002/ange. 201913893.

Deprest, J.A., et al. Endoscopic cord ligation in selective feticide. The Lancet. 348, 890-891 (1996) doi: 10.1016/S0140-6736(05)64760-5.

Deprest, J.A., et al. The making of fetal surgery. Prenat. Diagn., 30: 653-667 (2010) https://doi.org/10.1002/pd.2571.

Devlieger, R., et al. Fetal membrane healing after spontaneous and iatrogenic membrane rupture: A review of current evidence. Am. J. Obstet. Gynecol. 195, 1512-1520 (2006) doi: 10.1016/j.ajog.2006. 01.074.

Dikshit, K.V., et al. Pressure-Sensitive Supramolecular Adhesives Based on Lipoic Acid and Biofriendly Dynamic Cyclodextrin and Polyrotaxane Cross-Linkers. ACS Appl. Mater. Interfaces 15: 17256-17267 (2023).

Dillard, D.A., et al. Advances in Structural Adhesive Bonding, Woodhead Publishing. Chapter 7 p. 223-224 (2010).

Droesbeke, M.A., et al. Biosourced terpenoids for the development of sustainable acrylic pressure-sensitive adhesives via emulsion polymerisation. Green Chem. 22, 4561-4569 (2020) doi: 10.1039/D0GC01350A.

Endo, K., et al. Synthesis and characterization of poly(1,2-dithiane). Macromolecules. 37, 3143-3150 (2004).

Endo, K., et al. Thermal polymerization of 1, 2-dithiane. Polym. J. 37, 512-516 (2005) doi: 10.1295/polymj.37.512.

European Centre for Disease Prevention and Control. Healthcare-associated infections: surgical site infections. In: ECDC. Annual epidemiological report for 2018-2020. Stockholm: ECDC; 2023.

Gillman, N., et al. Surgical applications of intracorporal tissue adhesive agents: current evidence and future development. Expert Rev. Med. Devices. 17, 443-460 (2020) doi: 10.1080/17434440. 2020.1743682.

Guo, J., et al. Glutathione-triggered biodegradable poly(disulfide)s: ring-opening copolymerization and potent antibacterial activity. Polym. Chem. 13, 6637-6649 (2022) doi: 10.1039/D2PY01084D.

Gupta, et al. Effect of nanoalumina in epoxy adhesive on lap shear strength and fracture toughness of aluminium joints. J. Adhes. 97, 117-139 (2021) doi: 10.1080/00218464.2019.1641088.

Hopewell, J., et al. Plastics recycling: challenges and opportunities. Philos. Trans. R. Soc. B Biol. Sci. 364, 2115-2126 (2009) doi: 10.1098/rstb.2008.0311.

Houk, J., et al. Structure-Reactivity Relations for Thiol-Disulfide Interchange. J. Am. Chem. Soc. 109, 6825-6836 (1987) doi: 10.1021/ja00256a040.

Hüttner, F.J., et al. 2-octyl cyanoacrylate sealing of the pancreatic remnant after distal pancreatectomy—A prospective pilot study. PLoS One. 13 (2018) doi:10.1371/journal.pone.0205748.

Hwang, D., et al. Metamaterial adhesives for programmable adhesion through reverse crack propagation. Nat. Mater. 22, 1030-1038 (2023) doi: 10.1038/s41563-023-01577-2.

Jojibabu, P., et al. Effect of different carbon nano-fillers on rheological properties and lap shear strength of epoxy adhesive joints. Compos. Part A Appl. Sci. Manuf. 82, 53-64 (2016) doi: 10.1016/j.compositesa.2015.12.003.

Ke, X., et al. An instant, repeatable and universal supramolecular adhesive based on natural small molecules for dry/wet environments. Chem. Eng. J. 442, 136206 (2022).

Ke, X., et al. Natural Small Biological Molecule Based Supramolecular Bioadhesives with Innate Photothermal Antibacterial Capability for Nonpressing Hemostasis and Effective Wound Healing. ACS Appl. Mater. Interfaces. 14, 53546-53557 (2022) doi: 10.1021/acsami. 2c17415.

Kisanuki, A., et al. Ring-opening polymerization of lipoic acid and characterization of the polymer. J. Polym. Sci. Part A Polym. Chem. 48, 5247-5253 (2010) doi: 10.1002/pola.24325.

Law, K.L., et al. Reducing environmental plastic pollution by designing polymer materials for managed end-of-life. Nat. Rev. Mater. 7, 104-116 (2022) doi: 10.1038/s41578-021-00382-0.

Lee, Y., et al. Visualization of the Degradation of a Disulfide Polymer, Linear Poly (ethylenimine sulfide), for Gene Delivery. Bioconjug. Chem. 18, 13-18 (2007) doi: 10.1021/bc060113t.

Lei, Y.F., et al. Fully Bio-Based Pressure-Sensitive Adhesives with High Adhesivity Derived from Epoxidized Soybean Oil and Rosin Acid. ACS Sustain. Chem. Eng. 8, 13261-13270 (2020) doi: 10.1021/acssuschemeng.0c03451.

Lennox-Hvenekilde, D., et al. Metabolic engineering of *Escherichia coli* for high-level production of free lipoic acid. Metab. Eng. 76, 39-49 (2023) doi: 10.1016/j.ymben.2023.01.004.

Leonard, F., et al. Synthesis and degradation of poly (alkyl α-cyanoacrylates). J. Appl. Polym. Sci. 10, 259-272 (1966).

Li, J., et al. Tough adhesives for diverse wet surfaces. Science 357, 378-381 (2017) doi: 10.1126/science.aah6362.

Li, J., et al. Supramolecular Pressure-Sensitive Adhesives with Rapid, Strong, Water-Resistant, and Underwater Adhesion. Adv. Mater. Interfaces. 10, 2202005 (2023) doi: 10.1002/admi. 202202005.

Liu, C., et al. Biological Glue from Only Lipoic Acid for Scarless Wound Healing by Anti-inflammation and TGF-β Regulation. Chem. Mater. 35, 2588-2599 (2023) doi: 10.1021/acs.chemmater.3c00049.

Liu, Y., et al. Architecture-Controlled Ring-Opening Polymerization for Dynamic Covalent Poly(disulfide)s. J. Am. Chem. Soc. 141, 17075-17080 (2019) doi: 10.1021/jacs.9b08957.

Mansourian-Tabaei, et al. Lap shear strength and thermal stability of diglycidyl ether of bisphenol a/epoxy novolac adhesives with nanoreinforcing fillers. J. Appl. Polym. Sci. 131 (2014) doi: 10.1002/app.40017.

Mogami, et al. Healing of Preterm Ruptured Fetal Membranes. Sci. Rep. 7, 13139 (2017) doi: 10.1038/s41598-017-13296-1.

Moriche, R., et al. Thermal conductivity and lap shear strength of GNP/epoxy nanocomposites adhesives. Int. J. Adhes. Adhes. 68, 407-410 (2016) doi: 10.1016/j.ijadhadh.2015.12.012.

Mulder, T., et al. Prevention of severe infectious complications after colorectal surgery using oral non-absorbable antimicrobial prophylaxis: results of a multicenter randomized placebo-controlled clinical trial. Antimicrob. Resist. Infect. Control. 9, 84 (2020) doi: 10.1186/s13756-020-00745-2.

Nam, S., et al. Polymeric Tissue Adhesives. Chem. Rev. 121, 11336-11384 (2021) doi: 10.1021/acs.chemrev.0c00798.

Narang, U., et al. In-Vitro Analysis for Microbial Barrier Properties of 2-Octyl Cyanoacrylate-Derived Wound Treatment Films. J. Cutan. Med. Surg. Inc. Med. Surg. Dermatology. 7, 13-19 (2003) doi: 10.1007/s10227-002-1155-5.

Packham, D.E. "15—The environmental impact of adhesives" in, F. Pacheco-Torgal, L. F. Cabeza, J. Labrincha, A. B. T.-E. C. and B. M. de Magalhães, Eds. (Woodhead Publishing, 2014 https://www.sciencedirect.com/science/article/pii/B9780857097675500157), pp. 338-367.

Park, D.H., et al. In vitro degradation and cytotoxicity of alkyl 2-cyanoacrylate polymers for application to tissue adhesives. J. Appl. Polym. Sci. 89, 3272-3278 (2003) doi: 10.1002/app.12452.

Peng, X., et al. Coacervate-Derived Hydrogel with Effective Water Repulsion and Robust Underwater Bioadhesion Promotes Wound Healing. Adv. Sci. 9, 2203890 (2022) doi: 10.1002/advs. 202203890.

Petrie, E., et al. Cyanoacrylate Adhesives in Surgical Applications. Rev. Adhes. Adhes. 2, 253-310 (2014) doi: 10.7569/RAA.2014. 097306.

Pocius, A.V. Adhesion and Adhesives Technology: An Introduction; Carl Hanser Verlag: Munich, Germany. Chapter 6 p. 162-168 (2012).

Rosenthal-Kim, E.Q., et al. Visualization of the architecture of poly(α-lipoic acid) using atomic force microscopy. Eur. Polym. J. 65, 232-237 (2015) doi: 10.1016/j.eurpolymj.2015.02.020.

Sawamoto, M., et al. Modern cationic vinyl polymerization. Prog. Polym. Sci. 16, 111-172 (1991) doi: 10.1016/0079-6700(91)90008-9.

(56) References Cited

OTHER PUBLICATIONS

Shen, M., et al. Hydrolysis and Solvolysis as Benign Routes for the End-of-Life Management of Thermoset Polymer Waste. Annu. Rev. Chem. Biomol. Eng. 11, 183-201 (2020) doi: 10.1146/annurev-chembioeng-120919-012253.

Shen, M., et al. Degradation Behavior of Biobased Epoxy Resins in Mild Acidic Media. ACS Sustain. Chem. Eng. 9, 438-447 (2021) doi: 10.1021/acssuschemeng.0c07621.

Singer, A.J., et al. The cyanoacrylate topical skin adhesives. Am. J. Emerg. Med. 26, 490-496 (2008) doi: 10.1016/j.ajem.2007.05.015.

Smith, R.L., et al. Wound Infection After Elective Colorectal Resection. Ann. Surg. 239 (2004) doi: 10.1097/01.sla.0000124292.21605.99.

Taboada, G.M., et al. Overcoming the translational barriers of tissue adhesives. Nat. Rev. Mater. 5, 310-329 (2020) doi: 10.1038/s41578-019-0171-7.

Thomas, R.C., et al. Disulfide Polymers of DL-α-Lipoic Acid. J. Am. Chem. Soc. 78, 6148-6149 (1956) doi: 10.1021/ja01604a053.

Tiu, B.D.B., et al. Enhanced Adhesion and Cohesion of Bioinspired Dry/Wet Pressure-Sensitive Adhesives. ACS Appl. Mater. Interfaces. 11, 28296-28306 (2019) doi: 10.1021/acsami.9b08429.

Wang, B.S., et al. Acid-catalyzed Disulfide-mediated Reversible Polymerization for Recyclable Dynamic Covalent Materials. Angew. Chemie Int. Ed. (2023) doi:10.1002/anie.202215329.

Wang, Z., et al. Bioinspired chemical design to control interfacial wet adhesion. Chem. 9, 771-783 (2023) doi: 10.1016/j.chempr.2023.02.012.

Westerman, C.R., et al. Sustainably sourced components to generate high-strength adhesives. Nature. 621, 306-311 (2023) doi: 10.1038/s41586-023-06335-7.

Winkler, S.M., et al. Biomaterials in fetal surgery. Biomater. Sci. 7, 3092-3109 (2019) doi: 10.1039/C9BM00177H.

Wu, S.J., et al. Bioadhesive Technology Platforms. Chem. Rev. 123, 14084-14118 (2023) doi: 10.1021/acs.chemrev.3c00380.

Yuk, H., et al. Dry double-sided tape for adhesion of wet tissues and devices. Nature. 575, 169-174 (2019).

Zhang, Q., et al. Exploring a naturally tailored small molecule for stretchable, self-healing, and adhesive supramolecular polymers. Sci. Adv. 4, eaat8192 (2018) doi: 10.1126/sciadv.aat8192.

Zhang, Q., et al. Assembling a Natural Small Molecule into a Supramolecular Network with High Structural Order and Dynamic Functions. J. Am. Chem. Soc. 141, 12804-12814 (2019) doi: 10.1021/jacs.9b05740.

Zhang, Q., et al. Dual closed-loop chemical recycling of synthetic polymers by intrinsically reconfigurable poly (disulfides). Matter. 4, 1352-1364 (2021) doi: 10.1016/j.matt.2021.01.014.

Zhang, X., et al. 1, 2-Dithiolane-Derived Dynamic, Covalent Materials: Cooperative Self-Assembly and Reversible Cross-Linking. J. Am. Chem. Soc. 139, 3822-3833 (2017) doi: 10.1021/jacs.7b00039.

Zhao, Y., et al. Supramolecular Adhesive Hydrogels for Tissue Engineering Applications. Chem. Rev. 122, 5604-5640 (2022) doi: 10.1021/acs.chemrev.1c00815.

\* cited by examiner

FG = side chain of alpha-amino acid

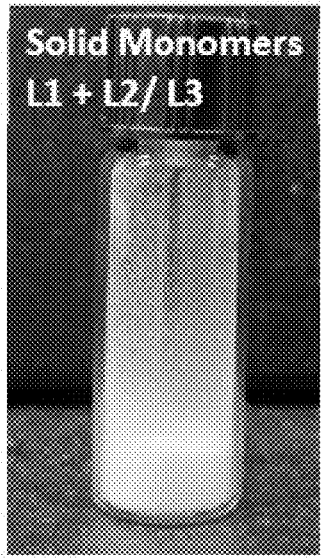
FIG. 1C1
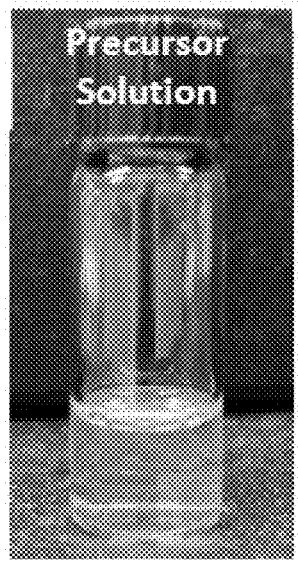
FIG. 1C2
FIG. 1C3
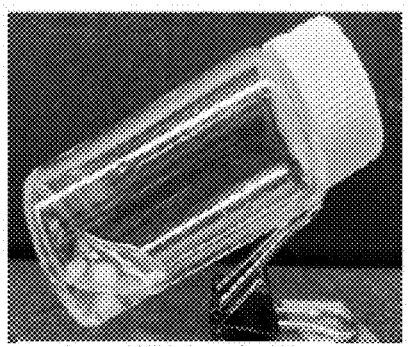
Liquid Precursor
(L1 + L2 + L4)
FIG. 1D1
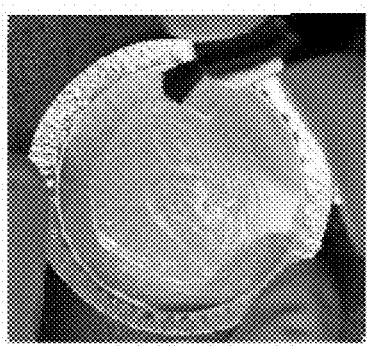
Brushing of the
Liquid Precursor
FIG. 1D2
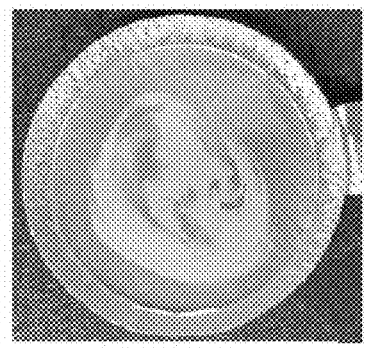
Aqueous
Polymerisation
FIG. 1D3

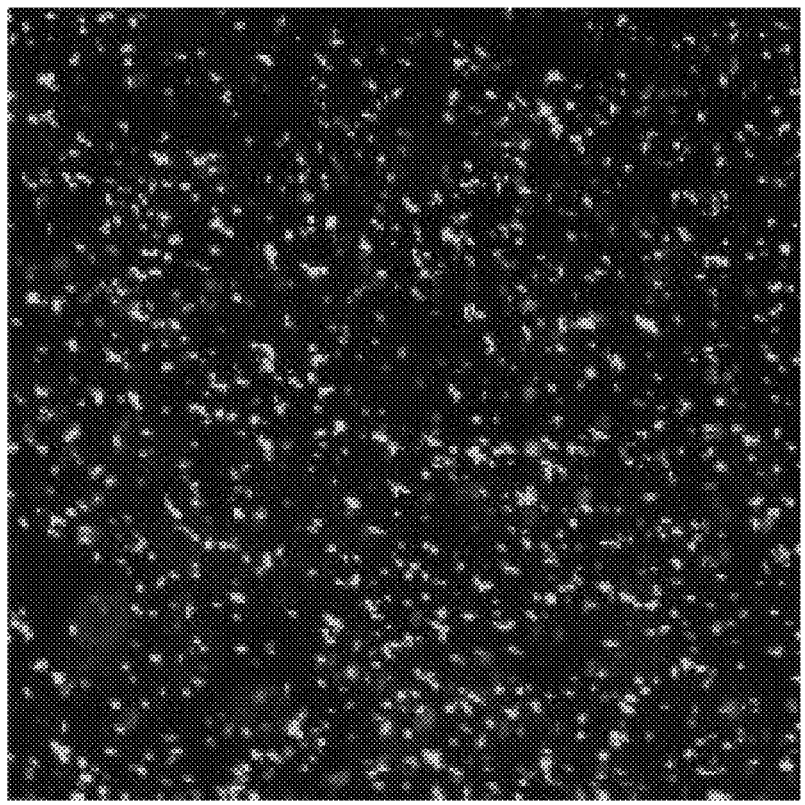
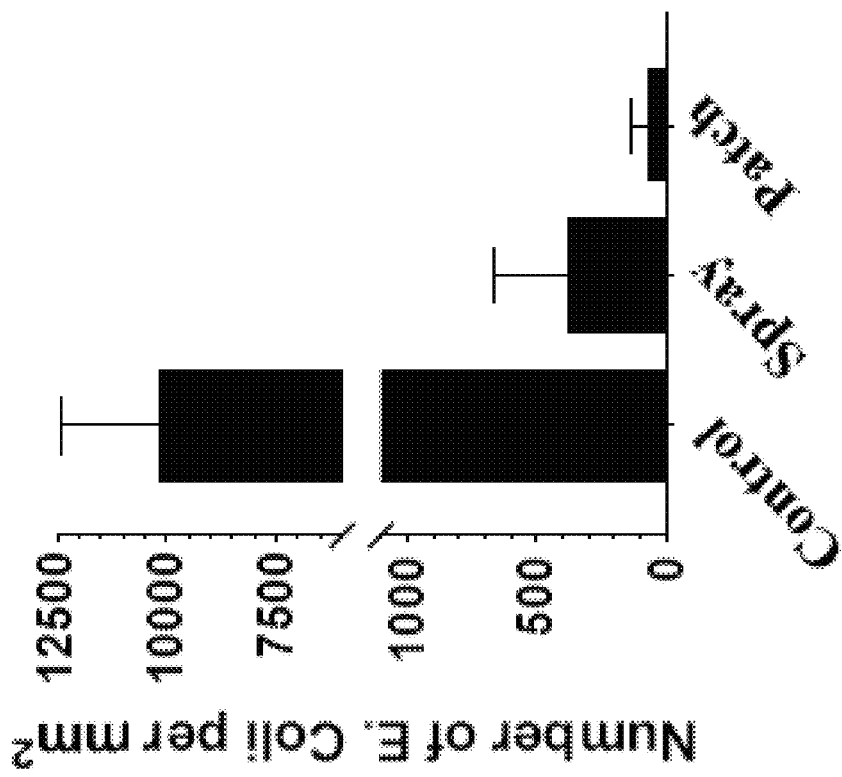
FIG. 4G
FIG. 4H

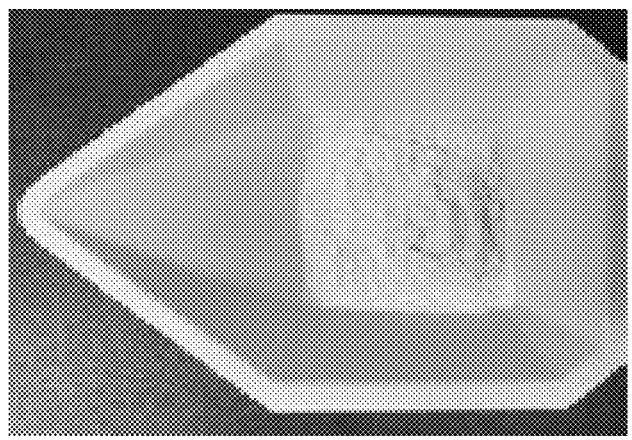
FIG. 5B3
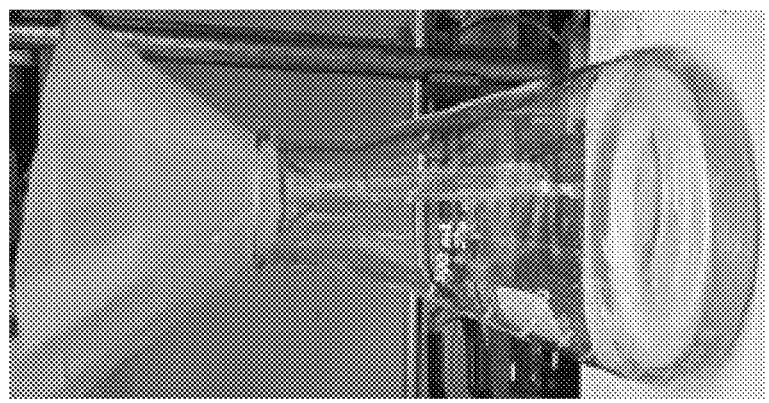
FIG. 5B2
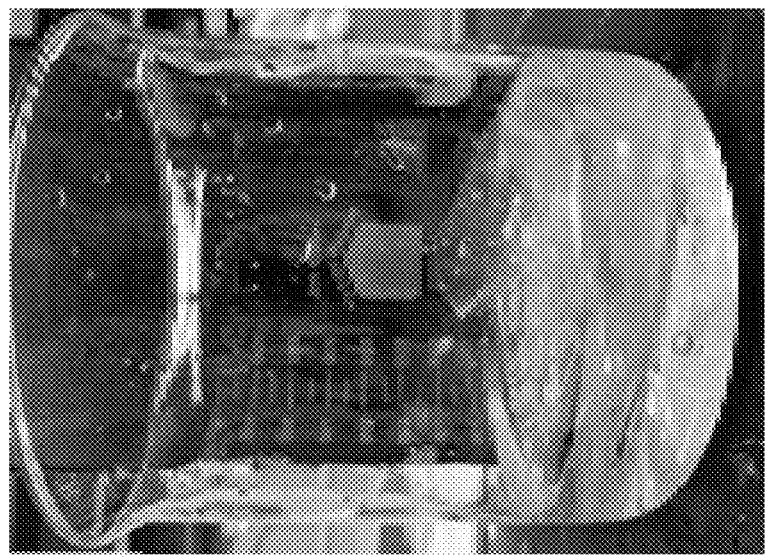
FIG. 5B1

ADJUSTABLY STABLE ADHESIVE COMPOSITIONS FOR MEDICAL AND NON-MEDICAL USES, AND RECYCLING

CROSS-REFERENCE TO RELATED APPLICATIONS

This application claims priority to U.S. Provisional Application Nos. 63/459,157, filed Apr. 13, 2023; 63/502,429, filed May 16, 2023; and 63/626,358, filed Jan. 29, 2024, each of which is hereby incorporated herein by reference in its entirety.

BACKGROUND

Field of the Invention

The systems and methods taught herein are generally directed to adhesive compositions.

Description of the Related Art

Adhesives are an important part of everyday life, and they're found in both medical and non-medical sectors. Examples of non-medical applications are in the consumer, industrial, and military sectors. It should be appreciated that there is plenty of room for technical innovations in the development of adhesives, especially in adhesives that require particular functionalities for specialized uses. It should be appreciated that rapid curing and high mechanical strength are desired features of many adhesives. Interestingly, because many applications require adhering to a wet surface, the ability to adhere well to wet surfaces is also a highly desired feature of adhesives. Many desirable adhesives are manmade and, unfortunately, it is unusual for a manmade adhesive to adhere well to a wet surface. Moreover, another desired feature of adhesives is recyclability.

Non-medical adhesives are a large market. Pressure sensitive adhesives (PSAs), for example, constitute a large fraction of the overall global adhesives market, have many uses across market sectors, and are found in consumer adhesive tapes, sticky notes, and product labels, to name a few. PSAs are designed for low cost/high-volume use, are rarely effective for permanent adhesion, and require 'stickiness', which is a feature that may be found in polymers having a low glass transition temperature (Tg), usually well below 0° C. As such, low Tg viscoelastic polyacrylates have been as PSAs but, unfortunately, these adhesives are fossil-fuel-derived and not recyclable. Since sustainable, reusable, or recyclable adhesives are desired in adhesives, including PSAs, the lack of such adhesives is driving research and innovation in adhesives. Some sustainable and recyclable PSAs have been developed but, unfortunately, their high costs of production and recycling limit their uses.

Medical adhesives, for example, are a specialized type of adhesive having a wide variety of performance requirements that vary by the particular use of the adhesive. Desirable features include biocompatibility, biodegradability, high mechanical strength, infection barrier properties that can include antimicrobial activity, and purity of toxic compounds, to name a few. Medical adhesives that are biodegradable would be appreciated, for example, in adhesives that are used internally in surgical procedures. Medical adhesives configured to have anti-inflammatory activity, anti-microbial activity, hemostat activity, and the like, would also be appreciated. Medical adhesives can also require a higher level of purity from toxic compounds, as toxic compounds can be potentially harmful to tissues and organs.

Adhesives that work in both medical and non-medical markets are desired and quite scarce. A rare example of adhesives found in both medical and non-medical markets are the cyanoacrylates, which are commonly known as "superglues". The superglues can be used, for example, in external wound closures due to their rapid cure, high strength, and good infection barrier properties. Unfortunately, these cyanoacrylates have their downfalls. While the cyanoacrylates are approved and widely used for external wound closure, they're not approved by the Food and Drug Administration (FDA) for many internal uses because of their high cytotoxicity and inability to degrade for excretion by the body. Hydrogel-based adhesives, such as fibrin glue, albumin glue, and polyethylene glycol (PEG)-based glues, have been approved by the FDA for internal procedures but, unfortunately, the hydrogel adhesives suffer from poor mechanical strength, often at least an order of magnitude weaker than the superglues.

Recently, poly($\alpha$-lipoic acid) has attracted significant attention due to its excellent mechanical and adhesion strength, along with cost-effective production and close-loop chemical recycling. $\alpha$-lipoic acid (L1), also known as thioctic acid, is a five-member cyclic disulfide with a carboxylic acid side chain. It is an essential cofactor for aerobic metabolism in animals. The (R)- form of $\alpha$-lipoic acid is found in nature, but a racemic mixture of $\alpha$-lipoic acid is also considered safe and has been widely used as a dietary supplement. $\alpha$-lipoic acid is mainly used as an antioxidant due to its exceptional ability to quench reactive oxygen species.

Besides having a favorable biological profile, $\alpha$-lipoic acid also shows exceptional potential for ring-opening polymerization due to the release of ring strain from the polymerization. In 1956, R. C. Thomas and L. J. Reed first observed that $\alpha$-lipoic acid undergoes polymerization thermally, when heated above its melting temperature. Unfortunately, the polymer had poor stability at ambient conditions due to spontaneous depolymerization. Since then, multiple attempts have been made to synthesize a stable form poly($\alpha$-lipoic acid). It has been proposed that the thermal polymerization of lipoic acid proceeds via a radical mechanism, and the presence of the active terminal chain end radical is responsible for the depolymerization.

Although asparagusic acid is known to exist in nature, isolation of asparagusic acid on a larger scale in its pure monomeric form is challenging. The molecule can be synthesized in the laboratory or purchased at a high cost but consists of the monomeric and oligomeric mixture (<10% oligomer). Poly(asparagusic acid) does not exist in nature, and has not been produced in the art. As such, poly(asparagusic acid) is novel and inventive as a composition. Asparagusic acid (1,2-dithiolane-4-carboxylic acid) is unique to asparagus and is of great interest as a monomer due to research of pharmacological properties that include activity the treatment of urinary problems, fertility, breast milk production, and diseases that include kidney, bladder, rheumatic, liver disease, asthma and cancer.

The market for adhesives is highly segmented. For example, superglues are used primarily for external wound closure, and hydrogel adhesives are used primarily internal adhesion and sealing. No known adhesive can cross-over these market segments and serve as an adhesive and sealant for both external and internal medical uses, and this is a longfelt-by-unsolved need.

A person of skill in adhesives will appreciate having adjustably stable adhesive compositions that can be configured for medical and non-medical uses, as well as for ease of recycling. An example is a poly(α-lipoic acid) that is sufficiently stable, easily produced, and has a high mechanical strength when adhered to a variety of substrates whether wet or dry. The choice of stabilizer moieties further allows to design the stability of the polymer, by choosing whether the stabilizer is needed at all for a desired use, and then adjusting the stability of the polymer for it's desired use by choosing a stabilizer moiety having a desired bond strength between the stabilizer and polymer. The same is true of the choice of terminator moieties by choosing whether to the terminator moiety is needed at at all for the desired use, and then further adjusting the stability of the polymer choosing a terminator moiety having a desired bond strength between the terminator and polymer. It will also be appreciated to have an adhesive that is easily degraded and recycled due to the presence of a homogeneous chemistry when depolymerized. Such features are beneficial in any application of the adhesive, whether medical or non-medical. In medical uses, however, it will also be appreciated to have an adhesive that is biocompatible and biodegradable for medical applications, and can provide therapeutic activity through it's monomers upon biodegradation without an unacceptable level of toxicity. And, an adhesive that has barrier properties to block the spread of infections is also desirable. Moreover, a medical grade adhesive that can be used both external to the body and internal to the body would solve that longfelt-but-unsolved need.

SUMMARY

Adjustably stable adhesive compositions for medical and non-medical uses are provided, and the adhesive compositions can also be configured to be easily recycled. The adhesive compositions can include cyclic disulfide monomers, oligomers of reactions between the cyclic disulfides, polymers of the cyclic disulfides, solid articles formed formed from the polymers, and any combination thereof. Methods of making and using the adhesive compositions are included for both medical and non-medical applications, including use of the adhesive compositions on any of a variety of substrates that include biological tissue; biomaterials, including synthetics and natural such as bone, wood, and cellulosics; metals and alloys; polymers, plastics, and rubbers; ceramics; composites; and, any combination of these materials. The adhesives can also adhere to substrates in any of a variety of environmental conditions that include ambient atmospheric conditions, wet conditions that include adhering materials underwater, and in a wide variety of temperatures and pressures, such as those temperatures and pressures found in medical environments, including in living tissue, as well as many residential, commercial, industrial, and manufacturing environments.

In some embodiments, the technology includes adhesive compositions, comprising a polymerizable monomer selected from the group consisting of substituted cyclic disulfide molecules having from 2 to 4 C atoms in a cyclic ring with a disulfide bond, the substituted cyclic disulfide molecules functional to polymerize through a ring-opening reaction in a polar, protic solvent to form a polymer having a first active thiol end and a second active thiol end; and, a plurality of repeating units having a substituted dithioalkyl structure from the ring opening reaction as follows

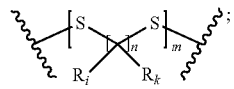

wherein, n is an integer ranging from 2 to 4;

each $R_i$ and $R_k$ is independently selected from the group consisting of H; alkyl, cycloalkyl, alkenyl, alkynyl, and aryl groups having from 1-8 carbons; hydroxylated alkyl, cycloalkyl, alkenyl, alkynyl, and aryl groups having from 1-8 carbons; and, carboxylated alkyl, cycloalkyl, alkenyl, alkynyl, and aryl groups having from 1-8 carbons; wherein, i and k are integers and at least one $R_i$ or $R_k$ in each repeating unit includes a carbonyl functionality;

and, m is an integer;

and, a plurality of stabilizer molecules configured to stabilize the first active thiol end of the polymer, the plurality of stabilizer molecules being the substituted cyclic disulfide molecules derivatized to include a functional group that forms a first labile bond with the first active thiol end, the first labile bond selected from the group consisting of a thioester bond, a thiocarbamate bond, and a thioether bond;

wherein, the repeating units and the stabilizer molecules are the same, or substantially the same, chemical moieties following a depolymerization of the polymer.

In some embodiments, the technology includes adhesive compositions further including a plurality of terminator molecules having a functional group that forms a second labile bond with the second active thiol end of the polymer.

In some embodiments, each of the plurality of terminator molecules is selected from the group consisting of R'OH, R'CO$_2$H, and R'SH, where R' is an alkyl, cycloalkyl, alkenyl, cycloalkenyl, alkynyl, cycloalkynyl, an aryl group having from 1-8 carbons; and, the second labile bond is selected from the group consisting of thioethers, thioesters, and disulfides.

In some embodiments, the plurality of terminator molecules is selected from the group consisting of alkanols having from 1-8 carbons, alkanoic acids having from 1-8 carbons, and alkylthiols having from 1-8 carbons, and the second labile bond is selected from the group consisting of thioethers, thioesters, and disulfides.

In some embodiments, each of the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality.

In some embodiments, the plurality of substituted cyclic disulfide molecules is a substituted 1,2-dithietane, and the repeating unit is a substituted 1,2-dithioethyl structure.

In some embodiments, the plurality of substituted cyclic disulfide molecules is substituted 1,2-dithiolane, and the repeating unit is a substituted 1,3-dithioethyl structure.

In some embodiments, the plurality of substituted cyclic disulfide molecules is a substituted 1,2-dithiane, and the repeating unit is a substituted 1,4-dithioethyl structure.

In some embodiments, the repeating unit is a substituted 1,3-dithiopropyl structure as follows

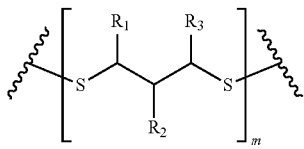

wherein,
m is an integer;
$R_i$ includes $R_1$, $R_2$, and $R_3$; and,
each $R_k$ is H;
and,
each stabilizer molecule includes the substituted 1,3-dithiopropyl structure.

In some embodiments, the repeating unit is a substituted 1,3-dithiopropyl structure as follows

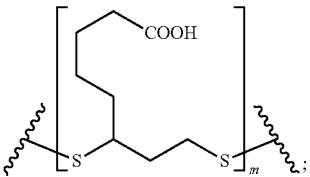

wherein,
m is an integer;
$R_1$ is a pentanoic acid group, and $R_2$ and $R_3$ are each H;
and,
each stabilizer molecule includes the substituted 1,3-dithiopropyl structure, wherein $R_1$ is a pentanoic acid group, and $R_2$ and $R_3$ are each H.

In some embodiments, the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality, the terminator molecules functioning to form a second labile bond with the second active thiol end of the polymer to further stabilize the polymer.

In some embodiments, the repeating unit has a substituted 1,3-dithiopropyl structure

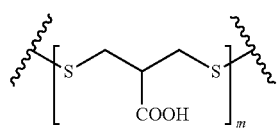

wherein,
m is an integer;
$R_1$ and $R_3$ are H, and $R_2$ is a carboxylic acid group;
and,
each stabilizer molecule includes the substituted 1,3-dithiopropyl structure, wherein $R_1$ and $R_3$ are H and $R_2$ is a carboxylic acid group.

The adhesive compositions can polymerize to form adhesive polymers. And, in some embodiments, the adhesive polymers are stabilized and a recyclable polydisulfide polymer, comprising:

a repeating unit having a substituted dithioalkyl structure as follows

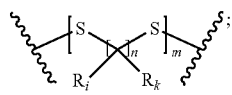

wherein,
n is an integer ranging from 2 to 4;
each $R_i$ and $R_k$ is independently selected from the group consisting of H; alkyl, cycloalkyl, alkenyl, alkynyl, and aryl groups having from 1-8 carbons; hydroxylated alkyl, cycloalkyl, alkenyl, alkynyl, and aryl groups having from 1-8 carbons; and, carboxylated alkyl, cycloalkyl, alkenyl, alkynyl, and aryl groups having from 1-8 carbons; wherein, i and k are integers and at least one $R_i$ or $R_k$ in each repeating unit includes a carbonyl functionality;
m is an integer;
a first active thiol end and a second active thiol end; and,
a plurality of stabilizer molecules configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioether bond;
wherein, the repeating units and the stabilizer molecules are the same, or substantially the same, chemical moieties following a degradation of the polymer during a recycling of the polymer.

In some embodiments, the stabilized and recyclable polydisulfide polymer further includes a plurality of terminator molecules having a functional group that forms a second labile bond with the second active thiol end of the polymer.

In some embodiments, each of the plurality of terminator molecules is selected from the group consisting of R'OH, R'CO$_2$H, and R'SH, where R' is an alkyl, cycloalkyl, alkenyl, cycloalkenyl, alkynyl, cycloalkynyl, or aryl group having from 1-8 carbons, the second labile bond selected from the group consisting of thioethers, thioesters, and disulfides.

In some embodiments, each of the plurality of terminator molecules is selected from the group consisting of alkanols having from 1-8 carbons, alkanoic acids having from 1-8 carbons, and alkylthiols having from 1-8 carbons, the second labile bond selected from the group consisting of thioethers, thioesters, and disulfides.

In some embodiments, the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality, the terminator molecules functioning to form a second labile bond with the second active thiol end of the polymer to further stabilize the polymer.

In some embodiments, the dithioalkyl repeating unit is a substituted 1,2-dithioethyl repeating unit.

In some embodiments, the dithioalkyl repeating unit is a substituted 1,3-dithiopropyl repeating unit.

In some embodiments, the dithioalkyl repeating unit is a substituted 1,4-dithiobutyl repeating unit.

In some embodiments, the dithioalkyl repeating unit is a substituted 1,3-dithiopropyl structure as follows

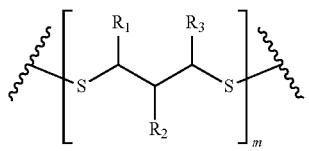

wherein,
$R_i$ includes $R_1$, $R_2$, and $R_3$; and,
each $R_k$ is H; and,
m is an integer;
and,
each stabilizer group in the plurality of stabilizer groups includes the substituted 1,3-dithiopropyl structure.

In some embodiments, the repeating unit is a substituted 1,3-dithiopropyl structure as follows

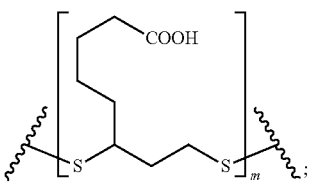

wherein,
m is an integer; and,
$R_1$ is a pentanoic acid group, and $R_2$ and $R_3$ are each H; and,
each of the stabilizer groups includes the 1,3-dithiopropyl structure in which $R_1$ is a pentanoic acid group, and $R_2$ and $R_3$ are each H.

In some embodiments, the repeating unit is a substituted 1,3-dithiopropyl structure as follows

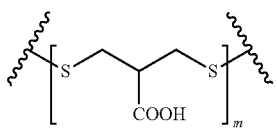

wherein,
m is an integer;
$R_1$ and $R_3$ are H, and $R_2$ is a carboxylic acid group; and,
each of the stabilizer groups includes the 1,3-dithiopropyl repeating unit in which $R_1$ and $R_3$ are H, and $R_2$ is a carboxylic acid group.

In some embodiments, the polymer has the following structure

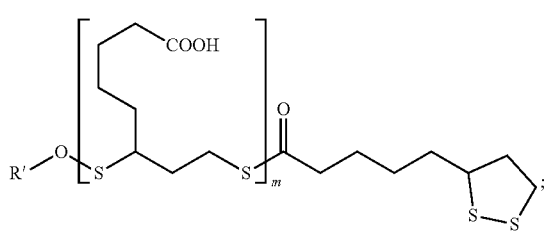

wherein,
m is an integer; and,
R' is an alkyl, cycloalkyl, alkenyl, cycloalkenyl, alkynyl, cycloalkynyl, or aryl group having from 1-8 carbons.

In some embodiments, R' is an ethyl group.

In some embodiments, the polymer has the following structure

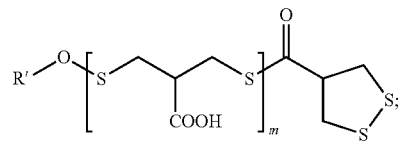

wherein,
m is an integer; and,
R' is an alkyl, cycloalkyl, alkenyl, cycloalkenyl, alkynyl, cycloalkynyl, or aryl group having from 1-8 carbons.

In some embodiments, R' is an ethyl group.

In some embodiments, the polymer is branched from at least one of $R_i$ or $R_k$ in a first dithioalkyl repeating unit, the at least one $R_i$ or $R_k$ including a carbonyl functionality in a thioester bond with a second dithioalkyl repeating unit.

In some embodiments, the polymer further comprises a plurality of terminator molecules having a functional group that forms a second labile bond with the second active thiol end of the polymer.

In some embodiments, the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality, the terminator molecules functioning to form a second labile bond with the second active thiol end of the polymer to further stabilize the polymer.

In some embodiments, the polymer includes the following branched structure

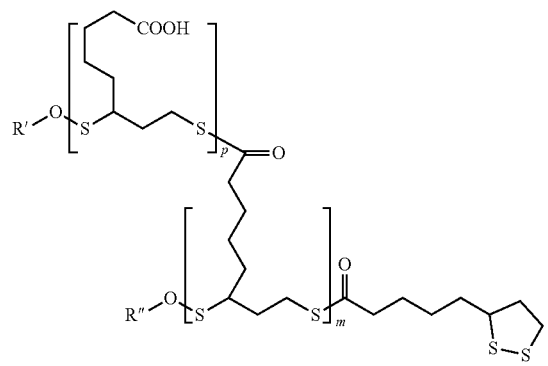

wherein,
m is an integer;
p is an integer; and,
R' and R" are each independently selected from a group consisting of an alkyl, cycloalkyl, alkenyl, cycloalkenyl, alkynyl, cycloalkynyl, or aryl group having from 1-8 carbons.

In some embodiments, R' and R" are ethyl groups.

In some embodiments, the polymer includes the following branched structure

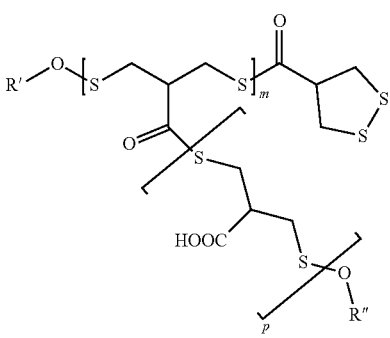

wherein, m is an integer;

p is an integer; and,

R' and R" are each independently selected from a group consisting of an alkyl, cycloalkyl, alkenyl, cycloalkenyl, alkynyl, cycloalkynyl, or aryl group having from 1-8 carbons.

In some embodiments, R' and R" are ethyl groups.

There are a several ways to make the variety of adhesives provided herein. In some embodiments, a method of making an adhesive composition comprises obtaining a plurality of substituted cyclic disulfide molecules having from 2 to 4 C atoms in a cyclic ring with a disulfide bond, the substituted cyclic disulfide molecules functional to polymerize through a ring-opening reaction in polar, protic solvent to form a polymer having
a first active thiol end and a second active thiol end; and,
a repeating unit having a substituted dithioalkyl structure as follows

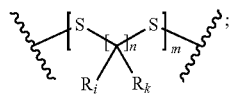

wherein, n is an integer ranging from 2 to 4;

each $R_i$ and $R_k$ is independently selected from the group consisting of H; alkyl, cycloalkyl, alkenyl, alkynyl, and aryl groups having from 1-8 carbons; hydroxylated alkyl, cycloalkyl, alkenyl, alkynyl, and aryl groups having from 1-8 carbons; and, carboxylated alkyl, cycloalkyl, alkenyl, alkynyl, and aryl groups having from 1-8 carbons; wherein, i and k are integers and at least one $R_i$ or $R_k$ in each repeating unit includes a carbonyl functionality;

m is an integer;

obtaining a plurality of stabilizer molecules configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioether bond;

polymerizing the plurality of the substituted cyclic disulfide molecules to create the polymer in the polar, protic solvent; and, stabilizing the polymer by reacting the plurality of stabilizer molecules with the first active end in the polar, protic solvent;

wherein, the repeating units and the stabilizer molecules are the same, or substantially the same, chemical moieties following a degradation of the polymer during a recycling of the polymer.

In some embodiments, the polar, protic solvent is water, ethanol, or a combination of water and ethanol.

In some embodiments, the methods further comprise
further stabilizing the polymer by reacting a plurality of terminator molecules with the polymer in the polar, protic solvent; each of the terminator molecules having a functional group that forms a second labile bond with the second active thiol end of the polymer.

In some embodiments, each of the plurality of terminator molecules is selected from the group consisting of R'OH, $R'CO_2H$, and R'SH, where R' is an alkyl, cycloalkyl, alkenyl, cycloalkenyl, alkynyl, cycloalkynyl, or aryl group having from 1-8 carbons, the second labile bond selected from the group consisting of thioethers, thioesters, and disulfides.

In some embodiments, each of the plurality of terminator molecules is selected from the group consisting of alkanols having from 1-8 carbons, alkanoic acids having from 1-8 carbons, and alkylthiols having from 1-8 carbons, the second labile bond selected from the group consisting of thioethers, thioesters, and disulfides.

In some embodiments, the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality, the terminator molecules functioning to form a second labile bond with the second active thiol end of the polymer to further stabilize the polymer.

In some embodiments,
the plurality of substituted cyclic disulfide molecules is selected from the group consisting of a substituted 1,2-dithietane, a substituted 1,2-dithiolane, a substituted 1,2-dithiane, and combinations thereof; and,
the plurality of stabilizer molecules is selected from the group consisting of functionalized derivatives of the substituted 1,2-dithietane, functionalized derivatives of the substituted 1,2-dithiolane, functionalized derivatives of the substituted 1,2-dithiane, and combinations thereof, the derivatives functionalized to form the labile bond when reacted with the first active end.

In some embodiments, the plurality of substituted cyclic disulfide molecules is a plurality of lipoic acid molecules, asparagusic acid molecules, or a combination thereof.

In some embodiments, the plurality of stabilizer molecules are functionalized derivatives of the lipoic acid molecules, functionalized derivatives of the asparagusic acid molecules, or a combination thereof.

In some embodiments, the plurality of stabilizer molecules is selected from the group consisting of

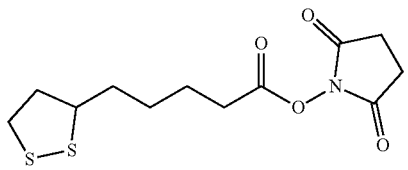 [SMILES: O=C(CCCCC1CCSS1)ON1C(=O)CCC1=O]

(L2; NHS-derivatized lipoic acid);

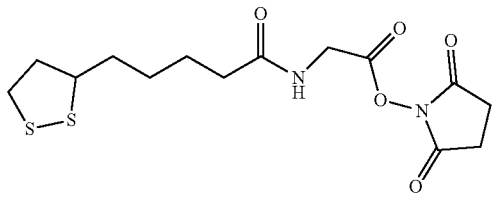 [SMILES: O=C(CCCCC1CCSS1)NCC(=O)ON1C(=O)CCC1=O]

(L3;Gly-OSu-NHS derivatized lipoic acid);

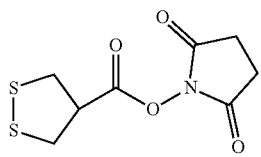 [SMILES: O=C(ON1C(=O)CCC1=O)C1CSSC1]

(L9; NHS-derivatized asparagusic acid); and,

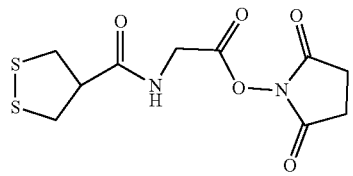 [SMILES: O=C(CNC(=O)C1CSSC1)ON1C(=O)CCC1=O]

(Gly-OSu derivativized asparagusic acid)

There are several methods of using the adhesive compositions in their various forms, both medical and non-medical, and the adhesive compositions can be used in a variety of conditions. In some embodiments, the adhesives are used in ambient conditions. In some embodiments, the adhesives are used in dry conditions. In some embodiments, the adhesives are used in wet conditions. In some embodiments, the adhesives are used underwater.

There are a variety of products that can be made from the adhesive compositions, and the products can be liquid, solid, or a combination of liquid and solid. In some embodiments, the adhesive compositions are liquid solutions including monomers that are precursors for polymerization to adhesive polymers. In some embodiments, the adhesive compositions are liquid solutions including monomers and oligomers that are precursors for polymerization to adhesive polymers. In some embodiments, the adhesive compositions are liquids that include monomers oligomers that are precursors for polymerization to adhesive polymers, and polymers that are the product of partial polymerization of the monomers, or monomers and oligomers. In some embodiments, adhesive compositions can be an combination of monomers, oligomers, and polymers, alone or in any combination. The adhesive composition products can also include any one or any combination of a component selected from the group consisting of a stabilizer, a terminator, the conjugate bases of the monomers, DMSO, an acid such as a Lewis acid or Bronsted acid, a cross-linker, and a reaction solvent.

The stability of the polymers in the adhesive compositions can be adjustable, in some embodiments. The choice of stabilizer moieties further allows to design the stability of the polymer, by choosing whether the stabilizer is needed at all for a desired use, and then adjusting the stability of the polymer for it's desired use by choosing a stabilizer moiety having a desired bond strength between the stabilizer and polymer. The same is true of the choice of terminator moieties by choosing whether to the terminator moiety is needed at at all for the desired use, and then further adjusting the stability of the polymer choosing a terminator moiety having a desired bond strength between the terminator and polymer.

The adhesive compositions can be used for any of a variety of medical uses. In some embodiments, the adhesive compositions can be used as a medical tissue adhesive, a medical tissue sealant, a medical tissue hemostat, and combinations thereof. In some embodiments, the adhesive compositions are biocompatible, biodegradable, therapeutic, and any combination thereof.

BRIEF DESCRIPTION OF THE FIGURES

FIGS. 1C1, 1C2, and 1C3 illustrate a solid adhesive composition of solid monomers and stabilizer(s), a liquid adhesive composition of a solution of the monomers and stabilizer(s) in a reaction solvent, and an adhesive composition in which the monomers and stabilizer(s) have been polymerized in an aqueous polymerization, in some embodiments. FIG. 1C1 illustrates a solid mixture of α-lipoic acid monomer (L1), an NHS-derivatized α-lipoic acid (L2) as a first stabilizer, and a Gly-OSu-derivatized α-lipoic acid (L3) as a second stabilizer. FIG. 1C2 illustrates the solid mixture in solution that has not yet polymerized and, as such, can be referred to as a "precursor" solution which can be obtained by dissolving the solid composition of FIG. 1C1 in pure ethanol, for example. FIG. 1C3 is the polymerized version of the either FIG. 1C1 or FIG. 1C2 that can be obtained by adding a polar protic solvent such as water, an aqueous solution of water and ethanol, perhaps along with DMSO and/or acid as a polymerization catalyst.

FIGS. 1D1, 1D2, and 1D3 illustrate a liquid adhesive composition containing polymers with monomers, the conjugate base of the monomers, and stabilizer(s); brushing of the liquid adhesive composition onto a substrate, and aqueous polymerization of the liquid adhesive composition on the substrate to create a sticky adhesive on the substrate, in some embodiments. FIG. 1D1 shows a liquid adhesive composition of α-lipoic acid monomer (L1), an NHS-derivatized α-lipoic acid (L2) as a first stabilizer, and the conjugate base of the α-lipoic acid monomer (L4) to help stabilize the "precursor" from an undesired polymerization. The precursor can be brushed onto a substrate which can be applied to a wet surface to polymerize as shown in FIG. 1D2, the aqueous polymerization that results from contact with a wet surface is shown in FIG. 1D3.

FIG. 2C illustrates that over 60% recovery efficiency was achieved within such a short interval, indicating an unexpectedly high chain mobility within the polymer network.

FIG. 2D is a frequency sweep measurement at a constant strain of 0.4% at 37° C., and FIG. 2E is an amplitude sweep at a constant frequency of 5 rad/s at a temperature of 37° C., in some embodiments. Without intending to be bound by any theory or mechanism of action, the data suggests that the polymer network has a lower crosslinking density, and it increases over time and provides higher stability of the network.

FIG. 3I shows the puncture, and FIG. 3J shows the successful patching as tested for air leaks with a soap water spray, in some embodiments. The p value was calculated with a student's t-test in Microsoft Excel (2 array, 2 tails, 2 type). * p>0.05,  p≤0.05, * p≤0.01.

FIG. 3K shows the puncture, and FIG. 3L shows the successful patching as tested for air leaks with a soap water spray, in some embodiments. The p value was calculated with a student's t-test in Microsoft Excel (2 array, 2 tails, 2 type). * p>0.05,  p≤0.05, * p≤0.01. The patched lung puncture was tested for air leaks with a soap and water spray and none were found.

FIGS. 4G-4J test the bacterial resistance of the adhesive compositions by illustrating a comparison of a control assay of *E. coli* growth in a culture plate to the *E. coli* growth on a solid adhesive patch and a culture plate coated with the in-situ synthesized poly(α-lipoic acid) polymer. As shown in FIG. 4G, the adhesive compositions serve very well as a bacterial barrier after 24 hours co-culture. FIG. 4H shows the presence of the cells in the control, whereas FIGS. 4I and 4J show how the presence of the cells is reduced on both the solid adhesive patch and the polymer coated culture plate due to the bacterial resistance properties of the adhesive composition.

FIGS. 5A, 5B1-B3, and 5C show the results of a test of the adhesive strength, recycling, and chemical profile of a pressure sensitive adhesive (PSA) produced from a poly(α-lipoic acid) polymer adhesive composition, in some embodiments. FIG. 5A compares peeling strength of the PSA against stainless steel (SS), high density polyethylene (HDPE), and polytetrafluoroethylene (PTFE) at dry and underwater conditions, showing the adhesion works almost as well underwater as when used in dry conditions, and that although the adhesion strength varies between substrates, the PSA did adhere to all of the substrates, where the adhesion strength order is generally SS>>HDPE>>PTFE. FIG. 5B1-B3 show a recycling sequence of the PSA.

DETAILED DESCRIPTION OF THE INVENTIONS

Figure 1A:
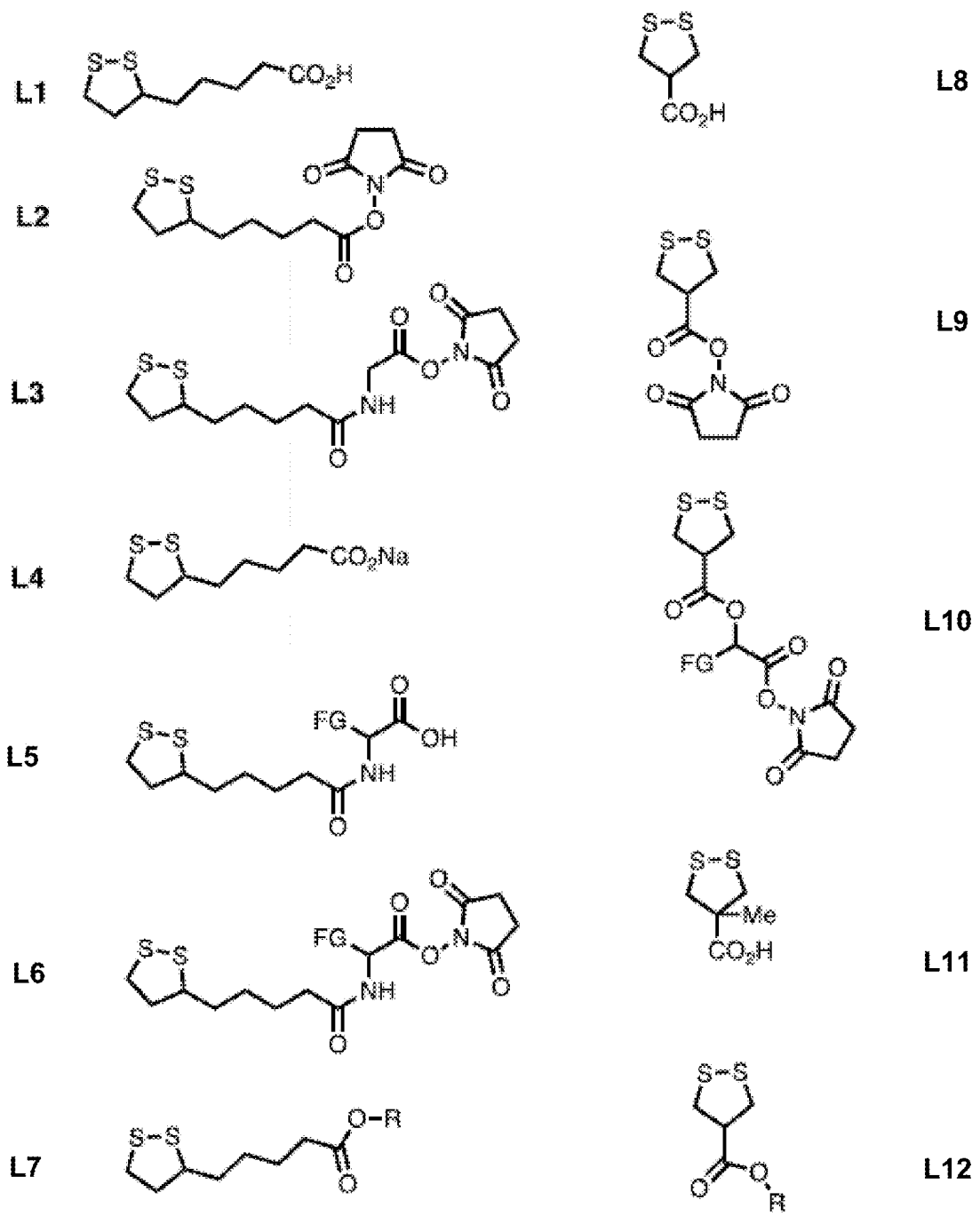
FIG. 1A illustrates examples of dithiolane monomers and stabilizers that can be used in the adhesive compositions, namely those made from α-lipoic acid and asparagusic acid, in some embodiments.
Figure 1B:
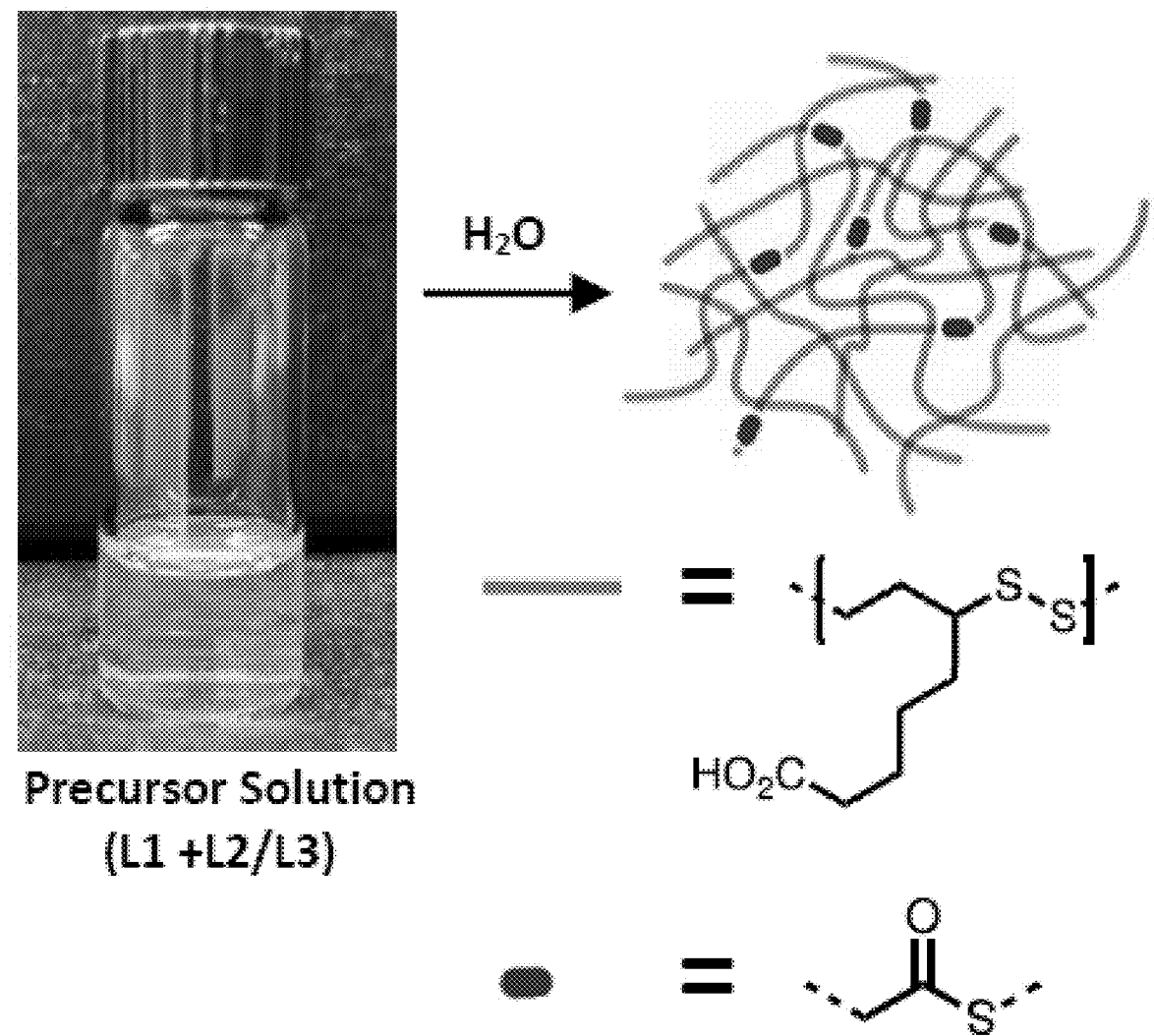
FIG. 1B illustrates the conversion of a liquid adhesive composition to a polydisulfide polymer, in some embodiments. The liquid adhesive contains α-lipoic acid monomer (L1), an NHS-derivatized α-lipoic acid (L2) as a first stabilizer, and a Gly-OSu-derivatized α-lipoic acid (L3) as a second stabilizer. The liquid adhesive composition can sometimes be referred to as a "precursor" solution because it is a composition that can form the poly(α-lipoic acid) polymer when water, a polar, protic solvent, is added to the composition. The polymer has a repeating disulfide unit as shown, with labile thioester bonds in the polymer.
Figure 1E:
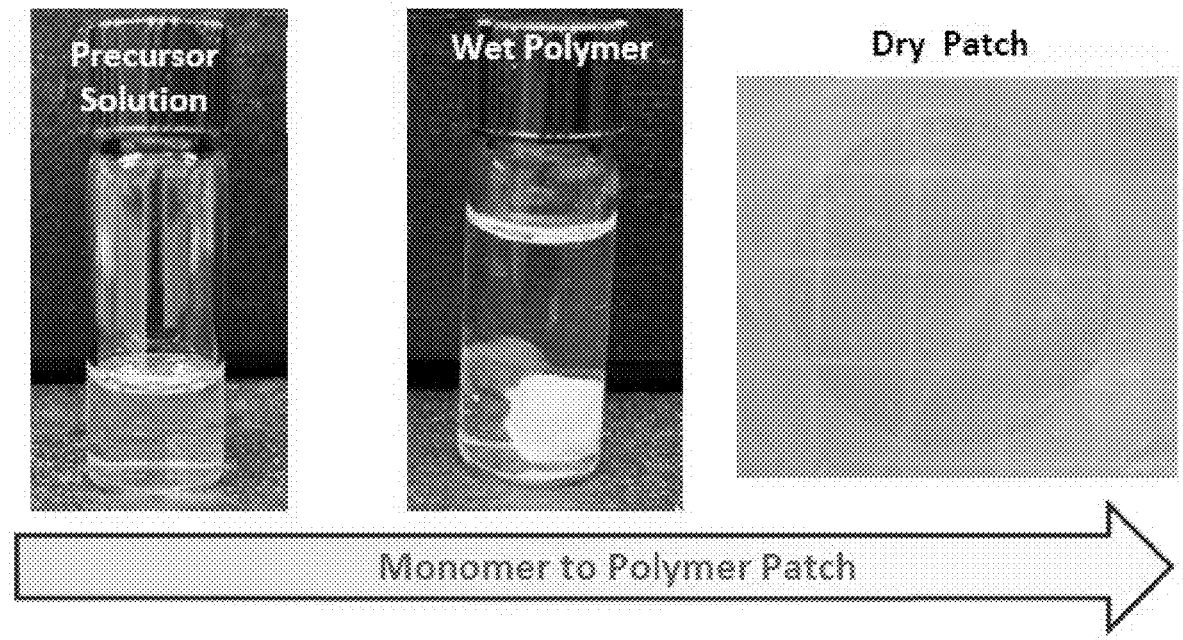
FIG. 1E illustrates the stepwise conversion of a liquid adhesive composition to a wet polymer that can be applied to a substrate, or be formed into a solid shape before or after polymerization, to create a solid article such as a solid adhesive patch, in some embodiments. The unpolymerized liquid adhesive composition is shown to polymerize to a wet polymer when water is added to the liquid adhesive "precursor" composition, and the wet polymer can be used to form the solid adhesive patch.
Figure 1F:
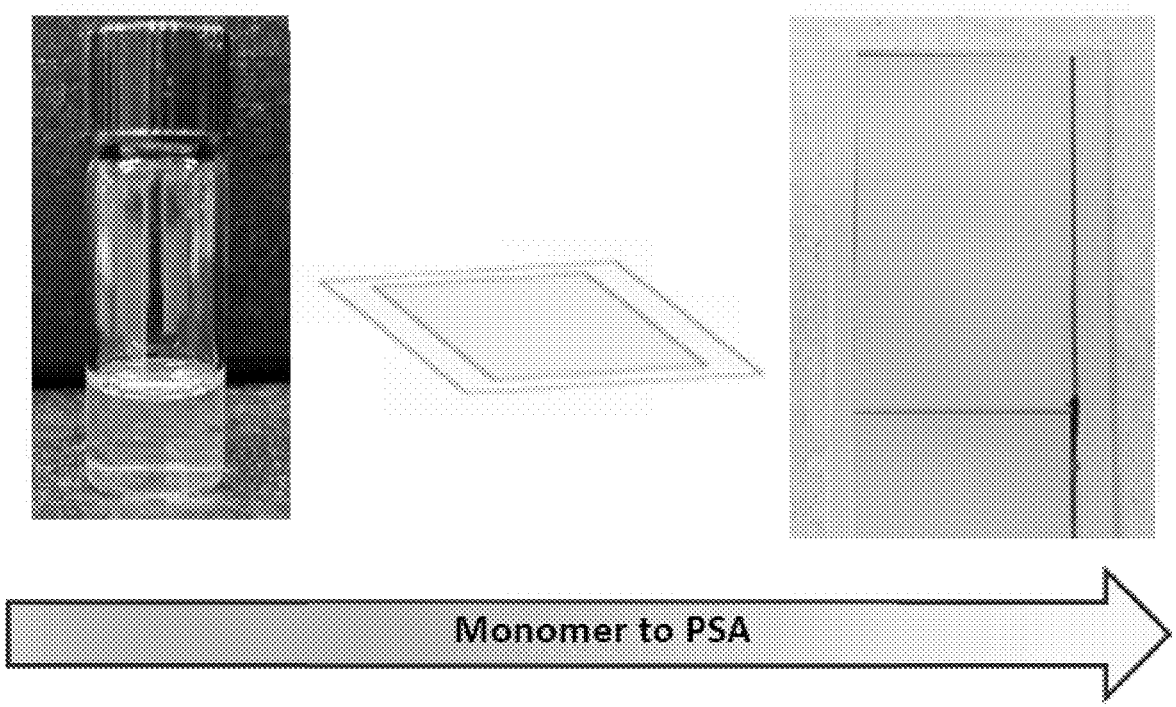
FIG. 1F illustrates the stepwise conversion of a liquid adhesive composition to a wet polymer that can be applied to a substrate as a pressure sensitive adhesive (PSA), in some embodiments. The unpolymerized liquid adhesive composition is polymerized, and the sticky polymer adhesive is added to a substrate as a PSA. A paper substrate with a strip of the PSA, for example, can be a sticky note in some embodiments.

The teachings provided herein include adhesive compositions for medical and non-medical use, the adhesive compositions made of cyclic disulfide monomers, oligomers of reactions between the cyclic disulfides, polymers of the cyclic disulfides, and any combination thereof. Methods of making and using the adhesive compositions are included for both medical and non-medical applications, and on any of a variety of substrates that include biological tissue; biomaterials, including synthetics and natural such as bone, wood, and cellulosics; metals and alloys; polymers, plastics, and rubbers; ceramics; composites; and, any combination of these materials. The adhesives can also adhere to substrates in any of a variety of environmental conditions that include ambient atmospheric conditions, wet conditions that include adhering materials underwater, and in a wide variety of temperatures and pressures, such as those temperatures and pressures found in medical environments, including in living tissue, as well as many residential, commercial, industrial, and manufacturing environments.

Many of the adhesive compositions taught herein have been tested using α-lipoic acid monomers which are a preferred monomer for many uses due to the properties of the monomers, as well as the properties of the poly(α-lipoic acid) polymers. Asparagusic acid monomers have many desired properties, as do the poly(asparagusic acid) polymers. Like α-lipoic acid, we developed a method of polymerizing stable forms of poly(asparagusic acid) and found that it had excellent mechanical properties and adhesion strength, some of which are superior to poly(α-lipoic acid) as well as a cost-effective production and closed-loop chemical recycling. An added benefit is that poly(asparagusic acid) (L8) is that, although it also depolymerizes on it's own, it depolymerizes more slowly than poly(α-lipoic acid) because it's cyclic ring has more strain and, although it can certainly be stabilized like the poly(α-lipoic acid), the stability of poly(asparagusic acid) without a stabilizer molecular is sufficient for many uses. Like poly(α-lipoic acid), poly(asparagusic acid) also readily depolymerizes into safe monomers and oligomers, the monomers having the therapeutic activities of interest.

Generally speaking, the adhesive compositions include cyclic disulfide monomer components that polymerize into a sticky polydisulfide polymers at the time of use; oligomers of the cyclic disulfide that polymerize into a sticky polydisulfide polymers at the time of use; polydisulfide polymers of the cyclic disulfide components ready for such use; solid adhesive products formed from such sticky polymers; any one or combination of those for additional polymerization before or during such uses; and, any combination thereof.

The polymerization of the cyclic disulfide monomer can occur in water; an aqueous solution; a water miscible solvent; a polar, protic solvent; thermally; and, any combination thereof. For purposes of efficiency, all solvents will be collective referred to as "reaction solvent". Ethanol, water, a combination of ethanol and water, any aqueous media such as saline or a buffer solution, and the like, are examples of polar, protic solvents. DMSO and DMF are examples of solvents miscible in water, and both are polar, aprotic solvents. Thermal polymerization can occur in a dried mixture of monomers, or a mixture of monomers in a reaction solvent. In some embodiments, the reaction solvents can be selected from the group of ethanol, DMSO, methanol, polyethylene glycol, glycerol, ionic liquids, vegetable oils, or any water-miscible organic solvents.

The polymerization of the cyclic disulfide monomer can occur in a reaction solvent to create a sticky polymer. In some embodiments, an electrophilic stabilizer can be added for stabilizing such sticky polymers and address the problem of depolymerization that happens in polymers created by the cyclic disulfide monomers. The depolymerization can render some polymers useless in applications that require at least a minimal amount of polymer stability that cannot be obtained without the addition of the stabilizer. In some embodiments, a terminator molecule is added for further stabilizing the polymer. In some embodiments, a Lewis acid or a Bronsted acid is added to increase the rate of polymerization. In some embodiments, dimethyl sulfoxide (DMSO) is added to increase the rate of the polymerization. In some embodiments, a Lewis acid or a Bronsted acid is addition with a catalytic amount of the DMSO to increase the rate of polymerization. In some embodiments, the conjugate base of a cyclic disulfide monomer is added to increase the stability of the adhesive compositions as a whole before use of the compositions as intended. And, in some embodiments, a crosslinker is added to strengthen polymeric adhesives formed from the adhesive compositions through covalent bond or non-covalent bonds made between the crosslinker and the adhesive polymers. The crosslinker can include, for example, a monomer, an oligomer, a polymer, and conjugate bases of monomers used in the polymerization; metal ions, such as multivalent metal ions including divalent metal ions such as Ca++; transition and alkali earth metal salts; and, metal salts of cyclic 1,2-dithiolane derivatives; and, combinations thereof; wherein, the crosslinkers are added to further strengthen the compositions.

The Compositions
The Cyclic Disulfide Monomers

The cyclic disulfide monomers polymerize to relieve the ring strain. In some embodiments, the cyclic disulfide monomers are a plurality of polymerizable monomers selected from the group consisting of substituted cyclic disulfide molecules having from 2 to 4 C atoms in a cyclic ring with a disulfide bond, the substituted cyclic disulfide molecules functional to polymerize through a ring-opening reaction in a polar, protic solvent to form a polymer having a first active thiol end and a second active thiol end; and,
a plurality of repeating units having a substituted dithioalkyl structure from the ring opening reaction as follows

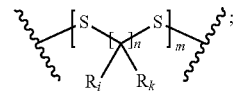

wherein,
n is an integer ranging from 2 to 4;
each $R_i$ and $R_k$ is independently selected from the group consisting of H; alkyl, cycloalkyl, alkenyl, alkynyl, and aryl groups having from 1-8 carbons, 1-6 carbons, 1-4 carbons, 1-3 carbons, 2 carbons, or 1 carbon; hydroxylated alkyl, cycloalkyl, alkenyl, alkynyl, and aryl groups having from 1-8 carbons, 1-6 carbons, 1-4 carbons, 1-3 carbons, 2 carbons, or 1 carbon; and, carboxylated alkyl, cycloalkyl, alkenyl, alkynyl, and aryl groups having from 1-8 carbons, 1-6 carbons, 1-4 carbons, 1-3 carbons, 2 carbons, or 1 carbon; wherein, i and k are integers and at least one $R_i$ or $R_k$ in each repeating unit includes a carbonyl functionality;
and,
m is an integer selected to match the desired molecular weight of the polymer.

The molecular weight of the polymer can be any desired molecular weight, selected by the skilled artisan to obtain desired chemical and physical behavior of the polymer for it's intended uses. The molecular weight can be selected reflect the desired length of the polymer, so the molecular weight for a given length can vary depending on the size of the desired substituents of the polymer, and the degree of branching of the polymer, for example. In some embodiments, the molecular weight of the polymer can range from 1000 Daltons to 100,000 Dalton, from 5000 Daltons to 500,000 Daltons, from 6000 Daltons to 400,000 Daltons, from 7000 Daltons to 300,000 Daltons, from 8000 Daltons to 200,000 Daltons, from 9000 Daltons to 150,000 Daltons, from 10,000 Daltons to 100,000 Daltons, from 20,000 Daltons to 100,000 Daltons, from 30,000 Daltons to 100,000 Daltons, from 40,000 Daltons to 100,000 Daltons, from 10,000 Daltons to 40,000 Daltons, from 15,000 Daltons to 40,000 Daltons, from 20,000 Daltons to 40,000 Daltons, or any molecular weight or range of molecular weights therein in increments of 500 Daltons.

In some embodiments, the cyclic disulfide monomer can be, for example, a dithietane (2 carbons in the ring), a dithiolane (3 carbons in the ring), a dithiane (4 carbons in the ring), and any substituted form thereof or combination thereof. In some embodiments, the cyclic disulfide can be 1,2-dithietane, and substituted forms thereof; 1,2-dithiolane, and substituted forms thereof; 1,2-dithiane, and substituted forms thereof; and any combinations thereof.

The cyclic disulfide monomer can substituted. In some embodiments, the plurality of substituted cyclic disulfide molecules include a substituted 1,2-dithietane, and the repeating unit includes a substituted 1,2-dithioethyl structure. In some embodiments, the plurality of substituted cyclic disulfide molecules is substituted 1,2-dithiolane, and the repeating unit is a substituted 1,3-dithioethyl structure. In some embodiments, the plurality of substituted cyclic disulfide molecules is a substituted 1,2-dithiane, and the repeating unit is a substituted 1,4-dithioethyl structure.

In some embodiments, the cyclic disulfide monomer can be a dithiolane monomer having the following general structure:

and, the R-group can be selected from the group consisting of the following, in some embodiments:

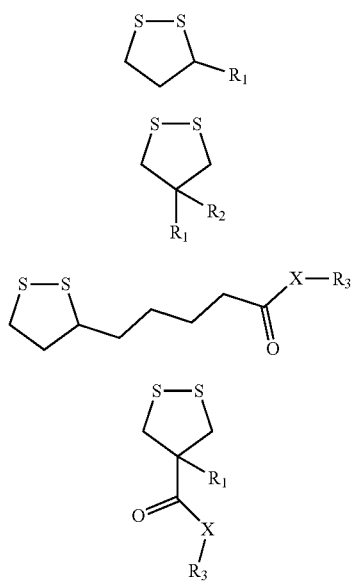

wherein, $R_1$ can be selected from the group consisting of H; a linear, branched or cyclic saturated or unsaturated C1-C8 alkyl group, C1-C6 alkyl group, C1-C4 alkyl group, C1-C3 alkyl group, C2 alkyl group, or C1 alkyl group; a linear, branched or cyclic saturated or unsaturated C1-C8 alkyl group with a terminal carbonyl group, including smaller versions thereof that include, C1-C6 alkyl group, C1-C4 alkyl group, C1-C3 alkyl group, C2 alkyl group, or C1 alkyl group; a linear, branched or cyclic saturated or unsaturated C1-C8 with terminal mono or dicarboxylic acid, including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated C1-C8 with terminal mono or dicarboxylic salt, where the counter ion of carboxylate includes, but is not limited to, alkali metal ions (Na, K, Li), alkali earth metal ions (Ca, Mg), transition metal ions (Zn, Fe, V), including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated C1-C8 with terminal mono or dicarboxylic salt, where the counter ion of carboxylate includes, but is not limited to, an organic salt such as ammonium, phosphonium, imidazolium, choline, etc., including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated C1-C8 with mono or diester group, including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated C1-C8 with mono or diester group with an aromatic substituent; a linear, branched or cyclic saturated or unsaturated C1-C8 containing a mono or diamide group, including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated C1-C10 containing a mono or diamide and terminal carboxylic acid, including smaller versions thereof that include a C1-C8 alkyl group, a C1-C6 alkyl group, a C1-C4 alkyl group, a C1-C3 alkyl group, a C2 alkyl group, or a C1 alkyl group; a linear, branched or cyclic saturated or unsaturated C1-C8 containing a mono or thioester group; $—(CH_2)_4CO_2H$; $—CO_2H$; a linear, branched or cyclic saturated or unsaturated C1-C10 containing one or more cyclic 1,2-dithiolane derivatives; an organic small or macromolecule containing one or more cyclic 1,2-dithiolane derivatives; and combinations thereof;

$R_2$ can be selected from the group consisting of H; a linear, branched or cyclic saturated or unsaturated C1-C8 group, including smaller versions thereof that include a C1-C6 alkyl group, a C1-C4 alkyl group, a C1-C3 alkyl group, a C2 alkyl group, or a C1 alkyl group; and combinations thereof;

$R_3$ can be selected from the group consisting of H; a linear, branched or cyclic saturated or unsaturated C1-C8 group, including smaller versions thereof that include a C1-C6 alkyl group, a C1-C4 alkyl group, a C1-C3 alkyl group, a C2 alkyl group, or a C1 alkyl group; an aromatic or heterocyclic aromatic group; an alpha or beta amino acid; an alpha or beta peptide; dopamine; a monosaccharide, disaccharide or oligosaccharide; 1,4-dihydrophenonthrolin-4-one-3-carboxylic acid; a therapeutic molecule having a molecular weight of no more than 40,000 Daltons, 30,000 Daltons, 20,000 Daltons, 10,000 Daltons, 5000 Daltons, 3000 Daltons, 2000 Daltons, 1000 Daltons, 500 Daltons, or any range therein in increments of 100 Daltons. Any therapeutic molecule can be used, and in some embodiments, the therapeutic molecule can be selected from the group consisting of an antioxidant, an anti-inflammatory, an analgesic, an antiproliferant, an immunomodulator, an antimicrobial, an antibacterial, an antifungal, an antiviral, or any combination thereof; and, X can be selected from the group consisting of O, N, and S.

The cyclic disulfide monomer can substituted. In some embodiments, the plurality of substituted cyclic disulfide molecules include a substituted 1,2-dithietane, and the repeating unit includes a substituted 1,2-dithioethyl structure. In some embodiments, the plurality of substituted cyclic disulfide molecules is substituted 1,2-dithiolane, and the repeating unit is a substituted 1,3-dithioethyl structure. In some embodiments, the plurality of substituted cyclic disulfide molecules is a substituted 1,2-dithiane, and the repeating unit is a substituted 1,4-dithioethyl structure.

The cyclic disulfide monomer in an adhesive composition is the reactant that forms the repeating units in the polymer, and the polymer can be defined, at least in part, by a description of the repeating units. In some embodiments, the repeating unit is a substituted 1,3-dithiopropyl structure as follows:

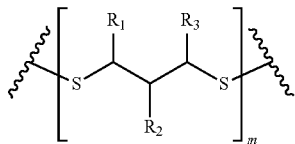

wherein,
m is an integer selected to match the desired molecular weight of the polymer;
$R_i$ includes $R_1$, $R_2$, and $R_3$; and,
each $R_k$ is H;
and, each stabilizer molecule includes the substituted 1,3-dithiopropyl structure.

In some embodiments, the repeating unit has a substituted 1,3-dithiopropyl structure as follows

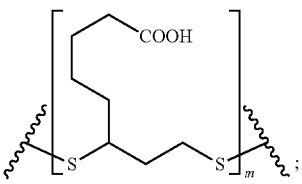

wherein,
m is an integer selected to match the desired molecular weight of the polymer;
$R_1$ is a pentanoic acid group, and $R_2$ and $R_3$ are each H;
and, each stabilizer molecule includes the substituted 1,3-dithiopropyl structure, wherein $R_1$ is a pentanoic acid group, and $R_2$ and $R_3$ are each H.

In some embodiments, the polymer further includes a plurality of terminator molecules selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality, the terminator molecules functioning to form a second labile bond with the second active thiol end of the polymer to further stabilize the polymer.

In some embodiments, the repeating unit has a substituted 1,3-dithiopropyl structure

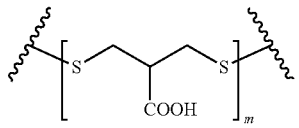

wherein,
m is an integer selected to match the desired molecular weight of the polymer;
$R_1$ and $R_3$ are H, and $R_2$ is a carboxylic acid group;
and, each stabilizer molecule includes the substituted 1,3-dithiopropyl structure, wherein $R_1$ and $R_3$ are H and $R_2$ is a carboxylic acid group.

Reaction Solvents

The monomers polymerize to form an adhesive polymer upon contact with a reaction solvent, such as water, an aqueous solution, a polar protic solvent, or any water miscible solvent such as DMSO and DMF, which are polar aprotic solvents (all referred to herein as "reaction solvent"). The reaction solvent can be, for example, an alcohol, water, a mixture of an alcohol and water, pure ethanol, pure water, a mixture of ethanol and water, a buffer solution, dimethylsulfoxide (DMSO), dimethylformamide (DMF) polyethylene glycol (PEG), glycerol, ionic liquids such as saline, a vegetable oil, and the like, and combinations thereof.

In some embodiments, the reaction solvent can also be a biological fluid, or a biologic compatible fluid, for ease of direct use in medical applications, for example, blood, urine, sweat, amniotic fluid, spinal fluid, serum, plasma, isotonic saline, and cell culture media.

In some embodiments, buffers can also be used, either alone or in combination with any of the reaction solvents, the buffers including, for example, Phosphate-buffered saline (PBS), Dulbecco's Phosphate-Buffered Saline (DPBS), N-(2-Hydroxyethyl)piperazine-N'-(2-ethanesulfonic acid) (HEPES), 2-(N-morpholino)ethanesulfonic acid (MES), 2-(bis(2-hydroxyethyl)amino)ethane sulfonic acid (BES), 3-(N-morpholino)propanesulfonic acid (MOPS), 3-Morpholino-2-hydroxypropanesulfonic acid (MOPSO), Tricine, Bicine, [tris(hydroxymethyl)methylamino]propanesulfonic acid (TAPS), and the like, and combinations thereof.

Stabilizers

There are at least two active thiol ends in the adhesive polymers taught herein, a first active thiol end, and a second active thiol end, where "first" and "second" only refer to two different positions, and do not suggest an order of reaction or relative reactivity.

The stabilizers are electrophiles that bond to the first active thiol groups at an end of the polydisulfide polymers. It should be appreciated that, in some embodiments, the terms "stabilizer", "stabilizing molecule", "stabilizer group", "stabilizing molecule", and "stabilizing group", and the like, can be used interchangeably, and refers to a chemical moiety that can bond to the first active thiol end.

In some embodiments, a plurality of stabilizer molecules can be configured to stabilize the first active thiol end of the polymer. The plurality of stabilizer molecules can include the substituted cyclic disulfide molecules derivatized to have a functional group that forms a first labile bond with the first active thiol end, the first labile bond selected from the group consisting of a thioester bond, a thiocarbamate bond, and a thioether bond.

It should be appreciated that term "labile" is a term in the art of chemistry. In some embodiments, "labile" can refer to a bond that is cleavable by a biological mechanism inside the human body, such that a labile bond is one that adds to the biodegradable characteristic of an adhesive composition, or polymer, taught herein. In some embodiments, "labile" can refer to a bond that is cleavable by any chemical means that one of skill may use in a recycling process, such that the cleavage of the labile bond results in monomers that are the same or similar to, or substantially similar to, the original monomers reacted to form an original or regenerated adhesive composition or polymer taught herein, where "regenerated" can be used to refer to a polymer or material made from recycled monomers, and the term "substantially" and "substantially similar" can refer to a term of degree, where something that is "substantially the same" would be the same for all practical purposes to the ordinary skilled artisan upon a first consideration without further any further consideration needed. A molecule or material that appears "similar" to an ordinary skilled artisan may be considered to possibly have the desired function or activity but may need a second consideration or testing. A "substantially similar" molecule, on the other hand, would obviously have the desired function or activity in the view of the skilled artisan upon the first consideration. In some embodiments, the term "labile" can refer to a degradation of the adhesive composition or monomer from ambient environment conditions present in nature including the presence of water, heat, UV energy, bacteria, fungi, molds, enzymes, acids, bases, and the like, and any combination thereof. In some embodiments, the labile nature of bonds is a desired feature of biodegradation. In some embodiments, the labile nature of bonds is a desired feature of environmental hygiene and/or safety. In some embodiments, the labile nature of bonds is a desired feature for bioelimination from a subject through ordinary filtration and excretion by the body. In some embodiments, the labile nature of bonds is a desired feature for recycling.

The monomers used in the polymerization form the repeating units of the polymer. In some embodiments, the monomers and the stabilizer molecules are the same or substantially the same chemical moieties following a depolymerization of the polymer. This can be beneficial in a recycling process of the polymeric material because the monomer and the stabilizer are the same or similar molecules following depolymerization of the polymer. It should be appreciated that to be "the same" can be construed to mean identical, and so the terms "substantially" or "similar" are used to reflect the understanding that the skilled artisan would see a significant difference between the chemical moieties in a mixture. To substantially the same, or similar, for example, the chemical moieties (i) may only differ in structure in a way that is easily converted to be identical to the original monomer used in the reaction; (ii) may only differ in structure in a way that does not appreciably affect the repolymerization of the monomers to a regenerated material to have a desired function; (iii) may only differ in structure in a way that does not appreciably affect the repolymerization of the monomers to a regenerated material to have a desired biocompatibility; (iv) may only differ in structure in a way that does not appreciably affect the repolymerization of the monomers to a regenerated material to have a desired toxicity level; and/or (v) may have a desired yield in a repolymerization, regardless of whether a desired function is obtained in every repolymerization.

In some embodiments, the stabilizers include R—OH, R—NH, R—SH, R-carbonyls, R-thiocarbonyls, R-carboxyls, R-thiocarboxyls, R-esters, R-anhydrides, R-quinones, R-thioquinones, R-isocyanates, R-diisocyanates, R-imidazoles, and the like, where R can be any alkyl, cycloalkyl, alkenyl, alkynyl, and aryl groups having from 1-14 carbons; hydroxylated alkyl, cycloalkyl, alkenyl, alkynyl, and aryl groups having from 1-14 carbons; and, carboxylated alkyl, cycloalkyl, alkenyl, alkynyl, and aryl groups having from 1-14 carbons. In these embodiments, the stabilizers can include carbonyl imidazoles, N-hydroxy succinimide (NHS) esters, N-hydroxysulfosuccinimide esters, N-hydroxy phthalimide esters, N-hydroxy succinimide (NHS) esters of lipoic acid, and N-hydroxy succinimide (NHS) esters of asparagusic acid. The stabilizers can be configured for shape, size, and chemical activity, to control reactivity and function as desired, for example, to alter the strength of the labile bond with the active thiol end group, the strength of the stabilizer as a nucleophile, the strength of the stabilizer as an electrophile, steric hindrance, rate of reactivity, rate of polymerization, and the like. It should be appreciated that, in some embodiments, the number of carbons in any of the stabilizers can be configured by the skilled artisan to range from 1-14, 1-12, 1-10, 1-8, 1-7, 1-6, 1-5, 1-4, 1-3, 1-2, 1, or any amount or range of carbons therein.

In some embodiments, the stabilizers can be selected from the group consisting of

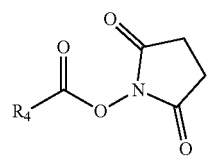
(V)

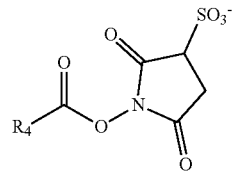
(VI)

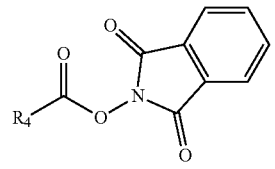
(VII)

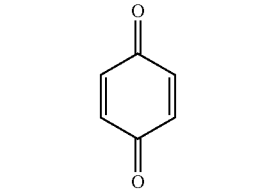
(VIII)

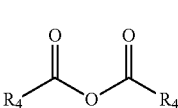
(IX)

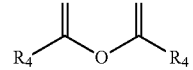
(X)

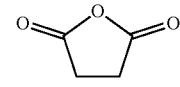
(XI)

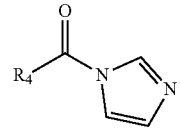
(XII)

Namely, N-hydroxy succinimide (NHS) esters (V), N-hydroxysulfosuccinimide esters (VI), N-hydroxy phthalimide esters (VII), oxidized polyphenols, quinones (VIII), isocyanates (IX), linear or cyclic or poly anhydrides (X, XI), and carbonyl imidazoles (XII);

wherein, $R_4$ can be selected from the group consisting of an alkyl dithiolane; a poly dithiolane, OH; a linear, branched or cyclic saturated or unsaturated C1-C8 group, including smaller versions thereof that include a C1-C6 alkyl group, a C1-C4 alkyl group, a C1-C3 alkyl group, a C2 alkyl group, or a C1 alkyl group; a linear, branched or cyclic saturated or unsaturated macromolecules; an aromatic or heterocyclic aromatic group; and alpha or beta amino acid; an alpha or beta peptide; dopamine; a monosaccharide, disaccharide, oligosaccharide or polysaccharide; 1,4-dihydrophenonthrolin-4-one-3-carboxylic acid; polyethylene glycol; and, a therapeutic molecule having a molecular weight of no more than 40,000 Daltons, 30,000 Daltons, 20,000 Daltons, 10,000 Daltons, 5000 Daltons, 3000 Daltons, 2000 Daltons, 1000 Daltons, 500 Daltons, or any range therein in increments of 100 Daltons. Any therapeutic molecule can be used, and in some embodiments, the therapeutic molecule can be selected from the group consisting of an antioxidant, an anti-inflammatory, an analgesic, an antiproliferant, an immunomodulator, an antimicrobial, an antibacterial, an antifungal, an antiviral, or any combination thereof.

Suprisingly, we found that the addition of the electrophilic stabilizer increased the rate of polymerization substantially, and often dramatically, in addition to the function of addressing the problem of depolymerization. It was found that, during water-catalyzed polymerization of dithiolane monomer, for example, we created new capabilities in adhesion through our dithiolane adhesive compositions. We observed a surprisingly rapid transformation of a liquid adhesive precursor into a solid adhesive, for example, which is particularly useful in adhering wet surfaces. Valuable uses include adhering human or animal tissues, as they contribute sufficient water to catalyze an in-situ polymerization of dithiolane monomers upon contact with the wet tissue. As such, the adhesive compositions taught herein, such as the dithiolanes compositions including stabilizer, were particularly useful in adhering devices to tissues, adhering tissues to tissues, and closing puncture wounds in tissues. It was also discovered that the use of NHS esters, NHS being a known electrophile, can increase the formation of covalent bonds with tissue surfaces in the adhesive compositions.

The stability of the polymers in the adhesive compositions can be adjustable, in some embodiments. The choice of stabilizer moieties further allows to design the stability of the polymer, by choosing whether the stabilizer is needed at all for a desired use, and then adjusting the stability of the polymer for it's desired use by choosing a stabilizer moiety having a desired bond strength between the stabilizer and polymer.

The same is true of the choice of terminator moieties by choosing whether to the terminator moiety is needed at at all for the desired use, and then further adjusting the stability of the polymer choosing a terminator moiety having a desired bond strength between the terminator and polymer.

Terminators

As noted, there are at least two active thiol ends in the adhesive polymers taught herein, a first active thiol end, and a second active thiol end. The stabilizer bonds to a first active thiol end to help stabilizer the polymer from depolymerization, and a terminator can be used to bond with the second active thiol end. It should be appreciated that, in some embodiments, the term "terminator", "terminator molecule", "terminating molecule", "terminator group", "terminating group", and the like, can be used interchangeably, and refers to the a chemical moiety that can bond to the second active thiol end. In some embodiments, the bonding of the terminator to the second active thiol group occurs after the bonding of the stabilizer to the first active thiol group. In some embodiments, the stabilizer and the terminator are added concurrently to a reaction mixture and, in some embodiments, the stabilizer and the terminator are added sequentially to the reaction mixture. In some embodiments, the stabilizer is added to a reaction mixture first, and the terminator is added to the reaction mixture second.

In some embodiments, the plurality of terminator molecules having a functional group that forms a second labile bond with the second active thiol end of the polymer. In some embodiments, each of the plurality of terminator molecules is selected from the group consisting of R'OH, R'CO2H, and R'SH, where R' is an alkyl, cycloalkyl, alkenyl, cycloalkenyl, alkynyl, cycloalkynyl, an aryl group having from 1-8 carbons, including smaller versions thereof that include a C1-C6 alkyl group, a C1-C4 alkyl group, a C1-C3 alkyl group, a C2 alkyl group, or a C1 alkyl group; and, the second labile bond is selected from the group consisting of thioethers, thioesters, and disulfides.

In some embodiments, the plurality of terminator molecules is selected from the group consisting of alkanols having from 1-8 carbons, alkanoic acids having from 1-8 carbons, and alkylthiols having from 1-8 carbons, and the second labile bond is selected from the group consisting of thioethers, thioesters, and disulfides. Each of these embodiments can include smaller versions thereof that include, for example, a C1-C6 alkyl group, a C1-C4 alkyl group, a C1-C3 alkyl group, a C2 alkyl group, or a C1 alkyl group.

In some embodiments, the plurality of terminator molecules is selected from the group consisting of glycerol, lactic acid, glycolic acid, and citric acid, and any combination thereof.

In some embodiments, the plurality of terminator molecules are biocompatible alcohols, such as those with low acute toxicities. Examples of such biocompatible alcohols include ethanol, 1-propanol, 1-butanol, isobutanol, xylitol, erythritol, sorbitol, and malitol.

In some embodiments, the plurality of terminator molecules is selected from the group consisting of ethanol, a substituted 1,2-dithietane with a hydroxyl functionality, a substituted 1,2-dithiolane with a hydroxyl functionality, and a substituted 1,2-dithiane with a hydroxyl functionality.

Acids

As noted, the polymerization of the monomers into the polymers can be accelerated by adding an acid to the reaction mixture. Any suitable acid can be selected used by the skilled artisan. Examples of desirable acids that can be used include a varity of organic acids, inorganic Bronsted acids, and Lewis acids.

In some embodiments, the acid is a Bronsted acid and can include HCl, $H_2SO_4$, $HNO_3$, trifluoroacetic acid, fluoroacetic acid, trichloroacetic acid, acetic acid, citric acid, succinic acid, maleic acid, tartaric acid, gluconic acid, lactic acid, ascorbic acid, limononic acid, toluene sulfonic acid etc.

In some embodiments, the acid is a Lewis acid and can include $BCl_3$, $AlCl_3$, $BF_3$, $I_2$, $Cl_2$, $ICl$, $Br_2$, transition, alkali earth metal salts, etc.

The Polymers

The adhesive compositions taught above include a teachings of the polymers that are created, and it should be appreciated that the instant technology includes at least (i) the adhesive compositions that are used to make the polymers; (ii) the monomers, oligomers, and polymers in those compositions; (iii) the products of those compositions, including liquids, sprays, solid formed articles, and free-flowing powders; and, the methods of (iv) making and (v)

using the adhesive compositions, the polymers, the liquids, the sprays, the powders, and the solid formed articles.

The polymers include medical and non-medical polymers, both recyclable and non-recylable. In some embodiments, the polymers include the polymers taught above.

In some embodiments, the polymer is stabilized with a stabilizer as taught above. In some embodiments, the polymer is stabilized with both a stabilizer and terminator as taught above. In some embodiments, the polymer is recyclable. In some embodiments, the polymer is recyclable with fewer process steps because the stabilizer is the same as, or substantially similar to, the monomer used in the polymerization. In some embodiments, the polymer is recyclable with fewer process steps because the stabilizer is the same as, or substantially similar to, the monomer used in the polymerization, and the terminator is a solvent molecule used in the polymerization process. In some embodiments, the polymer is recyclable with fewer process steps because the stabilizer is the same as, or substantially similar to, the monomer used in the polymerization, and the terminator is a non-toxic, or relatively non-toxic solvent molecule used in the polymerization process. As such, the instant technology includes the stabilized and recyclable polydisulfide polymers as taught herein.

In some embodiments, the polymer is stable and recyclable and has the following structure:

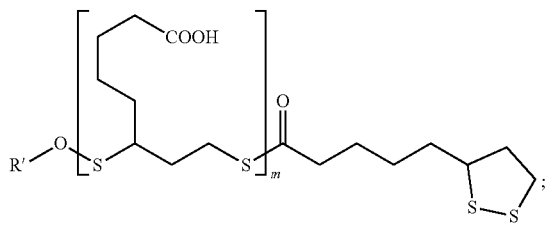

wherein, m is an integer selected to match the desired molecular weight of the polymer; and, R' is an alkyl, cycloalkyl, alkenyl, cycloalkenyl, alkynyl, cycloalkynyl, or aryl group having from 1-8 carbons, 1-6 carbons, 1-4 carbons, 1-3 carbons, 2 carbons, or 1 carbon. In some embodiments R' and R" have the same structure as the cyclic disulfide monomer used to form the polymer. In some embodiments, R' can be an alkyl group, such as an ethyl group.

In some embodiments, the polymer is stable and recyclable and has the following structure:

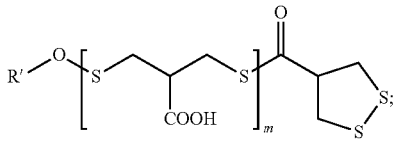

wherein, m is an integer selected to match the desired molecular weight of the polymer; and, R' is an alkyl, cycloalkyl, alkenyl, cycloalkenyl, alkynyl, cycloalkynyl, or aryl group having from 1-8 carbons, 1-6 carbons, 1-4 carbons, 1-3 carbons, 2 carbons, or 1 carbon. In some embodiments R' and R" have the same structure as the cyclic disulfide monomer used to form the polymer. In some embodiments, R' can be an alkyl group, such as an ethyl group.

The mechanical properties of the polymers taught herein can be increased through branching of the polymers. As such, the polymers taught herein include branched forms. For example, in some embodiments, the polymer is a stabilized and recyclable polydisulfide polymer. In these embodiments, the polymer can have a repeating unit with a substituted dithioalkyl structure as follows:

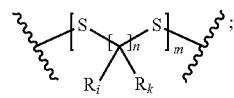

wherein, n is an integer ranging from 2 to 4;

each $R_i$ and $R_k$ is independently selected from the group consisting of H; alkyl, cycloalkyl, alkenyl, alkynyl, and aryl groups having from 1-8 carbons, 1-6 carbons, 1-4 carbons, 1-3 carbons, 2 carbons, or 1 carbon; hydroxylated alkyl, cycloalkyl, alkenyl, alkynyl, and aryl groups having from 1-8 carbons, 1-6 carbons, 1-4 carbons, 1-3 carbons, 2 carbons, or 1 carbon; and, carboxylated alkyl, cycloalkyl, alkenyl, alkynyl, and aryl groups having from 1-8 carbons, 1-6 carbons, 1-4 carbons, 1-3 carbons, 2 carbons, or 1 carbon; wherein, i and k are integers and at least one $R_i$ or $R_k$ in each repeating unit includes a carbonyl functionality;

m is an integer selected to match the desired molecular weight of the polymer;

In these embodiments, the stabilized and recyclable polydisulfide polymer can further have a first active thiol end and a second active thiol end; and, a plurality of stabilizer molecules. The plurality of stabilizer molecules are configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioester bond. And, in these embodiments, the repeating units and the stabilizer molecules can be the same, or substantially the same, chemical moieties following a degradation of the polymer during a recycling of the polymer. When the repeating units and the stabilizer molecules are the same, or substantially the same, chemical moieties following a degradation of the polymer during a recycling of the polymer, the recycling is an easier and more cost-effective commercial process.

Also, such a polymer can be branched to increase it's mechanical strength through added features that can include, perhaps, the addition of physical entanglement. In such embodiments, for example, the polymer can be branched from at least one of $R_i$ or $R_k$ in a first dithioalkyl repeating unit, the at least one $R_i$ or $R_k$ including a carbonyl functionality in a thioester bond with a second dithioalkyl repeating unit. And, in these embodiments, the terminator molecules taught above can be added to further stabilize the polymer from depolymerization.

In some embodiments, the stabilized and recyclable polydisulfide polymer can include the following branched structure

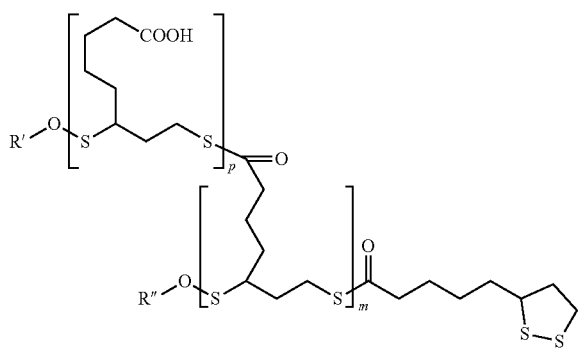

wherein,
- m is an integer selected to match the desired molecular weight of the polymer;
- p is an integer; and,
- R' and R" are each independently selected from a group consisting of an alkyl, cycloalkyl, alkenyl, cycloalkenyl, alkynyl, cycloalkynyl, or aryl group having from 1-8 carbons, 1-6 carbons, 1-4 carbons, 1-3 carbons, 2 carbons, or 1 carbon. In some embodiments R' and R" have the same structure as the cyclic disulfide monomer used to form the polymer. In some embodiments, R' and R" are alkyl groups, such as ethyl groups.

In some embodiments, the stabilized and recyclable polydisulfide polymer can include the following branched structure

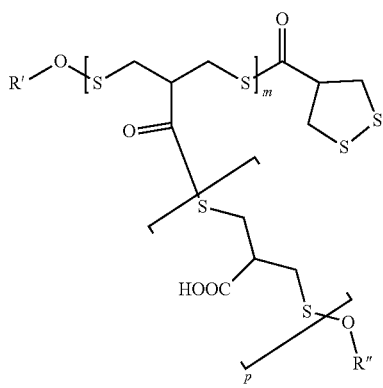

wherein,
- m is an integer selected to match the desired molecular weight of the polymer;
- p is an integer; and,
- R' and R" are each independently selected from a group consisting of an alkyl, cycloalkyl, alkenyl, cycloalkenyl, alkynyl, cycloalkynyl, or aryl group having from 1-8 carbons, 1-6 carbons, 1-4 carbons, 1-3 carbons, 2 carbons, or 1 carbon. In some embodiments R' and R" have the same structure as the cyclic disulfide monomer used to form the polymer. In some embodiments, R' and R" are alkyl groups, such as ethyl groups.

Methods of Making and Using the Adhesive Compositions

The adhesive compositions can be made in several ways, and they can be used in several ways whether the uses are medical or non-medical. For example, the methods can include placing cyclic disulfide monomers in a polar, protic reaction solvent taught herein; placing cyclic disulfide monomers in a reaction solvent with stabilizer molecules taught herein; and, placing cyclic disulfide monomers in the reaction solvent with the stabilizer molecules and terminator molecules taught herein. In each of these methods of making the adhesive compositions, acid and/or DMSO can be added to speed the rate of reaction, and a conjugate base of the monomers can be added to stabilize the composition. The adhesive compositions can also be dry, in which the polymerization occurs by contacting the dry compositions with water at the target site of the desired adhesion. The adhesive compositions can include precursor polymer, in which the polymer was formed and included as part of the adhesive composition, and polymerization is again initiated with water at the target site of the desired adhesion. The adhesive compositions can formed solid adhesive articles, including a solid adhesive patch, film, or membrane, and the solid adhesive article can be delivered to the site of adhesion with or without including a liquid, spray, or powder form of the adhesive composition for reaction with water at the target site of the desired adhesion. These and other methods are taught herein.

In some embodiments, the methods include obtaining a plurality of substituted cyclic disulfide molecules having from 2 to 4 C atoms in a cyclic ring with a disulfide bond, the substituted cyclic disulfide molecules functional to polymerize through a ring-opening reaction in polar, protic solvent to form a polymer having
- a first active thiol end and a second active thiol end; and,
- a repeating unit having a substituted dithioalkyl structure as follows

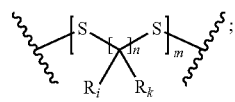

wherein,
- n is an integer ranging from 2 to 4;
- each $R_i$ and $R_k$ is independently selected from the group consisting of H; alkyl, cycloalkyl, alkenyl, alkynyl, and aryl groups having from 1-8 carbons, 1-6 carbons, 1-4 carbons, 1-3 carbons, 2 carbons, or 1 carbon; hydroxylated alkyl, cycloalkyl, alkenyl, alkynyl, and aryl groups having from 1-8 carbons, 1-6 carbons, 1-4 carbons, 1-3 carbons, 2 carbons, or 1 carbon; and, carboxylated alkyl, cycloalkyl, alkenyl, alkynyl, and aryl groups having from 1-8 carbons, 1-6 carbons, 1-4 carbons, 1-3 carbons, 2 carbons, or 1 carbon; wherein, i and k are integers and at least one $R_i$ or $R_k$ in each repeating unit includes a carbonyl functionality;
- m is an integer selected to match the desired molecular weight of the polymer;
- obtaining a plurality of stabilizer molecules configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioester bond; and,
- polymerizing the plurality of the substituted cyclic disulfide molecules to create the polymer in the polar, protic solvent.

In some embodiments, the repeating units and the stabilizer molecules are the same, or substantially the same, chemical moieties following a degradation of the polymer during a recycling of the polymer.

The polar, protic solvents used can be any solvent considered suitable by a skilled artisan. Several suitable polar, protic solvents are taught herein, and each can be used at the discretion of the skilled artisan in view of the desired use. In some embodiments, for example, the polar, protic solvent can be pure ethanol, pure water, a combination of ethanol and water, or any aqueous solution suitable for the particular environment. In some embodiments the environment is a medical environment, and the polar, protic solvent includes a saline solution, or a buffer solution that can be used in a living organism.

In some embodiments, the methods include adding a stabilizer molecule taught herein. And, in some embodiments, the methods include adding both a stabilizer molecule taught herein and a terminator molecule taught herein. Examples of the stabilizer molecules and the terminator molecules that can be used are taught herein, and each can be selected and used at the discretion of the skilled artisan, the stabilizer used alone or in combination with a terminator, the stabilizer or the stabilizer and terminator combination selected and used as a particular polymer configuration designed and used in view of a desired application.

The polymerization reaction and stabilization reactions can be concurrent or in series. In some embodiments, the method can include placing the monomer and the stabilizer together in a reaction mixture and reacting them together. In some embodiments, the method can include polymerizing the monomer first, and then adding the stabilizer as a separate reaction. In some embodiments, the method can include placing the monomer, the stabilizer, and the terminator together in a reaction mixture and reacting them together. In some embodiments, the method can include polymerizing the monomer first, and then adding the stabilizer and terminator for a separate reaction. In some embodiments, the method can include polymerizing the monomer first, and then adding the stabilizer for a second reaction, and then adding the terminator for a third reaction.

The polymerization reaction and stabilization reactions can be concurrent or in series, with the reactant amounts controlled to drive the reactions and control competing reactions. In some embodiments, the methods include adding an amount of monomer that corresponds to m, and allowing the monomer to react to depletion in a first reaction, and then adding an amount of stabilizer and terminator for stabilizing the polymer, the amount of stabilizer and terminator corresponding to the expected amounts of first active thiol and second active thiol for a second reaction. In some embodiments, the methods include adding an amount of monomer that corresponds to m, and allowing the monomer to react to depletion in a first reaction, adding an amount of stabilizer that corresponds to an expected amount of first active thiol for a second reaction, and adding an amount of terminator that corresponds to an expected amount of second active thiol for a third reaction.

The polymerization reactions taught herein can be accelerated by adding acid and/or DMSO. In some embodiments, the methods further include adding DMSO to a mixture of cyclic disulfide monomers to accelerate the polymerization reaction. In some embodiments, the methods further include adding an acid taught herein to a mixture of cyclic disulfide monomers to accelerate the polymerization reaction. In some embodiments, the methods further include adding DMSO and acid taught herein to a mixture of cyclic disulfide monomers to accelerate polymerization the reaction. In some embodiments, the mixture of cyclic disulfide monomers can include stabilizer. In some embodiments, the mixture of cyclic disulfide monomers can include stabilizer and terminator.

The adhesive compositions can be concentrated as stable concentrated adhesive compositions that polymerize at the target site of adhesion. In some embodiments, the cyclic disulfide monomer can be combined with a stabilizer in a desired polar, protic solvent as taught herein. Vacuum is applied to the mixture for removal of most of the solvent, such that the mixture is a concentrated monomer and stabilizer in a small amount as a residual solvent. The concentrated adhesive composition can be applied to wet surfaces to initiate polymerization at the target site of adhesion.

The adhesive compositions can be coated onto a first surface for use as a pressure sensitive adhesive (PSA) to adhere the first surface to a second surface. A liquid form of an adhesive composition, included the concentrated form, can be applied to the first surface. The solvent in the adhesive composition can be allowed to evaporate, be drawn off under reduced pressure, or heated to produce a thin film adhesive on the first surface for adhering the first surface to the second surface. The adhesion can be reversible or irreversible and accomplished by making contact between the first surface and the second surface. The contact can include use of a modest pressure, such as the use of finger or hand pressure to the contact made between the first surface and the second surface.

A solid adhesive article can be formed with the adhesive compositions and used as an adhesive in itself. In some embodiments, the solid adhesive article can be an adhesive patch formed from the adhesive compositions. The solid adhesive article can be formed using molding, casting, or extrusion, for example. In some embodiments, the solid adhesive article can be an adhesive film. In some embodiments, the solid adhesive article can be an adhesive membrane. Any liquid, spray, or concentrated adhesive composition taught herein can be used in the formation of the solid adhesive article. In some embodiments, a polar, protic solvent such as water or a water containing solvent or buffer can be added to any adhesive composition taught herein to obtain a wet adhesive polymer composition. The wet adhesive polymer composition can be formed into the solid adhesive article. In some embodiments, the solid adhesive article may be self-supporting or supported on a temporary backing material. The article can then be adhered to a surface. A modest hand or finger pressure can be used as with the pressure sensitive adhesives to form an adhesion between the article and the surface. In some embodiments, a liquid or spray form of the adhesive compositions can be applied to the surface of the solid adhesive article before adhering the solid adhesive article to the surface.

The adhesive compositions taught herein can be thermally polymerized to form a solid adhesive article. In some embodiments, the adhesive composition is heated to thermally polymerize the composition to create a bulk polymer that can be formed into a solid adhesive article. The solid adhesive article can be formed using molding, casting, or extrusion, for example. In some embodiments, the solid adhesive article can be an adhesive film. In some embodiments, the solid adhesive article can be an adhesive membrane. In some embodiments, the solid adhesive article may be self-supporting or supported on a temporary backing material. The article can then be adhered to a surface. A modest hand or finger pressure can be used as with the pressure sensitive adhesives to form an adhesion between the article and the surface. In some embodiments, a liquid or spray form of the adhesive compositions can be applied to the surface of the solid adhesive article before adhering the solid adhesive article to the surface.

The liquid adhesive compositions can be concentrated by removing solvent to initiate polymerization and create an adhesive composition that contains sticky polymer in solution. The liquid adhesive composition can be referred to as a "liquid precursor" comprising monomer, monomer and stabilizer, or monomer and stabilizer and terminator, and the concentrated and polymerized composition can be referred to as a "polymer precursor", or "macromolecular precursor". The concentrated and polymerized composition can be made by allowing solvent to evaporate, using reduced pressure, or by heating, for example. The polymer precursor can be rediluted as a polymer precursor solution and used as the adhesive composition. The adhesive composition having the polymer precursor can be used to bond surfaces together, preferably in the presence of water to further polymerization and strengthen the bond.

The liquid adhesive compositions can be concentrated by removing solvent to initiate polymerization and create an adhesive composition that contains sticky polymer in solution, and then the polymer can be dried for later use. The liquid adhesive composition can be referred to as a "liquid precursor" comprising monomer, monomer and stabilizer, or monomer and stabilizer and terminator, and the concentrated and polymerized composition can be referred to as a "polymer precursor", or "macromolecular precursor". The concentrated and polymerized composition can be made by allowing solvent to evaporate, using reduced pressure, or by heating, for example. The polymer precursor can be dried for later use as a dry polymer used as an adhesive composition, or rediluted as a polymer precursor solution and used as the adhesive composition. The adhesive composition having the polymer precursor can be used to bond surfaces together, both dry and wet compositions preferably in the presence of water to further polymerization and strengthen the bond. The dried polymer can be formed into a solid adhesive article.

The methods can include any combination selected from the group consisting of a monomer as taught herein, a stabilizer as taught herein, a reaction solvent as taught herein, DMSO, and an acid as taught herein including Lewis acids and Bronsted acids. In some embodiments, the methods of making the adhesive composition include combining a cyclic disulfide monomer with a stabilizer in as a solid composition, wherein the solid composition can be polymerized at a desired time by contacting the solid composition with a reaction solvent, or by thermal polymerization. In some embodiments, the methods of making the adhesive composition include combining a cyclic disulfide monomer with a stabilizer and a reaction solvent. In some embodiments, the methods of making the adhesive composition include combining a cyclic disulfide monomer with a stabilizer and DMSO. In some embodiments, the methods of making the adhesive composition include combining a cyclic disulfide monomer with a stabilizer and an acid. In some embodiments, the methods of making the adhesive composition include combining a cyclic disulfide monomer with a stabilizer and a reaction solvent including DMSO. In some embodiments, the methods of making the adhesive composition include combining a cyclic disulfide monomer with a stabilizer and a reaction solvent including DMSO and an acid. Cross-linkers can be included, as taught herein, in any of these methods to at least further strengthen the adhesives. It should be appreciated that the reaction solvent can provide the terminator in some embodiments. For example, ethanol and ethanol/water mixtures work well as solvents, and the ethanol works well as a terminator. As such, the terminator can be easily provided through a careful selection of the reaction solvent.

The methods can include any combination selected from the group consisting of a polydisulfide polymer as taught herein, a monomer as taught herein, a stabilizer as taught herein, a reaction solvent as taught herein, DMSO, and an acid as taught herein including Lewis acids and Bronsted acids. In some embodiments, the methods of making the adhesive composition include a polydisulfide polymer as a solid composition, wherein the solid composition can be polymerized at a desired time by contacting the solid composition with a reaction solvent, or by thermal polymerization. In some embodiments, the methods of making the adhesive composition include combining a polydisulfide polymer with an acid as a solid composition, wherein the solid composition can be polymerized at a desired time by contacting the solid composition with a reaction solvent, or by thermal polymerization. In some embodiments, the methods of making the adhesive composition include combining a polydisulfide polymer with a cyclic disulfide monomer and a stabilizer in as a solid composition, wherein the solid composition can be polymerized at a desired time by contacting the solid composition with a reaction solvent, or by thermal polymerization. In some embodiments, the methods of making the adhesive composition include combining a polydisulfide polymer and a cyclic disulfide monomer with a stabilizer and a reaction solvent. In some embodiments, the methods of making the adhesive composition include combining a polydisulfide polymer and a cyclic disulfide monomer with a stabilizer and DMSO. In some embodiments, the methods of making the adhesive composition include combining a polydisulfide polymer and a cyclic disulfide monomer with a stabilizer and an acid. In some embodiments, the methods of making the adhesive composition include combining a polydisulfide polymer and a cyclic disulfide monomer with a stabilizer and a reaction solvent including DMSO. In some embodiments, the methods of making the adhesive composition include combining a polydisulfide polymer and a cyclic disulfide monomer with a stabilizer and a reaction solvent including DMSO and an acid. The conjugate base of the monomers can be included, as taught herein, to at least provide stability to the composition before polymerization. Terminators can be included, as taught herein, in any of these methods to at least further stabilizer the polymers. Cross-linkers can be included, as taught herein, in any of these methods to at least further strengthen the adhesives. It should be appreciated that the reaction solvent can provide the terminator in some embodiments. For example, ethanol and ethanol/water mixtures work well as solvents, and the ethanol works well as a terminator. As such, the terminator can be easily provided through a careful selection of the reaction solvent.

An increase in the reactant concentration causes a decrease in polymerization time. In some embodiments, the reactants are monomers, or monomers and stabilizers, and the concentration ranges from 100 mg/ml to 1000 mg/ml, from 100 mg/ml to 900 mg/ml, from 100 mg/ml to 800 mg/ml, from 100 mg/ml to 700 mg/ml, from 100 mg/ml to 600 mg/ml, from 100 mg/ml to 500 mg/ml, from 100 mg/ml to 400 mg/ml, from 100 mg/ml to 300 mg/ml, from 100 mg/ml to 200 mg/ml, 200 mg/ml to 1000 mg/ml, from 200 mg/ml to 900 mg/ml, from 200 mg/ml to 800 mg/ml, from 200 mg/ml to 700 mg/ml, from 200 mg/ml to 600 mg/ml, from 200 mg/ml to 500 mg/ml, from 200 mg/ml to 400 mg/ml, from 200 mg/ml to 300 mg/ml, 300 mg/ml to 1000 mg/ml, from 300 mg/ml to 900 mg/ml, from 300 mg/ml to 800 mg/ml, from 300 mg/ml to 700 mg/ml, from 300 mg/ml to 600 mg/ml, from 300 mg/ml to 500 mg/ml, from 300 mg/ml to 400 mg/ml, 400 mg/ml to 1000 mg/ml, from 400 mg/ml to 900 mg/ml, from 400 mg/ml to 800 mg/ml, from 400 mg/ml to 700 mg/ml, from 400 mg/ml to 600 mg/ml, from 400 mg/ml to 500 mg/ml, 500 mg/ml to 1000 mg/ml, from 500 mg/ml to 900 mg/ml, from 500 mg/ml to 800 mg/ml, from 500 mg/ml to 700 mg/ml, from 500 mg/ml to 600 mg/ml, or any amount or range therein in increments of 10 mg/ml. In some embodiments, the reactants are monomers, or monomers and stabilizers, and the concentration is about 100 mg/ml, 200 mg/ml, 300 mg/ml, 400 mg/ml, 500 mg/ml, 600 mg/ml, 700 mg/ml, 800 mg/ml, 900 mg/ml, 1000 mg/ml, 1100 mg/ml, 1200 mg/ml, 1300 mg/ml, 1400 mg/ml, 1500 mg/ml, 1600 mg/ml, 1700 mg/ml, 1800 mg/ml, 1900 mg/ml, 2000 mg/ml, or any amount or range therein in increments of 10 mg/ml.

In some embodiments, the term "about" can be used to refer to a range of amounts that surround the quantity that is modified by the term. It should be appreciated that one amount is "about" the same as another amount when the effects of the change of the amount do not make an appreciable change in the yield, function, activity, toxicity, or any other significant characteristic of a process or product produced by the process.

The term "about" is often used to cover such ranges, and it is intended herein to be construed to include amounts that do not have such a range at all; and, therefore, the term "about" is intended to be in amending patent claims to resolve, for example, any concerns presented about indefiniteness of such an amount, or written description, or perhaps even enablement. In some embodiments, when removing the term "about", the doctrine of equivalents can be assumed when construing the claims.

In some embodiments, the reactants are monomers, or monomers and stabilizers, and the concentration in solution is maximized by evaporating solvent to only a residual amount by evaporating, reducing pressure, or heating the reaction mixture to an observable minimal amount of solvent. In some embodiments, the minimal amount of solvent is sufficient to allow the monomers to remain soluble until polymerization. In some embodiments, the minimal amount of solvent is only that which allows the solvent to be observed within a polymerized monomer in the reaction mixture. In some embodiments, the minimal amount of solvent is that in which the solvent appears entirely removed but shows a substantial presence within a polymerized monomer in a chemical analysis of the reaction mixture.

The amounts of the reaction components can be expressed in mol %. As noted, the composition of the reaction mixtures can be all monomer; monomer and stabilizer; monomer, stabilizer, and terminator; or, monomer, stabilizer, and terminator. DMSO, an acid taught herein, or a combination of DMSO and an acid can be added to increase the rate of polymerization in the reaction mixtures. Cross-linkers can be added to increase the strength of the adhesive compositions.

In some embodiments, the mol % of the monomer (or combination of monomer and it's conjugate base) can range from 80 mol % to 100 mol %, from 80 mol % to 95 mol %, from 80 mol % to 90 mol %, from 80 mol % to 85 mol %, or any range or mol % therein in increments of 1 mol %, such as about 80 mol %, about 81 mol %, about 82 mol %, about 83 mol %, about 84 mol %, about 85 mol %, about 86 mol %, about 87 mol %, about 88 mol %, about 89 mol %, about 90 mol %, about 91 mol %, about 92 mol %, about 93 mol %, about 94 mol %, about 95 mol %, about 96 mol %, about 97 mol %, about 98 mol %, about 99 mol %, about 100 mol %. In embodiments that combine the monomer with it's conjugate base, the combination of the monomer to the conjugate base can be at a ratio that ranges from 5:1 to 1:5, such as 1:1, 2:1, 3:1, 4:1, or 5:1, 1:5, 1:4, 1:3, or 1:2 in the total mol % of that component.

In some embodiments, the mol % of the stabilizer can range from 0 mol % to 20 mol %, 0 mol % to 15 mol %, 0 mol % to 10 mol %, 0 mol % to 5 mol %, or any range or mol % therein in increments of 1 mol %, such as about 0 mol %, about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, and about 20 mol %, or any amount or range therein in increments of 0.5 mol %. This same amount of mol % can be used for the terminator, as the ratio of first active thiol to second active thiol can reasonably be assumed to be the same or similar in embodiments taught herein. However, it should be appreciated that, since alkanols work well for the terminator, and since ethanol is a convenient reaction solvent or component of a reaction solvent in some embodiments, the reaction solvent can serve as a source of excess terminator in such embodiments.

Poly(asparagusic acid) polymerization is an example of a method taught herein that does not require a stabilizer, at least in some uses of the adhesive, whereas the same application of poly(α-lipoic acid) would require a stabilizer due to a lower ring strain in the α-lipoic acid monomer. Due to the higher ring strain of asparagusic acid, the poly (asparagusic acid) tends to be slower to depolymerize relative to poly(α-lipoic acid). That said, the use of a stabilizer can be used to decrease the rate of depolymerization of any polymer taught herein, and the need for such added stability depends on the intended use of the polymer.

In some embodiments, DMSO is not used to catalyze the reactions, and in embodiments in which DMSO is used to help facilitate polymerization, the DMSO can be added in what a skilled artisan would consider "a catalytic amount", which is readily determined by the skilled artisan. In some embodiments, the DMSO is added to a reaction mixture in an amount ranging from 0 mol % to the catalytic amount. In some embodiments, the DMSO is added to a reaction mixture in an amount ranging from 0 ul/ml to 500 ul/ml, from 50 ul/ml to 400 ul/ml, from 75 ul/ml to 300 ul/ml, from 100 ul/ml to 200 ul/ml, or any range or amount therein in increments of 10 ul/ml. In some embodiments, the DMSO is added to a reaction mixture in an amount of about 50 ul/ml, about 75 ul/ml, about 100 ul/ml, about 125 ul/ml, about 150 ul/ml, about 175 ul/ml, about 200 ul/ml, about 225 ul/ml, about 250 ul/ml, about 275 ul/ml, about 300 ul/ml, or any range or amount therein in increments of 5 ul/ml.

In some embodiments, acid is not used to catalyze the reactions, and in embodiments in which acid is used to help facilitate polymerization, the acid can be added in what a skilled artisan would consider "a catalytic amount", which is readily determined by the skilled artisan. In some embodiments, the acid is added to a reaction mixture in an amount ranging from 0 mol % to the catalytic amount. In some embodiments, the acid is added to a reaction mixture in an amount ranging from 0 mol % to 20 mol %, from 5 mol % to 20 mol %, from 10 mol % to 20 mol %, from 15 mol % to 20 mol %, or any range or amount therein in increments of 1 mol %. In some embodiments, the acid is added in an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, or any range or amount therein in increments of 0.5 mol %.

As noted herein, a cross-linker can be added to increase the strength of the adhesions compositions. It should be appreciated that any cross-linker known to those of skill in the art of polymer chemistry and materials can be used where suitable and appropriate to the intended use and the chemical structure and functionality of the adhesive composition. In some embodiments, the process includes adding a cross-linker taught herein. The type of cross-linker selected can affect the amount of cross-linker needed, as can the type of cross-linker selected, and the amount added, can be chosen for a particular desired use of the adhesive composition. For example, a cross-linker can be added to create a desired mechanical response of the adhesive composition and/or, perhaps, a desired thermal response of the adhesive composition and/or, perhaps a desired thermomechanical response of the adhesive composition. In some embodiments, a mechanical response may be the "softness" of the composition, and the cross-linker may be added to modulate the polymer to have a lower modulus and higher fracture strain where a more "stretchable" adhesive composition may be desired. In another example, strength and hardness may be more desirable where the environment can be more punishing, such as in thin-film solar cells integrated with rooftops, roads, sidewalks, parking lots, and vehicle and aeronautic surfaces; heads-up displays in eyeglasses, windshields, and cockpits; and, perhaps integration with textiles, especially in physically demanding contexts (military, rescue, and medical workers). One of skill will appreciate that any of a variety of cross-linkers, including those taught herein, can be added to obtain any of a variety of mechanical responses in the adhesive compositions, with the desired mechanical response depends on the desired use for the adhesive composition.

In some embodiments, a cross-linker can be added in an amount of 1 mol % to 40 mol %, 1 mol % to 35 mol %, 1 mol % to 30 mol %, 1 mol % to 25 mol %, 1 mol % to 20 mol %, 1 mol % to 15 mol %, 1 mol % to 10 mol %, 1 mol % to 5 mol %, 5 mol % to 40 mol %, 5 mol % to 35 mol %, 5 mol % to 30 mol %, 5 mol % to 25 mol %, 5 mol % to 20 mol %, 5 mol % to 15 mol %, 5 mol % to 10 mol %, 10 mol % to 40 mol %, 10 mol % to 35 mol %, 10 mol % to 30 mol %, 10 mol % to 25 mol %, 10 mol % to 20 mol %, 10 mol % to 15 mol %, or any amount or range therein in increments of 1 mol %. In some embodiments, the cross-linker can be added in an amount of about 1 mol %, about 2 mol %, about 3 mol %, about 4 mol %, about 5 mol %, about 6 mol %, about 7 mol %, about 8 mol %, about 9 mol %, about 10 mol %, about 11 mol %, about 12 mol %, about 13 mol %, about 14 mol %, about 15 mol %, about 16 mol %, about 17 mol %, about 18 mol %, about 19 mol %, about 20 mol %, about 21 mol %, about 22 mol %, about 23 mol %, about 24 mol %, about 25 mol %, about 26 mol %, about 27 mol %, about 28 mol %, about 29 mol %, about 30 mol %, about 31 mol %, about 32 mol %, about 33 mol %, about 34 mol %, about 35 mol %, about 36 mol %, about 37 mol %, about 38 mol %, about 39 mol %, about 40 mol %, or any amount, range, or combination of these amounts.

The pH of the reactions can also be varied to achieve desired chemical activity in the reaction, namely reaction kinetics and products. In the polymerization reactions taught herein, for example, it was found that a lower pH can be expected to enhance polymerization. The pH that works the best for a set of reaction conditions will depend on the monomeric components being polymerized, the presence and type of reaction solvent, and the pressure of the reaction. In some embodiments, for example, the pH can range from a pH of 1 to a pH of 9, from a pH of 1 to a pH of 8, from a pH of 1 to a pH of 7, from a pH of 1 to a pH of 6, from a pH of 1 to a pH of 5, from a pH of 1 to a pH of 4, from a pH of 1 to a pH of 3, from a pH of 1 to a pH of 2, from a pH of 2 to a pH of 9, from a pH of 2 to a pH of 8, from a pH of 2 to a pH of 7, from a pH of 2 to a pH of 6, from a pH of 2 to a pH of 5, from a pH of 2 to a pH of 4, from a pH of 2 to a pH of 3, from a pH of 3 to a pH of 9, from a pH of 3 to a pH of 8, from a pH of 3 to a pH of 7, from a pH of 3 to a pH of 6, from a pH of 3 to a pH of 5, from a pH of 3 to a pH of 4, from a pH of 4 to a pH of 9, from a pH of 4 to a pH of 8, from a pH of 4 to a pH of 7, from a pH of 4 to a pH of 6, from a pH of 4 to a pH of 5, from a pH of 5 to a pH of 9, from a pH of 5 to a pH of 8, from a pH of 5 to a pH of 7, from a pH of 5 to a pH of 6, from a pH of 6 to a pH of 9, from a pH of 6 to a pH of 8, from a pH of 6 to a pH of 7, from a pH of 6 to a pH of 8, from a pH of 6 to a pH of 7, from a pH of 7 to a pH of 8, or any pH or pH range therein in increments of 0.1 pH. In some embodiments, the pH can be a pH of about 1, a pH of about 2, a pH of about 3, a pH of about 4, a pH of about 5, a pH of about 6, a pH of about 7, a pH of about 8, a pH of about 9, or any pH or pH range therein in increments of 0.1 pH. The pH can also vary during the course of a reaction, in some embodiments. The effect can be to increase the kinetics of the reaction, decrease the kinetics of the reaction, quell the reaction, or convert the reaction products. In some embodiments, the pH can be increased during the course of such a process. In some embodiments, the pH can be decreased during the course of such a process. And, in some embodiments the pH can oscillate during the course of such a process.

The temperature of the reactions can also be varied to achieve desired chemical activity in the reaction, namely reaction kinetics and products. In the polymerization reactions taught herein, for example, a lower temperature can be expected to at least reduce the rate of polymerization, and a higher temperature can be expected to at least increase the rate of polymerization. Likewise, the rate of depolymerization will also decrease at a lower temperature and increase at a higher temperature. It should be appreciated that, if we increase the temperature, then we have more product and the reaction shifts towards the reactants; and, if we decrease the temperature, then have less product and so the reaction shifts towards the products. The temperature that works the best for a set of reaction conditions will depend on the monomeric components being polymerized, the presence and type of reaction solvent, and the pressure of the reaction. In some embodiments, for example, the temperature can range from 0° C. to 120° C., from 5° C. to 120° C., from 10° C. to 120° C., from 15° C. to 120° C., from 20° C. to 120° C., from 25° C. to 120° C., from 30° C. to 120° C., from 35° C. to 120° C., from 40° C. to 120° C., from 45° C. to 120° C., from 50° C. to 120° C., from 55° C. to 120° C., from 60° C. to 120° C., from 65° C. to 120° C., from 70° C. to 120° C., from 75° C. to 120° C., from 80° C. to 120° C., from 85° C. to 120° C., from 90° C. to 120° C., from 95° C. to 120° C., from 100° C. to 120° C., from 105° C. to 120° C., from 110° C. to 120° C., from 115° C. to 120° C., or any amount or range therein in increments of 1° C. In some embodiments, for example, the temperature can range from 10° C. to 100° C., from 15° C. to 100° C., from 20° C. to 100° C., from 25° C. to 100° C., from 30° C. to 100° C., from 35° C. to 100° C., from 40° C. to 100° C., from 45° C. to 100° C., from 50° C.

to 100° C., from 55° C. to 100° C., from 60° C. to 100° C., from 65° C. to 100° C., from 70° C. to 100° C., from 75° C. to 100° C., from 80° C. to 100° C., from 85° C. to 100° C., from 90° C. to 100° C., from 95° C. to 100° C., or any amount or range therein in increments of 1° C. In some embodiments, for example, the temperature can range from 20° C. to 100° C., from 25° C. to 100° C., from 30° C. to 100° C., from 35° C. to 100° C., from 40° C. to 100° C., from 45° C. to 100° C., from 50° C. to 100° C., from 55° C. to 100° C., from 60° C. to 100° C., from 65° C. to 100° C., from 70° C. to 100° C., from 75° C. to 100° C., from 80° C. to 100° C., from 85° C. to 100° C., from 90° C. to 100° C., from 95° C. to 100° C., or any amount or range therein in increments of 1° C. In some embodiments, for example, the temperature can range from 20° C. to 80° C., from 25° C. to 80° C., from 30° C. to 80° C., from 35° C. to 80° C., from 40° C. to 80° C., from 45° C. to 80° C., from 50° C. to 80° C., from 55° C. to 80° C., from 60° C. to 80° C., from 65° C. to 80° C., from 70° C. to 80° C., from 75° C. to 80° C., or any amount or range therein in increments of 1° C. In some embodiments, for example, the temperature can range from 20° C. to 60° C., from 25° C. to 60° C., from 30° C. to 60° C., from 35° C. to 60° C., from 40° C. to 60° C., from 45° C. to 60° C., from 50° C. to 60° C., from 55° C. to 60° C., from 60° C. to 60° C., or any amount or range therein in increments of 1° C. In some embodiments, for example, the temperature can range from 20° C. to 40° C., from 25° C. to 40° C., from 30° C. to 40° C., from 35° C. to 40° C., or any amount or range therein in increments of 1° C. In some embodiments, for example, the temperature can be about 0° C., about 1° C., about 2° C., about 3° C., about 4° C., about 5° C., about 6° C., about 7° C., about 8° C., about 9° C., about 10° C., about 11° C., about 12° C., about 13° C., about 14° C., about 15° C., about 16° C., about 17° C., about 18° C., about 19° C., about 20° C., about 21° C., about 22° C., about 23° C., about 24° C., about 25° C., about 26° C., about 27° C., about 28° C., about 29° C., about 30° C., about 31° C., about 32° C., about 33° C., about 34° C., about 35° C., about 36° C., about 37° C., about 38° C., about 39° C., about 40° C., about 41° C., about 42° C., about 43° C., about 44° C., about 45° C., about 46° C., about 47° C., about 48° C., about 49° C., about 50° C., about 51° C., 52° C., about 53° C., 54° C., about 55° C., about 56° C., about 57° C., about 58° C., about 59° C., about 60° C., about 61° C., about 62° C., about 63° C., about 64° C., about 65° C., about 66° C., about 67° C., about 68° C., about 69° C., about 70° C., about 71° C., about 72° C., about 73° C., about 74° C., about 75° C., about 76° C., about 77° C., about 78° C., about 79° C., about 80° C., about 81° C., about 82° C., about 83° C., about 84° C., about 85° C., about 86° C., about 87° C., about 88° C., about 89° C., about 90° C., about 91° C., about 92° C., about 93° C., about 94° C., about 95° C., about 96° C., about 97° C., about 98° C., about 99° C., about 100° C., about 101° C., about 102° C., about 103° C., about 104° C., about 105° C., about 106° C., about 107° C., about 108° C., about 109° C., about 110° C., about 111° C., about 112° C., about 113° C., about 114° C., about 115° C., about 116° C., about 117° C., about 118° C., about 119° C., about 120° C., or any amount or range therein in increments of 0.1° C. Temperature can also vary during the course of a reaction, in some embodiments. The effect can be to increase the kinetics of the reaction, decrease the kinetics of the reaction, quell the reaction, or convert the reaction products. In some embodiments, the temperature can be increased during the course of such a process. In some embodiments, the temperature can be decreased during the course of such a process. And, in some embodiments the temperature can oscillate during the course of such a process.

The pressure of the reactions can also be varied. The reactions can be in solution, suspension, or a solid, in a reaction solvent that can include any reaction solvent taught herein, for example, polar, protic solvents, polar, aprotic solvents, alcohol solvents, aqueous solvents, water, any combination of those, and the like. The amount of pressure desired can vary according to the reaction solvent, or solvent combination, selected for the reaction. In some embodiments, the pressure can vary from 1 bar to a pressure reduced as low as 0 bar. In some embodiments, the pressure is limited to the limits of vacuum source used including, for example, about $10^{-1}$ torr, about $10^{-2}$ torr, about $10^{-3}$ torr, about $10^{-4}$ torr, about $10^{-5}$ torr, about $10^{-6}$ torr, about $10^{-7}$ torr, about $10^{-8}$ torr, about $10^{-9}$ torr, about $10^{-10}$ torr, about $10^{-11}$ torr, or any amount or range therein. In some embodiments, high pressures can be used for reactions during the formation of a a desired solid product from polymeric materials in a compression process, and the pressure used can depend on the temperature used, where the pressure increases as the temperature decreases, and the pressure decreases and the temperature increases.

In some embodiments, the pressure used can range from 14.7 psi to 10,000 psi, or any amount or range therein in increments of 1 psi. In some embodiments, the pressure used can range from 100 psi to 10,000 psi, 200 psi to 10,000 psi, from 300 psi to 10,000 psi, from 400 psi to 10,000 psi, from 500 psi to 10,000 psi, from 600 psi to 10,000 psi, from 700 psi to 10,000 psi, from 800 psi to 10,000 psi, from 900 psi to 10,000 psi, from 1000 psi to 10,000 psi, from 2000 psi to 10,000 psi, from 3000 psi to 10,000 psi, from 4000 psi to 10,000 psi, from 5000 psi to 10,000 psi, from 6000 psi to 10,000 psi, from 7000 psi to 10,000 psi, from 8000 psi to 10,000 psi, from 9000 psi to 10,000 psi, from 2000 psi to 5,000 psi, from 5000 psi to 10,000 psi, or any amount or range therein in increments of 10 psi. In some embodiments, the pressure used can be about 100 psi, about 500 psi, about 1000 psi, about 1500 psi, about 2000 psi, about 2500 psi, about 3000 psi, about 3500 psi, about 4000 psi, about 4500 psi, about 5000 psi, about 5500 psi, about 6000 psi, about 6500 psi, about 7000 psi, about 7500 psi, about 8000 psi, about 8500 psi, about 9000 psi, about 9500 psi, 10,000 psi, or any amount or range therein in increments of 10 psi. Pressure can also vary during the course of a reaction, in some embodiments. The effect can be to increase the kinetics of the reaction, decrease the kinetics of the reaction, quell the reaction, or convert the reaction products. In some embodiments, the pressure can be increased during the course of such a process. In some embodiments, the pressure can be decreased during the course of such a process. And, in some embodiments the pressure can oscillate during the course of such a process.

Any combination of reaction conditions set-forth herein can be selected to obtain the process and products desired, and it should be appreciated that these conditions, excepting the occurrence of conditions that produce surprisingly desirable results, can be readily determined by the skilled artisan without undue experimentation. Several examples of actual reaction conditions and results have been provided herein to enable the skilled artisan in the practice of the invention.

Moreover, any of the adhesive compositions, or solid adhesive articles formed from the compositions, can be sterilized using pure ethanol, a water-ethanol mixture, UV light, gamma irradiation, ethylene oxide or a combination thereof.

Adhesive Composition Products

The adhesive composition can take several forms, and can serve as both an adhesive and sealant: a liquid, a solid, a liquid and a solid, and a free-flowing solid which can include powders. The liquid compositions can be directly sprayed or brushed onto surfaces for bonding, or onto a solid form of the adhesive, such as a patch, film, or membrane formed from the polymer. The solid, such as the patch, film, or membrane can be configured for direct application as an adhesive. In some embodiments, the adhesive composition functions as an adhesive alone. In some embodiments, the adhesive composition functions as a sealant. In some embodiments, the adhesive composition functions as a hemostat. In some embodiments, the adhesive composition functions as a therapeutic agent. In some embodiments, the adhesive composition functions as any combination of adhesive, sealant, hemostat, and therapeutic agent.

The adhesive compositions can be used in medical applications and non-medical applications. In medical applications, the adhesive compositions are biocompatible and exhibit many of the features of superglue, such as superfast polymerization and high adhesion strength to tissue. The adhesive compositions can be used in the form of a spray, brush, or solid adhesive article for various applications. The excellent biocompatibility and biodegradability of the adhesive compositions allow for both topical use and internal uses of the adhesive compositions in medical treatments. The adhesive compositions function as a barrier to the transfer of microbials, such as bacteria, making the adhesive compositions superior to hydrogel-based adhesives currently approved for internal applications. Moreover, non-medical PSAs and structural adhesives can also be made using the polymerization methods taught herein. Like all of the adhesive compositions taught herein, the products that are PSAs and structural adhesives show excellent underwater adhesion and can be recycled to monomeric species in a cost-effective manner.

Medical

As taught herein, the adhesive compositions can be made to function very well as medical adhesives, sealants, and hemostats. The products include liquid adhesives; spray adhesives; solid adhesive articles such as adhesive patches, films, and membranes; and, free-flowing solids such as powders.

The medical products can be used as a topical tissue adhesive, topical tissue sealant, or a topical tissue adhesive and sealant. These products can be used, for example, in closure of topical wounds created by surgical incisions or traumatic injuries. These products can be applied to any such topical use.

The medical products can be used as an internal tissue adhesive, an internal tissue sealant, an internal tissue hemostat, or any combination thereof. These products can be used, for example, in closure of internal wounds created by surgical incisions or traumatic injuries. These products can be applied to any such internal use. In some embodiments, the use can be for adhesion during a surgical procedure. Examples include cartilage repair, anastomosis of blood vessels or intestines, vascular graft attachment, sealing of intestine or stomach or lung or bladder punctures, general hemostasis, spinal dural sealant, ocular sealant, dural sealant, lung parenchymal sealant, gastric perforation sealant, fetal membrane sealant, etc. in some embodiments, these medical products can be used in circumcisions, implant grafting, plastic surgeries, and the like.

The medical products can be used as an adjunct to other existing procedures as an adhesive, sealant, hemostat, or any combination thereof. The proven function of the adhesive compositions as products for adhesion, sealant, and as a hemostat, allows the products to be used with any existing medical procedure, thus improving those procedures. In some embodiments, the adhesive products taught herein can be used as an adjunct material for suturing, stapling, tacks, and the like. In some embodiments, the adhesive products taught herein can be used as an adjunct in the anchoring of medical devices to tissue, the attachment of wound dressings, the attachment of skin grafts, the attachment of collagen membranes, as well as with decellularized tissues, ostomy devices, and other synthetic medical devices.

Non-Medical

Medical applications need to address concerns about biocompatibility, and non-medical applications do not need to address such concerns. As such, the non-medical grade adhesives can use a wider variety of reaction components. For example, the stabilizer and the terminator can be any chemical moieties acceptable for the non-medical application of interest, and do not have to be biocompatible topically or internally to a subject. This allows the products to include materials that otherwise would be toxic topically or internally to a subject in a medical use of the adhesive compositions. This allows for the use of a wider variety of chemical components in the adhesive compositions, such as isocyanates, diisocyanates, oxidized polyphenol, methanol, and isopropanol, to name a few.

The non-medical applications are vast. Any two surfaces can be adhered as a temporary bond or a permanent bond, using the adhesive compositions taught herein. In some embodiments, the product can be a liquid, spray, solid adhesive article, or a free-flowing powder that can be used to join any two materials together. In some embodiments, the product can be a liquid, spray, solid adhesive article, or a free-flowing powder that can be used to create a pressure sensitive adhesive (PSA) or structural adhesive on a solid article. In some embodiments, a thin film of the adhesive can be applied to a backing material to make sticky notes, scotch tape, food packaging, consumer product labels, and the like. And, in some embodiments, the adhesive products taught herein can be used as a permanent adhesive for bonding two surfaces together, whether the materials are similar or dissimilar.

EXAMPLES

Examples 1-21 are Polymers of Poly(Lipoic Acid) and Methods of Making the Polymers and Products of the Polymers Poly($\alpha$-lipoic acid) has attracted significant attention due to its excellent mechanical properties and adhesion strength, as well as a cost-effective production and closed-loop chemical recycling. It's found in nature, and is safe, but depolymerizes quickly. Despite multiple attempts, the art has not been able to create a stable form of poly($\alpha$-lipoic acid) having these desired features. The following examples show that the instant technology provides such poly($\alpha$-lipoic acid) compositions, methods of making, and products. These examples teach that a poly($\alpha$-lipoic acid) can be provided as (i) a precursor solution of monomer used to form the poly($\alpha$-lipoic acid); (ii) a solution of poly($\alpha$-lipoic acid); (iii) a freeze-dried form of the poly($\alpha$-lipoic acid) that can be reconstituted as a spray in solution or formed into a solid adhesive product; (iv) a combination of a poly(α-lipoic acid) and asparagusic acid monomer in solution; or any combination thereof.

Example 1. An Illustration of the Rapid Depolymerization of α-Lipoic Acid (L1) Monomer in Aqueous Solution that Occurs in Nature This example is creating a baseline polydisulfide system that shows the depolymerization problem in aqueous solution, wherein the polydisulfide system includes α-lipoic acid (L1) added to an aqueous phosphate buffer to produce a rapid polymerization and depolymerization of polydisulfide polymer.
Experimental:
An ethanolic solution of pure α-lipoic acid L1 was prepared at 400 mg/mL and added to an aqueous phosphate buffer. A metastable sticky polymer was obtained, but within a few minutes (<5 min), the sticky polymer converted to a solid monomeric precipitate with no apparent adhesive property. These observations suggest that rapid polymerization of L1 upon contact with water was followed by rapid depolymerization of the polymer product, compromising its efficacy as a practical adhesive or sealant.

Example 2. Stabilizing the Polymer to Depolymerization by Adding a Derivatized α-Lipoic Acid Monomer as a Stabilizing Molecule in a Slow Polymerization System This example is solving the depolymerization problem by derivatizing the α-lipoic acid (L1) monomer with N-hydroxysuccinimide (NHS) ester to create a stabilizer molecule (L2), the NHS-derivative of the the the α-lipoic acid (L1) monomer. The stabilizer is added to an absolute ethanol solution of the α-lipoic acid (L1) that includes a catalytic amount of DMSO for a slow polymerization system that shows stabilization of the polymer by the derivatized α-lipoic acid monomer.
Experimental:
An ethanolic solution of the mixture of α-lipoic acid L1 and L2 was prepared with a mol ratio Li:L2 of 93:7, and a catalytic amount of DMSO was added to ensure the solubility of the NHS esters. The ethanolic adhesive precursor solution prepared in this manner with a total concentration (L1+L2) of 400 mg/mL was observed to form a gel within 1 hour. In contrast, a pure L1 solution at a similar concentration did not form a gel even at extended periods of time. The total (L1+L2) concentration investigated ranged from a low of 200 mg/mL to a high of 600 mg/mL; we observed a decrease in gelation time with an increase in monomer concentration. The formation of a gel indicate that polymerization has occurred and that the polymer produced is stable, clearly establishing the efficacy of NHS esters to stabilize the polymer chain end and prevent rapid depolymerization of the polymer product.

Example 3. Testing the Ability of the Derivatized α-Lipoic Acid Monomer to Stabilize the Polydisulfide Polymer in a Fast Polymerization System Water is added to the system of Example 2 to create a fast polymerization system, and a stable polymer is again obtained.

Experimental:
At any time prior to or after gelation of the precursor solution, exposure to water triggers dithiolane polymerization which can be exploited for the purposes of isolating a polymer adhesive or for adhering objects together. An ethanolic liquid mixture of α-lipoic acid L1 and L2 exposed to water led to the immediate formation of a stable sticky solid (FIG. 1). The differential scanning calorimetry analysis of the obtained wet polymer showed an obvious glass transition (Tg) of around −29° C., indicating the formation of a polymer. We believe α-lipoic acid undergoes self-catalyzed polymerization followed by stabilization with NHS esters. Nonetheless, the aqueous polymerization appears to be less sensitive and extremely fast irrespective of the solution concentrations. We believe that due to the amphiphilic nature of the α-lipoic acid, it undergoes micelle-like self-reorganization in contact with water, which locally concentrates the cyclic backbone to accelerate the polymerization rate. Furthermore, detailed $^1$H NMR experiments of diluted ethanolic solution of the mixtures show excellent stability of the NHS esters even at an extended period. Therefore, this opens the possibility of an on-demand aqueous polymerization from a precursor ethanolic solution, which we considered to be advantageous for translation in medical and other underwater applications.

Example 4. Designing and Testing a Second Derivatized α-Lipoic Acid Monomer (L3) Having a Higher Electrophilicity than the NHS-Derivatized α-Lipoic Acid Monomer (L2) and Testing L3 for It's Strength as a Stabilizer This example adds the stabilizer molecule (L3) to the slow polymerization system that includes α-lipoic acid (L1) in absolute ethanol, with and without the catalytic amount of DMSO, to create a stable polydisulfide polymer. In addition, a faster polymerization was obtained using L3 instead of L2, and it's believed this is due to the higher electrophilicity of L3. Polymerization time was also decreased in the presence of DMSO.
Experimental:
An ethanolic solution of a mixture of α-lipoic acid L1 and L3 was prepared with a mol ratio Li:L3 of 93:7, and a catalytic amount of DMSO was added to ensure the solubility of the NHS esters. The ethanolic adhesive precursor solution prepared in this manner had a total concentration (L1+L3) of 400 mg/ml and was observed to form a gel within 30 minutes. The total (L1+L3) concentration investigated ranged from a low of 200 mg/mL to a high of 1000 mg/mL; we observed a decrease in gelation time with an increase in monomer concentration. The faster gelation time for L1+L3 compared to L1+L2 was attributed to the higher electrophilicity of L3. Moreover, the presence of a catalytic amount of DMSO also appeared to enhance the rate of solution polymerization, as a DMSO-free ethanolic solution of L1 and L3 showed much slower gelation kinetics than a DMSO-containing solution. The positive influence of polar aprotic solvents in substitution reactions is well known in the literature and we believe the presence of a catalytic amount of DMSO enhances the chain end coupling with the NHS ester, leading to faster polymerization.

Example 5. Stepwise Polymerization and Stabilization of Poly(α-Lipoic Acid)

The examples above react the α-lipoic acid (L1) with the Gly-OSu derivative of α-lipoic acid stabilizer (L3), such that polymerization of the α-lipoic acid (L1) occurs concurrent to the stabilization of polymer by reacting the polymer with the α-lipoic acid stabilizer (L3). This example allows for polymerization to occur in a first step, and the stabilization to occur as a second step.

Experimental:

An ethanolic solution of pure α-lipoic acid (L1) was prepared at 400 mg/mL, and 5 mol % HCl (4M in dioxane) was added. The obtained mixture was stirred for 15 min, and a gradual increase in viscosity was observed, indicating polymerization of lipoic acid. Subsequently, the Gly-OSu derivative of lipoic acid (L3) was dissolved in a small amount of DMSO and added to the reaction mixture (mol ratio of Li:L3 of 93:7) to stabilize the polymer. The obtained solution mixture was further polymerized by addition of excess 1×PBS. The obtained precipitate was freeze-dried to obtain a pale yellow dry polymer. It should be appreciated that stepwise synthesis of a stabilized polymer may allow for control over the size of the polymer created prior to addition of the stabilizer which is reasonable to expect is a variable that may also affect polymer size when present during the polymerization of the monomer.

Example 6. Testing Other Electrophilic Molecules as Stabilizers

This example tests hexamethylene diisocyanate, benzoquinone, maleic anhydride, and acetyl-glycine N-hydroxysuccinimide ester as stabilizers. Polymer was formed in an hour in the slow polymerization system that includes α-lipoic acid (L1) in absolute ethanol with and without catalytic amount of DMSO. In each case, a stable polymer was obtained, and water was added to the reaction with maleic anhydride to show that a stable polymer was still obtained in the fast polymerization system.

Experimental:

An ethanolic solution of a mixture of α-lipoic acid L1 and hexamethylene diisocyanate was prepared with a mol ratio L1:hexamethylene diisocyanate of 90:10, and a catalytic amount of DMSO was added. The ethanolic adhesive precursor solution prepared in this manner had a total concentration (L1+ hexamethylene diisocyanate) of 400 mg/ml and was observed to form a gel within 15 minutes.

An ethanolic solution of a mixture of α-lipoic acid L1 and 1,4 benzoquinone was prepared with a mol ratio L1:benzoquinone of 90:10, and a catalytic amount of DMSO was added. The ethanolic adhesive precursor solution prepared in this manner had a total concentration (L1+ benzoquinone) of 400 mg/ml and was observed to form a gel within 30 minutes.

An ethanolic solution of a mixture of α-lipoic acid L1 and acetyl-glycine N-hydroxysuccinimide ester was prepared with a mol ratio L1:acetyl-glycine N-hydroxysuccinimide ester of 93:7, and a catalytic amount of DMSO was added. The ethanolic adhesive precursor solution prepared in this manner had a total concentration (L1+ acetyl-glycine N-hydroxysuccinimide ester) of 400 mg/ml and was observed to form a gel within 30 min.

An ethanolic solution of a mixture of α-lipoic acid L1 and maleic anhydride was prepared with a mol ratio L1:maleic anhydride of 93:7, and a catalytic amount of DMSO was added. The ethanolic adhesive precursor solution prepared in this manner had a total concentration (L1+ maleic anhydride) of 400 mg/ml. Thereupon, the precursor solution was exposed to water to trigger dithiolane polymerization to obtain a stable sticky solid (FIG. 1).

Example 7. Creating a Stabile Liquid Precursor by Suppressing Initiation of Polymerization This example offers a DMSO solution of monomers that suppresses polymerization of the monomers until water is added. The α-lipoic acid (L1) monomer is added to methanol with a catalytic amount of DMSO, the NHS-derivatized α-lipoic acid monomer (L2), and a conjugate base of the α-lipoic acid (L1) monomer, sodium lipoate (L4), was added to compete with the tendency of the disulfide groups to self-polymerize. The NHS-derivative of the α-lipoic acid (L1) monomer was added to stabilize the polymer. Methanol was evaporated at low vacuum at temperature <30° C. to obtain a liquid precursor solution. The solution was successful, stable for a month at 5° C., and the polymerization is ultrafast with the addition of water.

Experimental:

The self-catalysis of α-lipoic acid takes place by the activation of disulfide with a carboxylic acid. Thus, we hypothesized that introduction of a functional group with higher electron density than disulfide will act as a potential competitor of disulfide, thereby suppressing initiation. To test our hypothesis, a mixture of L1, sodium lipoate (L4), and L2 (mol ratio:70:23:7) were dissolved in methanol with a catalytic amount of DMSO to obtain a homogeneous solution. Interestingly, a viscous honey-like yellow liquid was obtained after the complete evaporation of the solvent (FIG. 1). $^1$H NMR analysis of the obtained liquid confirmed the monomeric state of the mixture. The obtained liquid shows excellent stability, as no apparent change in viscosity was observed over a month when stored at 5° C. However, the liquid undergoes ultrafast polymerization when brought into contact with water (FIG. 1) to yield an adhesive polymer. We surmise that due to its higher hydration energy, L4 becomes solvated as it comes in contact with water, leading to disulfide activation by the carboxylic acids. This approach provides an adhesive precursor suitable for spray, brush or injection mode of application.

Example 8. Creating a Solid, Adhesive Polymer Patch

A solution of the α-lipoic acid (L1) monomer in absolute ethanol was added to a solution of the NHS-derivatized α-lipoic acid (L2) in DMSO. Excess phosphate-buffered saline (PBS) was added to polymerize the monomer, and a stable polymer was created, freeze-dried, and compression molded between polydimethylsiloxane (PDMS) coated paper to create a thin film solid adhesive patch having desirable mechanical properties suitable for many applications, including significant stretch without rupture, stiffness suitable for use on biological tissue, high hysteresis, excellent fatigue resistance, excellent stress relaxation, resistance to deformity, and self-healing, for example.

Experimental:

α-Lipoic acid (900 mg, 4.4 mmol) was dissolved in 2.3 mL absolute ethanol. Separately, L2 (100 mg, 0.3 mmol) was dissolved in 200 uL DMSO and added to the lipoic acid solution. The resulting solution was rested for 1 hour before adding excess 1× PBS (pH 7.4, temperature 37° C.) under vigorous stirring. The sticky resulting polymer was washed with fresh PBS, followed by miliQ water. The obtained pale-yellow polymer was freeze-dried to obtain dry polymer and then compression molded at 75° C. for 15 min between PDMS backing paper to obtain a homogeneous thin film (thickness 250±50 μm) (FIG. 1). The polymer films were rested overnight before further use.

Figure 2A:
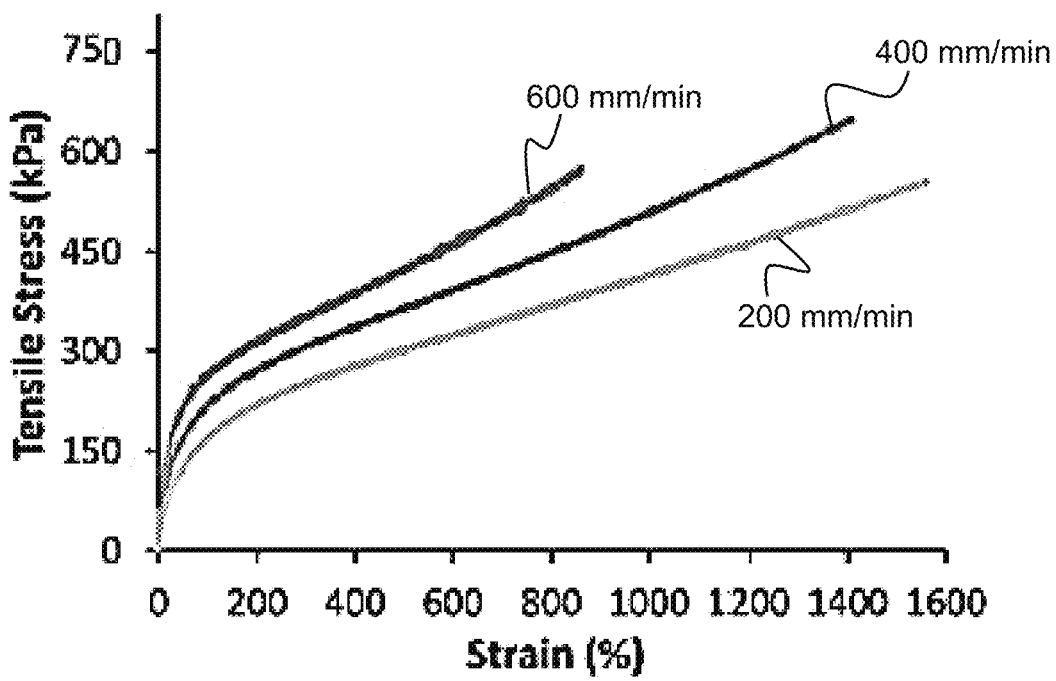
FIG. 2A measures the stress-strain curve of the synthesized polymer at different strain rates, 200 mm/min, 400 mm/min, and 600 mm/min, in some embodiments. The results show that the polymer can be stretched over 10 times of its initial length (1000% strain deformation) without rupture.
Figure 2B:
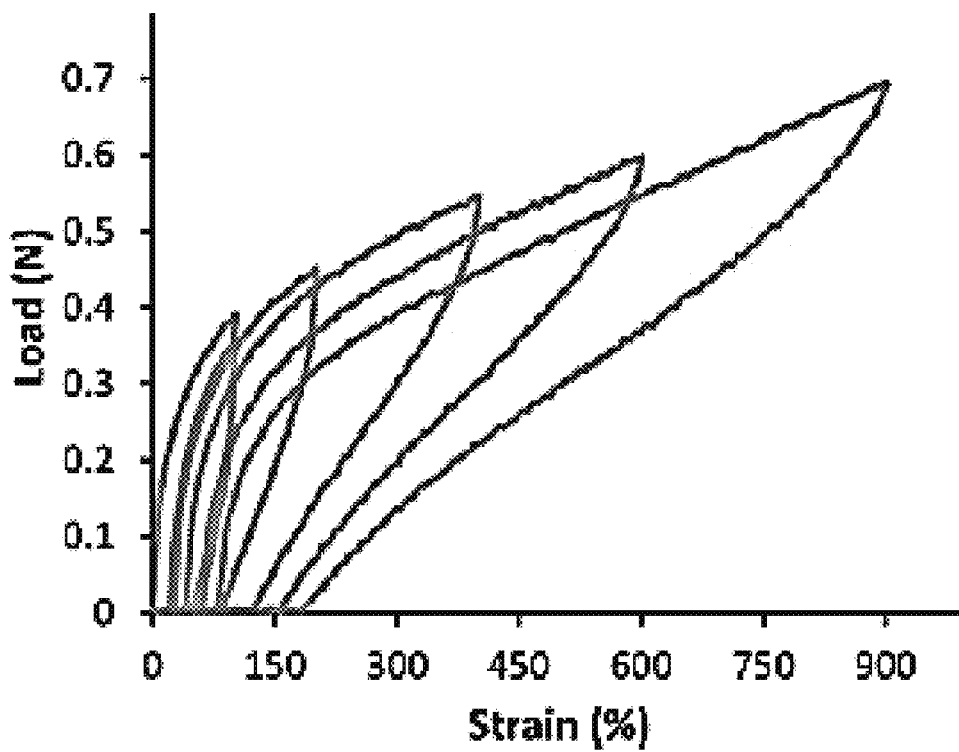
FIG. 2B is a cyclic stress-strain measurement with subsequent incremental strain without intermediate resting, in some embodiments. The polymer shows excellent recovery at the lower deformation region, whereas another cyclic stress-strain measurement with subsequent incremental strain without intermediate resting indicates excellent fatigue resistance of the obtained polymer.

Stress-strain measurements of the resulting polymer patch show the polymer could be stretched over 10 times of its initial length (1000% strain deformation) without rupture (See FIG. 2A). The young's modulus (481±60 kPa) was calculated from the lower region of the stress-strain curve obtained at 200 mm/min, demonstrating the stiffness of the adhesive as being within the range of many biological tissues. The stress-strain measurements with increasing strain rates revealed higher stiffness of the polymer, indicating the viscoelastic nature of the polymer (See FIG. 2A). Furthermore, the cyclic stress-strain measurements also display a high hysteresis, a characteristic feature of viscoelastic polymer. The polymer shows excellent recovery at the lower deformation region, whereas another cyclic stress-strain measurement with subsequent incremental strain without intermediate resting indicates excellent fatigue resistance of the obtained polymer (See FIG. 2B).

Figure 2C:
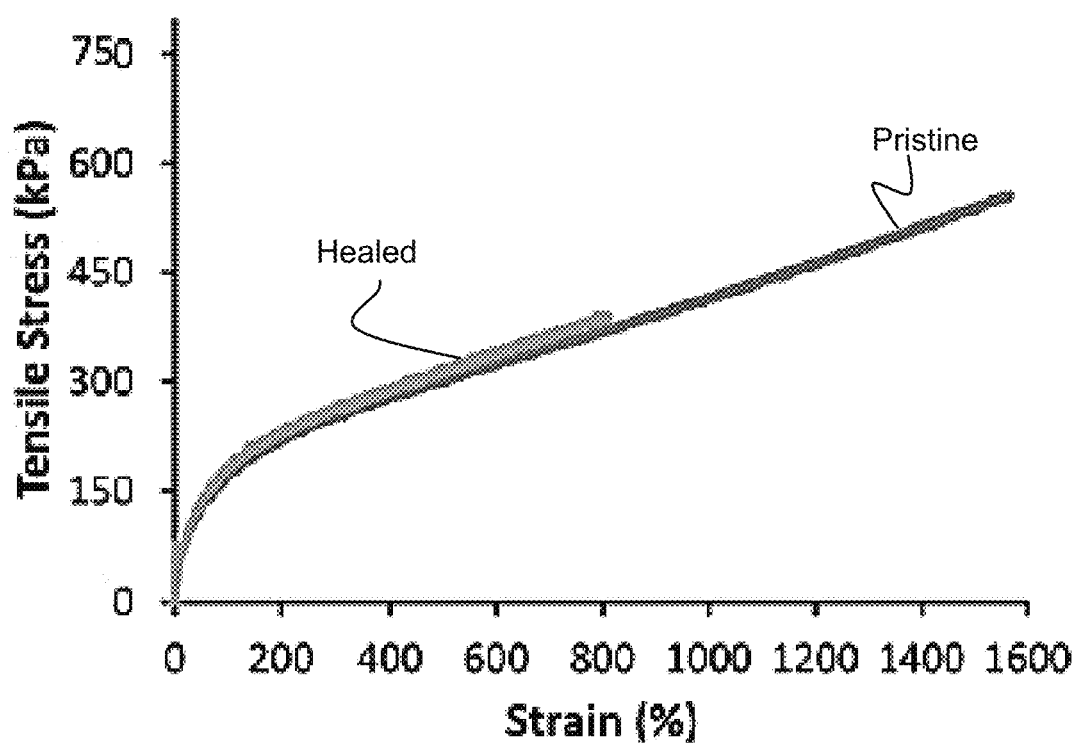
FIG. 2C is a stress-strain curve taken after 2 min healing at 37° C., in some embodiments. A polymer film was cut into two pieces and then carefully brought into contact for 2 min at 37° C. and equilibrated for 5 min at room temperature before measurements were taken. Interestingly, and surprisingly.
Figure 2D:
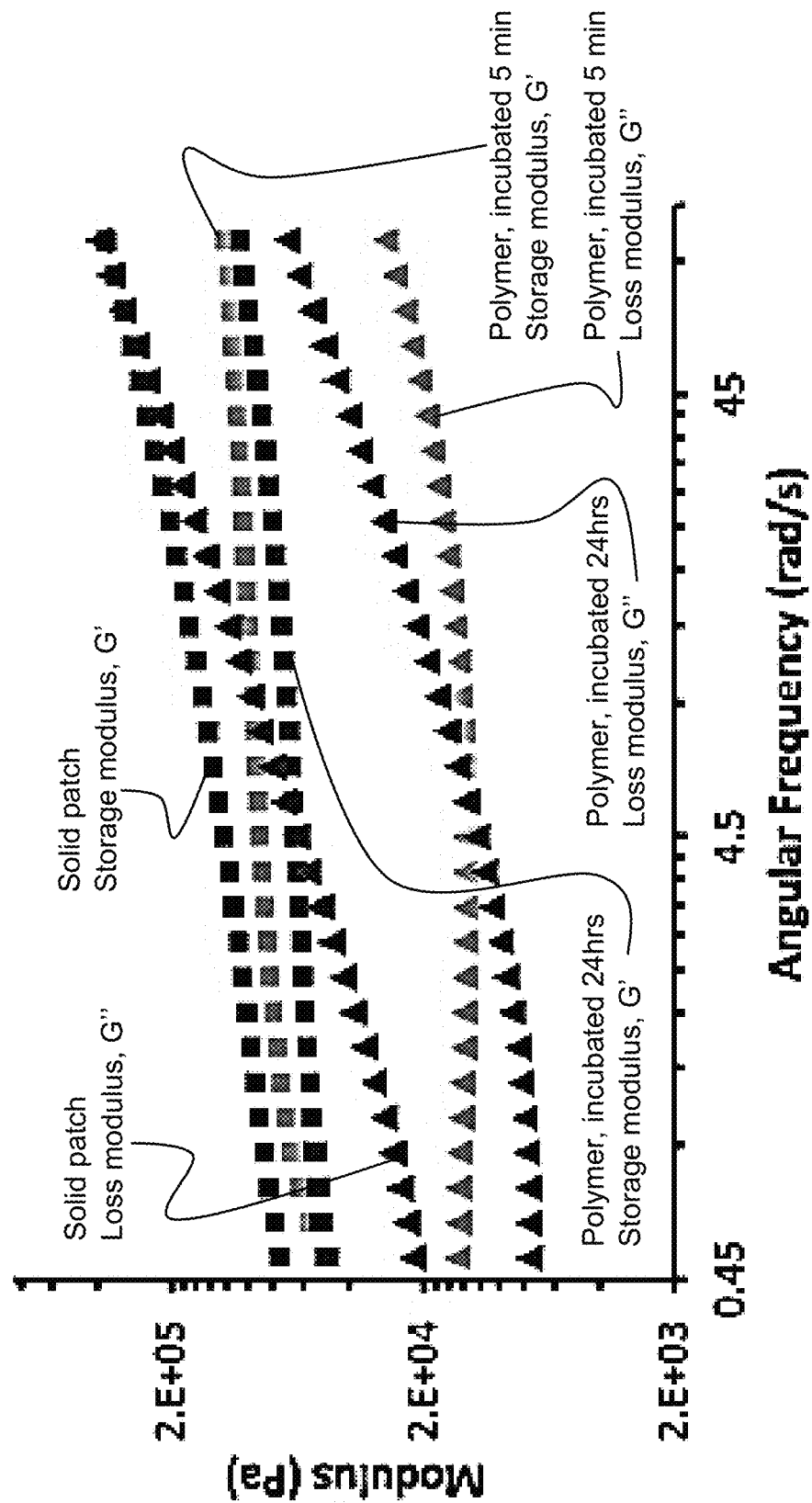
FIGS. 2D and 2E compares the storage modulus (squares) and the loss modulus (triangles) between solid patches, in-situ synthesized polymer after 5 minutes incubation in PBS at 37° C., and in-situ synthesized polymer after 24 hours incubation in PBS at 37° C., in some embodiments.
Figure 2E:
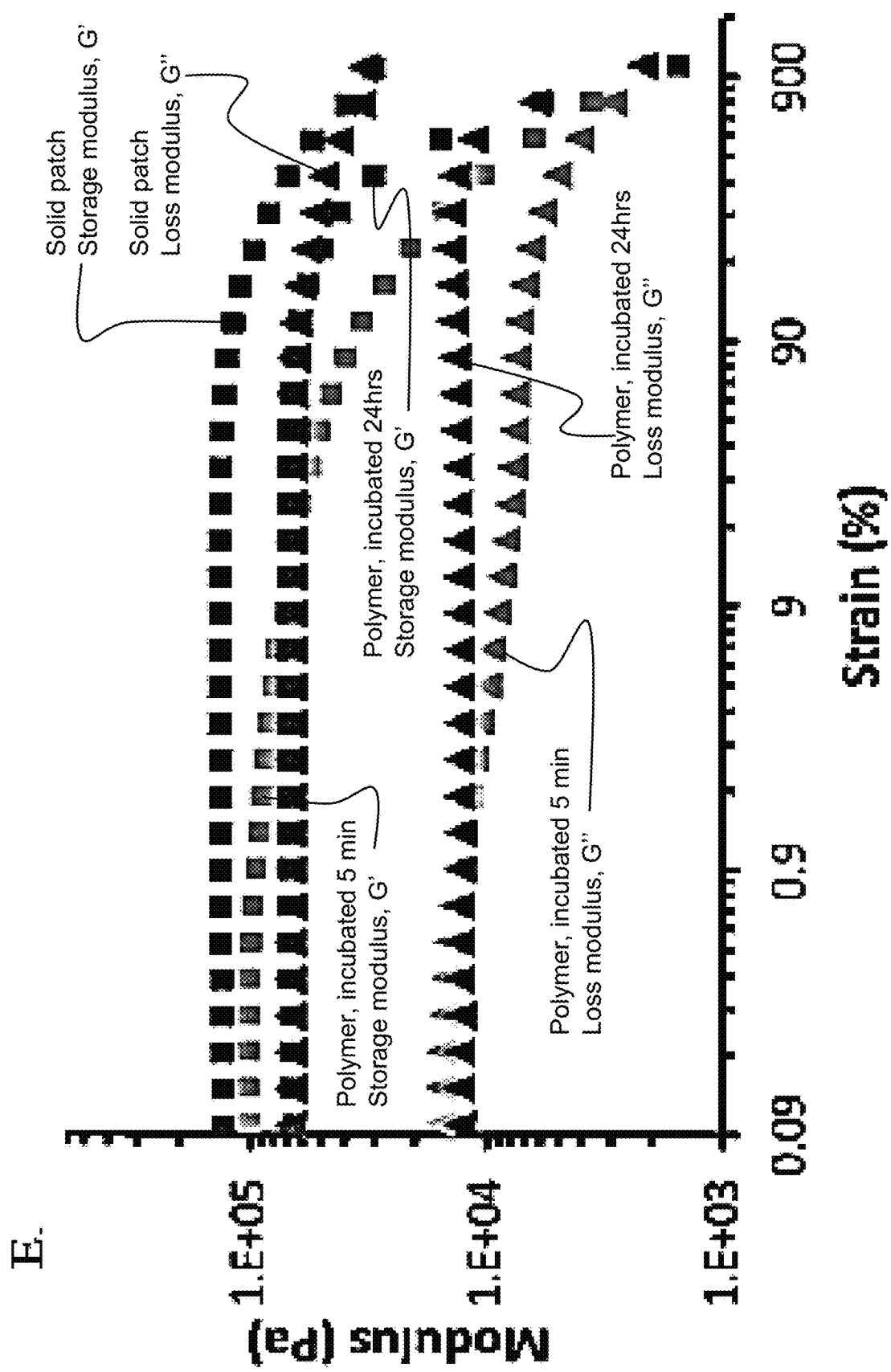

A stress relaxation experiment with an instantaneous strain of 100% shows the polymer relaxes from 576±20 kPa stress to 118±5 kPa within 18 see, thereby highlighting the excellent stress relaxation property of the polymer. Furthermore, the creep test shows that the polymer can bear an 80 kPa load for an extended time without undergoing deformations. Next, the self-healing property of the polymer was investigated. The poly($\alpha$-lipoic acid) copolymers are known to undergo fast self-healing due to the presence of dynamic covalent bonds. Therefore, to test the healing efficiency, a polymer film was cut into two pieces and then carefully brought into contact for 2 min at 37° C. and equilibrated for 5 min at room temperature before measurements. Interestingly, over 60% recovery efficiency was achieved within such a short interval, indicating high chain mobility within the polymer network (See FIG. 2C). Afterward, the rheological properties of the polymer were also analyzed for both wet and thermally processed polymer (See FIG. 2D, 2E). An amplitude sweep analysis of the dry polymer shows an extended viscoelastic region, whereas the wet polymer immediately after polymerization shows a smaller linear viscoelastic region (See FIG. 2E). However, an extended viscoelastic region was observed when the polymer was incubated for 24 h (See FIG. 2E). We believe, initially, the polymer network has a lower crosslinking density, and it increases over time and provides higher stability of the network. A frequency sweep, on the other hand, shows only a slight reduction in modulus in the wet state compared to the dry state and was attributed to the lower water uptake by the polymer due to the higher hydrophobicity of the poly ($\alpha$-lipoic acid)(See FIG. 2D).

Example 9. Testing Adhesion Between Biological Tissues as a Replacement for Medical Grade Cyanoacrylate Superglues The $\alpha$-lipoic acid (L1) monomer was combined with the NHS-derivative of the $\alpha$-lipoic acid (L2) in absolute ethanol with a catalytic amount of DMSO. The mixture was applied to two bovine heart tissue surfaces as an atomized spray to evaporate the ethanol and increase the concentration of the mixture. Lap joints were created immediately between the tissue and incubated in PBS for further curing. The adhesive outperformed medical grade cyanoacrylate superglue at higher incubation times. Changing the stabilizer molecule from the NHS-derivative of the $\alpha$-lipoic acid (L2) to the Ac-Gly-OSu-derivative of the $\alpha$-lipoic acid (L3) didn't significantly affect the results. Likewise, doubling the concentration of the NHS-derivative of the $\alpha$-lipoic acid (L2) did not significantly affect the results. Ultrafast polymerization upon contact with a wet tissue surface, combined with high mechanical strength and high stretchability makes the instant technology an attractive alternative to medical-grade cyanoacrylate superglue, for example.

Figure 3A:
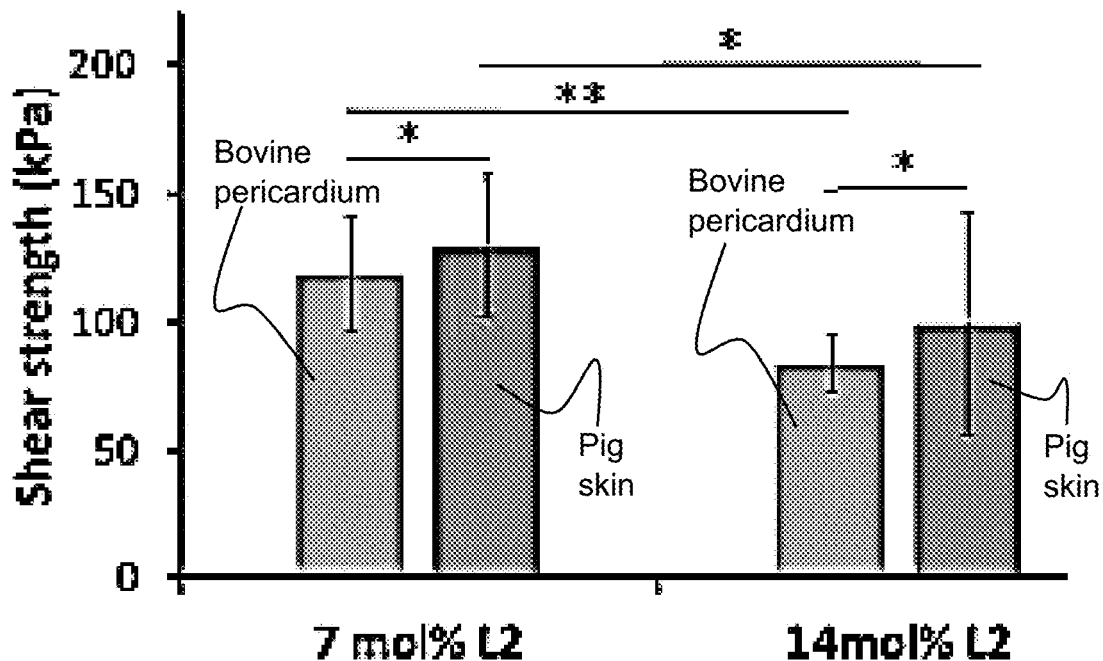
FIG. 3A illustrates a comparison of the lap shear strengths of the adhesive polymer on wet bovine pericardium and pig skin at different concentrations (7 mol % and 14 mol %) of the stabilizer (L2) referred to as the N-hydroxysuccinimide (NHS)-derivative of the α-lipoic acid monomer, in some embodiments. The p value was calculated with a student's t-test in Microsoft Excel (2 array, 2 tails, 2 type). * p>0.05,  p≤0.05, * p≤0.01. No significant difference in the shear strength was observed at the different stabilizer concentrations.

Experimental:

An atomized spray was initially chosen, as it allows for quick evaporation of ethanol to increase the concentration of the mixture rapidly and eliminate any undesired flow of the adhesive solution on the tissue surfaces. A solution of L1 and L2 (7 mol %) was prepared and sprayed on two pieces of tissue surfaces (40 µL in 1 cm$^2$) and the two pieces were immediately brought into contact. After forming the lap joints, they were incubated for 2 minutes in PBS at 37° C. for further curing of the polymer network. The lap shear strength after 2 minutes on wet bovine pericardium tissue was >100 kPa, which was only slightly lower than medical-grade superglue (See FIG. 3A). Interestingly, when the lap joints were incubated for 24 hours in PBS at 37° C., the shear strength increased almost two-fold to >200 kPa, thus outperforming medical-grade superglue (See FIG. 3A). The failure mode analyses of the lap joints was performed by applying N-bromo succinimide to the failed tissue surfaces to visually indicate by charge transfer complexation of disulfide functionality and therefore the presence of adhesive polymer. This analysis revealed cohesive failure both at 2 min and 24 h incubation, suggesting strong adhesion at the tissue-adhesive interfaces. The enhanced lap shear strength at longer incubation time is consistent with the enhanced cohesive strength of the polymer network as observed in the rheology analysis of the wet polymer (see FIG. 2E).

Figure 3B:
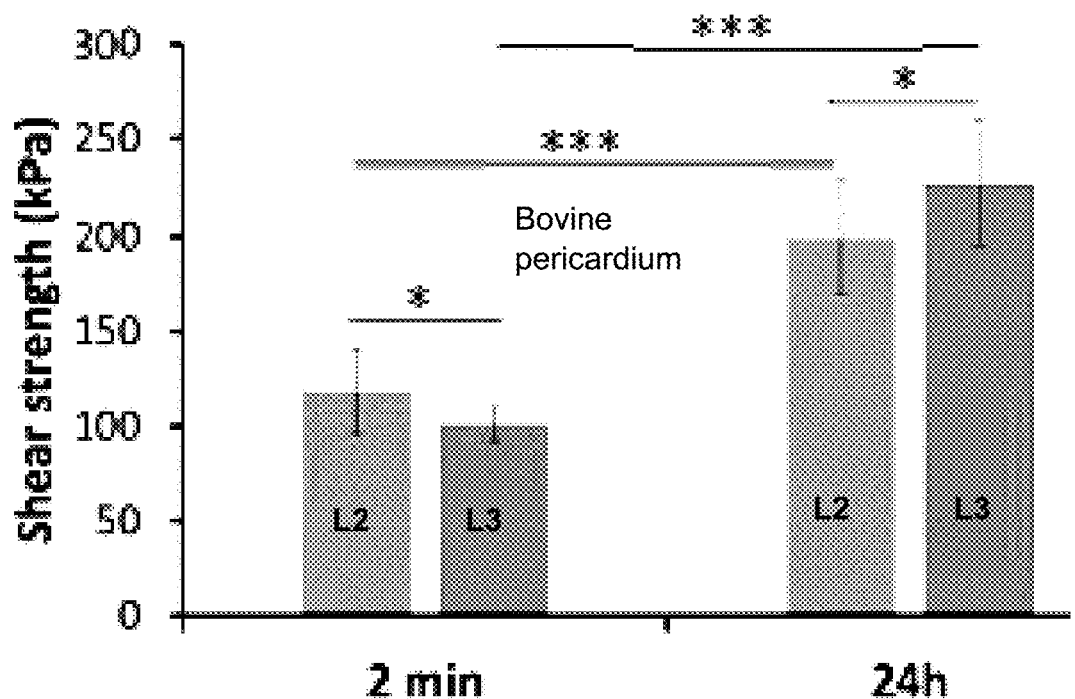
FIG. 3B illustrates a comparison of the lap shear strengths of the adhesive polymer on wet bovine pericardium when using a different stabilizer (L3) that is a second derivatized α-lipoic acid monomer referred to as the Gly-OSu derivative of α-lipoic acid, the lap shear strength taken after an incubation of 2 minutes in PBS and an incubation of 24 hours in PBS, in some embodiments. The p value was calculated with a student's t-test in Microsoft Excel (2 array, 2 tails, 2 type). * p>0.05,  p≤0.05, * p≤0.01. An almost two-fold increase was observed between the 2 minutes of incubation and the 24 hours of incubation.

Lap shear tissue adhesion was also performed with L3 on both wet bovine pericardium and pig skin. Like L2, a high shear strength was also observed within 2 min incubation in PBS, and an almost two-fold increase was observed after 24 hours of incubation (See FIG. 3B). Similarly, the peel test analyses on the pig skin also showed excellent peel strength within 5 min incubation in PBS and increased significantly after 24 h.

To study the effect of stabilizer concentration on tissue adhesion strength, another lap shear test was performed with a higher L2 concentration (14 mol %). No significant difference in the shear strength was observed.

Example 10. Testing Adhesion, Namely Heterobonding Between Biological Tissues and Various Substrates that Include Hard, Soft, Organic, and Inorganic Substrates These substrates include stainless steel (SS), titanium dioxide (TiO2), glass (SiO2), nylon, high density polyethylene (HDPE), polydimethylsiloxane (PDMS), and polytetrafluoroethylene (PTFE). The $\alpha$-lipoic acid (L1) monomer was combined with the NHS-derivative of the $\alpha$-lipoic acid (L2) in absolute ethanol with a catalytic amount of DMSO. The mixture was applied to form joints between heart tissue and the substrates. There was excellent bonding in all joints, including the HDPE and PTFE substrates, meaning that the adhesives can replace the medical grade cyanoacrylates, as well as offer the surprising feature that they're expected to work well in vascular grafting procedures.

Experimental:

A lap joint was fabricated using the ethanolic adhesive precursor of L1 and L2, where wet bovine pericardium tissue was taken as one component of the lap joint, whereas the other component was selected from a range of hard and soft, organic and inorganic substrates. Interestingly, excellent adhesion strengths were observed with both metallic and polymeric substrates (See FIG. 3E). This result suggests the remarkable ability of our adhesive to mediate bonding on various medical devices to tissue. It is also worth mentioning that the high adhesion strength of tissue with polymeric substrates like PE and PTFE opens the possibility of using the newly developed adhesives in vascular grafting.

Example 11. Comparing the Strength of 2 Different Adhesives on Pig Skin and Cow Heart Tissue This example compares the strength of 2 different adhesives on pig skin and cow heart tissue, namely comparing (i) a brushing of the stable liquid precursor having L1, L2, and L4 in DMSO solution ("the brush adhesive") to (ii) a spraying of the adhesive having the L1 and L2 in absolute ethanol solution ("the spray adhesive"). At 2 minutes incubation in PBS the adhesion strengths between the 2 different adhesives are comparable. At 24 hours incubation in PBS, the spray adhesive was significantly stronger than the brush adhesive, assumed due to the lower carboxylic acid concentration in the stable liquid precursor used in the brush adhesive due to the addition of the conjugate base of the lipoic acid (L4). Even with the lower adhesion strength, however, the brush adhesive remains comparable to the medical grade cyanoacrylate adhesive.

Experimental:

The shear strength of the ethanol-free liquid precursor was also tested on wet bovine pericardium and pig skin. The lap joints were prepared by brushing (5 mg in 1 cm$^2$) the liquid precursor of L1, L2 and L4 mixture on the wet tissue surface, followed by incubation in PBS for 2 min and 24 hours at 37° C. The lap shear measurements after 2 min incubation in PBS shows a high adhesion strength with pig skin and was comparable to spray mode. A slightly lower adhesion strength was observed in the case of the bovine pericardium (See FIG. 3D). A much higher difference in shear strength was observed among spray and brush modes after 24 hours of incubation in both pig skin and bovine pericardium. We believe the lower carboxylic acid concentration in liquid precursor reduced the number of noncovalent interactions with tissue surface and within the polymer network, therefore resulting in lower adhesion strength than the spray mode of application. Even though the brush mode shows lower adhesion strength than the spray, it is still comparable to medical-grade cyanoacrylate.

Example 12. Testing the Adhesion Strength of the Solid Polymer Patch Made from a Solution of the α-Lipoic Acid (L1) Monomer in Absolute Ethanol Added to a Solution of the NHS-Derivatized α-Lipoic Acid (L2) in DMSO The solution of the α-lipoic acid (L1) monomer in absolute ethanol added to a solution of the NHS-derivatized α-lipoic acid (L2) in DMSO was added to PBS, dried, and formed as a patch as described above. After only 2 minutes curing time, the solid patch was not as strong as the liquid spray and liquid brush adhesives of Example 11, but the shear strength of the solid patch approached that of the liquid spray and liquid brush adhesives after 24 hours. It is suspected that the dynamic covalent bonds in the solid patch are hindered by the high hydrophobicity of the patch and low mobility of the polymers, but the molecules are mobile and reorganize over the 24 hours to interact with the tissue surface. The lower strength observed in the first 2 minutes was resolved by spraying or brushing the solid polymer patch with a liquid form of the adhesive that was made by combining the α-lipoic acid (L1) monomer in absolute ethanol with a solution of the Ac-Gly-OSu-derivatized α-lipoic acid (L3) in DMSO.

Figure 3C:
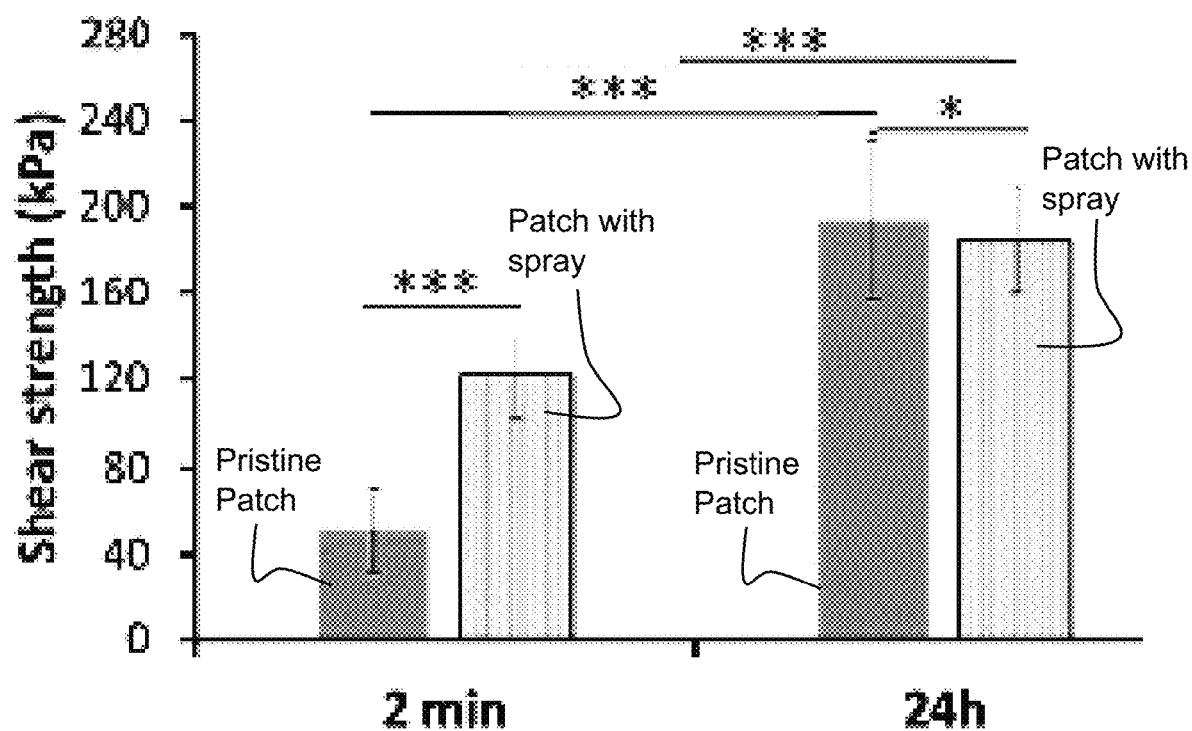
FIG. 3C illustrates a comparison of shear strength between a pristine solid adhesive patch and the patch also having an adhesive liquid spray, the comparison made on wet bovine pericardium taken after an incubation of 2 minutes in PBS and an incubation of 24 hours in PBS, in some embodiments. The p value was calculated with a student's t-test in Microsoft Excel (2 array, 2 tails, 2 type). * p>0.05,  p≤0.05, * p≤0.01. The addition of the spray should a very significant difference at 2 minutes, but there was no significant difference at 24 hours. Without intending to be bound by any theory or mechanism of action, we suspect that the high hydrophobicity and lower chain mobility in the solid state hindered the interaction of the polymer surface with wet tissue. Likewise, we suspect that the presence of highly dynamic covalent bonds in the network allows the reorganization of the network to obtain favorable interaction with the tissue surface; hence, the shear strength increases over time.
Figure 3D:
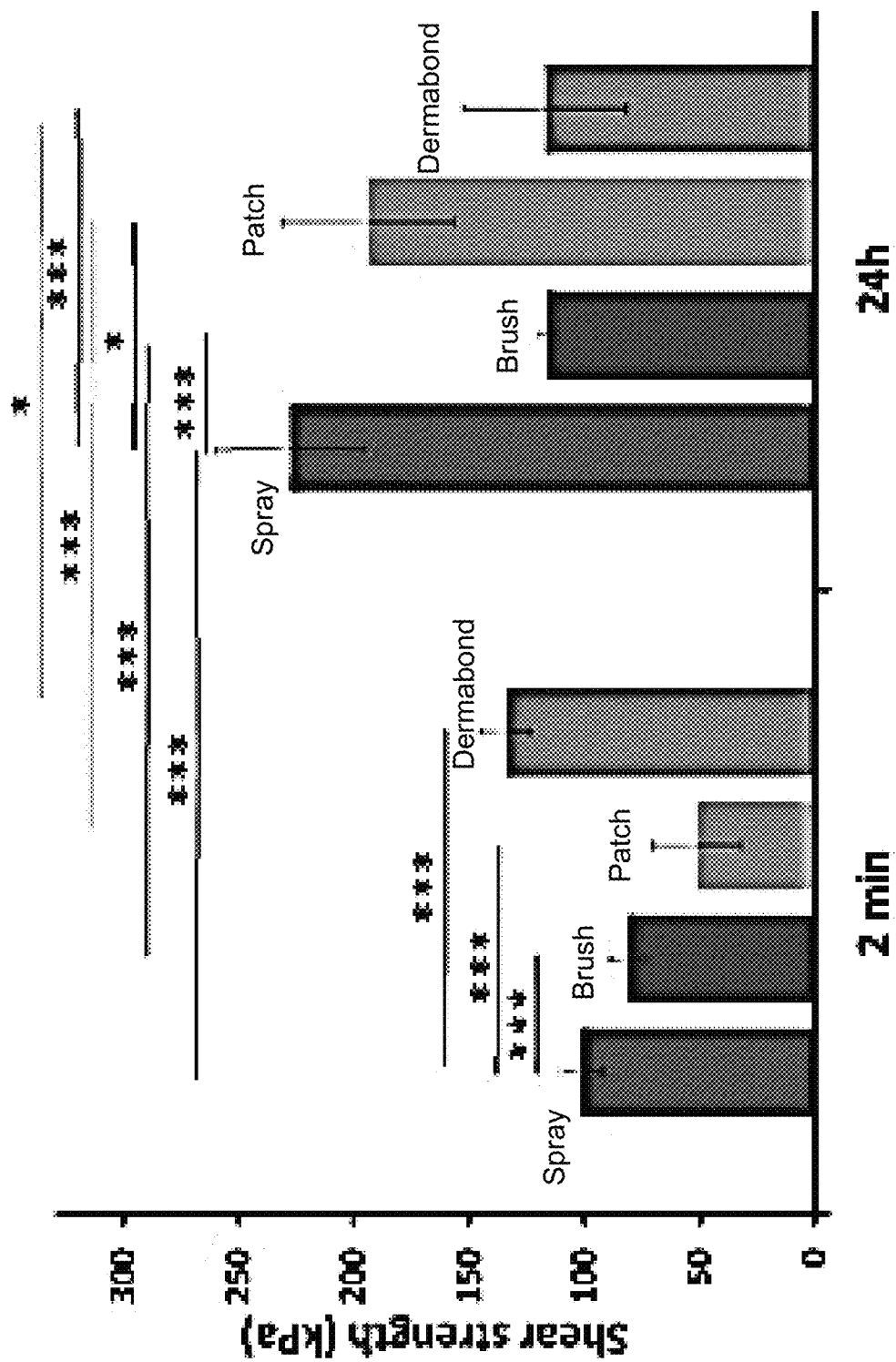
FIG. 3D illustrates a comparison of shear strength of the adhesive on wet bovine pericardium when applied using a spray application, brush application, and a solid adhesive patch, wherein, the shear strengths of all were compared to the shear strength of Dermabond, in some embodiments. The p value was calculated with a student's t-test in Microsoft Excel (2 array, 2 tails, 2 type). * p>0.05,  p≤0.05, * p≤0.01. The adhesive contains α-lipoic acid monomer (L1), an NHS-derivatized α-lipoic acid (L2) as a first stabilizer, and the conjugate base of the α-lipoic acid monomer (L4) to help stabilize the "precursor" from an undesired polymerization. At 2 minutes incubation in PBS the adhesion strengths between the 2 different adhesives are comparable. At 24 hours incubation in PBS, the spray adhesive was significantly stronger than the brush adhesive, assumed due to the lower carboxylic acid concentration in the stable liquid precursor used in the brush adhesive due to the addition of the conjugate base of the lipoic acid (L4). Even with the lower adhesion strength, however, the brush adhesive remains comparable to the medical grade cyanoacrylate adhesive.
Figure 3E:
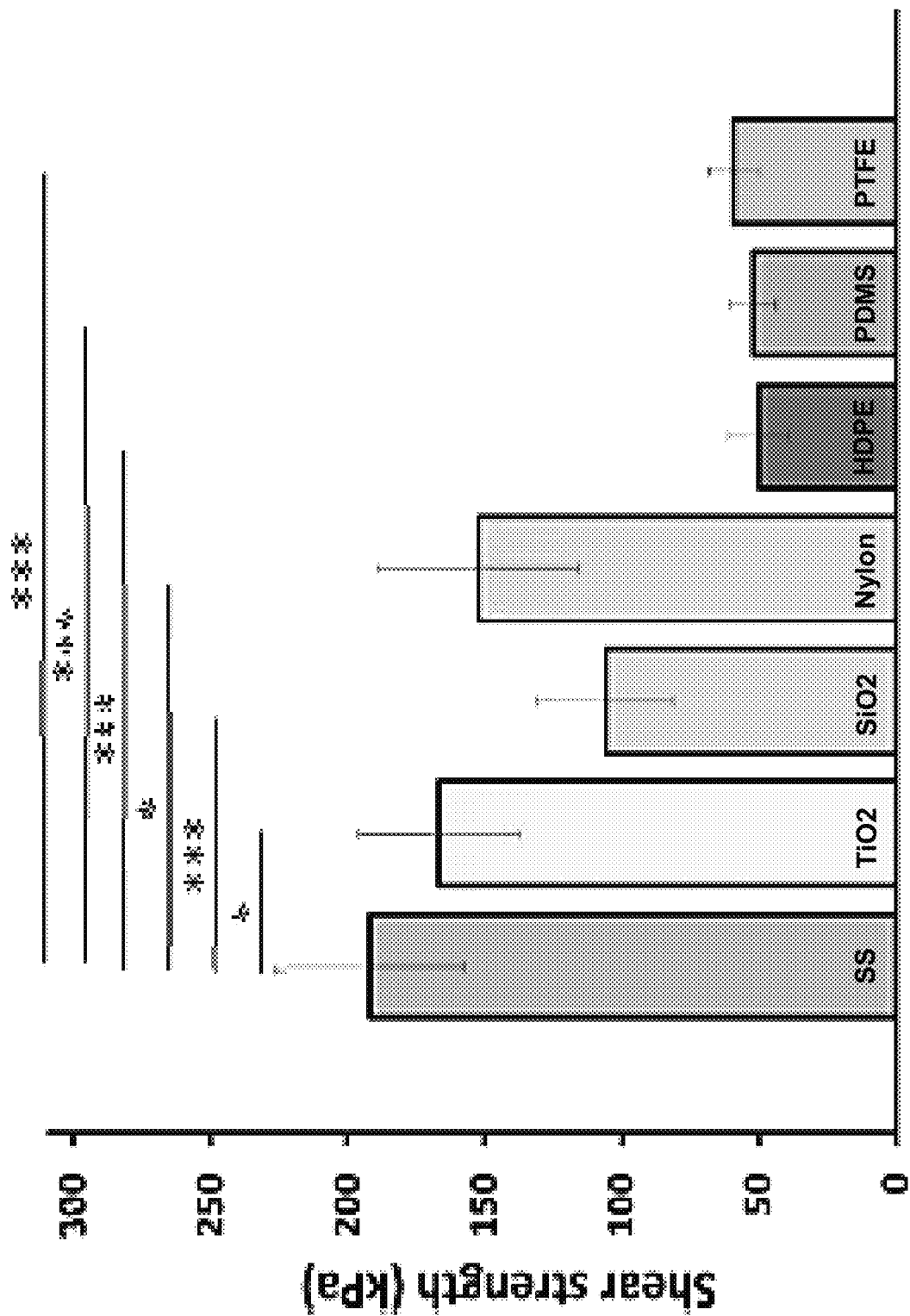
FIG. 3E illustrates a comparison of shear strength of the adhesive when bonding between wet bovine pericardium and several different surfaces after 5 minutes incubation in PBS, the surfaces being stainless steel (SS), titanium dioxide (TiO2), silicate glass (SiO2), Nylon, high density polyethylene (HDPE), Polydimethylsiloxane (PDMS, a silicone polymer), and Poly(tetrafluoroethylene) (PTFE, TEFLON), in some embodiments. The p value was calculated with a student's t-test in Microsoft Excel (2 array, 2 tails, 2 type). * p>0.05,  p≤0.05, * p≤0.01. Interestingly, and surprisingly excellent adhesion strengths were observed with both metallic and polymeric substrates, showing a remarkable ability of our adhesive to mediate bonding of various medical devices to tissue. Moreover, the high adhesion strength of tissue with polymeric substrates like PE and PTFE opens the possibility of using the adhesives taught herein in vascular grafting.

Experimental:

Contrary to both liquid modes, the solid polymer patch shows significantly lower adhesion strength after 2 min incubation in PBS (see FIG. 3C). However, the shear strength increased significantly after 24 hours of incubation in PBS. Without intending to be bound by any theory or mechanism of action, we suspect that the high hydrophobicity and lower chain mobility in the solid state hindered the interaction of the polymer surface with wet tissue. Likewise, we suspect that the presence of highly dynamic covalent bonds in the network allows the reorganization of the network to obtain favorable interaction with the tissue surface; hence, the shear strength increases over time. To address the low initial patch adhesion strength, we surmised that by spraying or brushing a solid patch with a liquid formulation just before contact with tissue could ensure quick and efficient adhesion of patch to the tissue surface. To test this hypothesis, another lap shear test was performed where the patch was sprayed with precursor solution immediately prior to forming the lap joints. As anticipated, a high adhesion strength was observed within 2 min incubation in PBS and was comparable with the spray mode of application (see FIG. 3C).

Example 13. Sealing an Injured Lung or Stomach Tissue with the Solid Polymer Patch Made from a Solution of the α-Lipoic Acid (L1) Monomer in Absolute Ethanol Added to a Solution of the NHS-Derivatized α-Lipoic Acid (L2) in DMSO The combined solution of the α-lipoic acid (L1) monomer in absolute ethanol added to a solution of the NHS-derivatized α-lipoic acid (L2) in DMSO was added to PBS, dried, and formed as a patch as described above. The patch was tested with and without the addition of a liquid adhesive spray. An air-filled porcine lung, and a fluid-filled porcine stomach, were effectively sealed with the solid polymer patch when spraying the solid polymer patch with a liquid form of the adhesive before use, the spray being a liquid form of the adhesive that was made by combining the α-lipoic acid (L1) monomer in absolute ethanol with a solution of the Ac-Gly-OSu-derivatized α-lipoic acid (L3) in DMSO. The lungs were tested for air leaks with a soap and water spray and none were found.

Figure 3F:
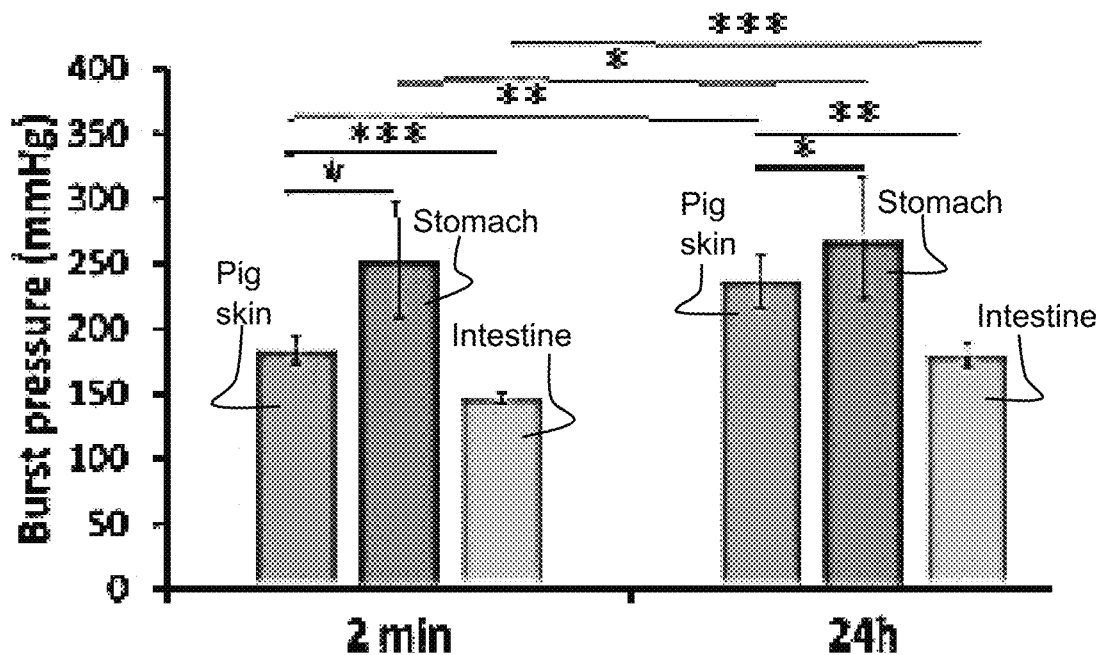
FIG. 3F illustrates a comparison of burst strength of a solid adhesive patch and liquid spray combination on wet pig skin, stomach, and intestine after an incubation of 2 minutes in PBS and an incubation of 24 hours in PBS, in some embodiments. The p value was calculated with a student's t-test in Microsoft Excel (2 array, 2 tails, 2 type). * p>0.05,  p≤0.05, * p≤0.01. The data shows at least that the patch, with or without the addition of liquid adhesive before application, provides a rapid and effective tissue adhesion and sealing without burst.
Figure 3G:
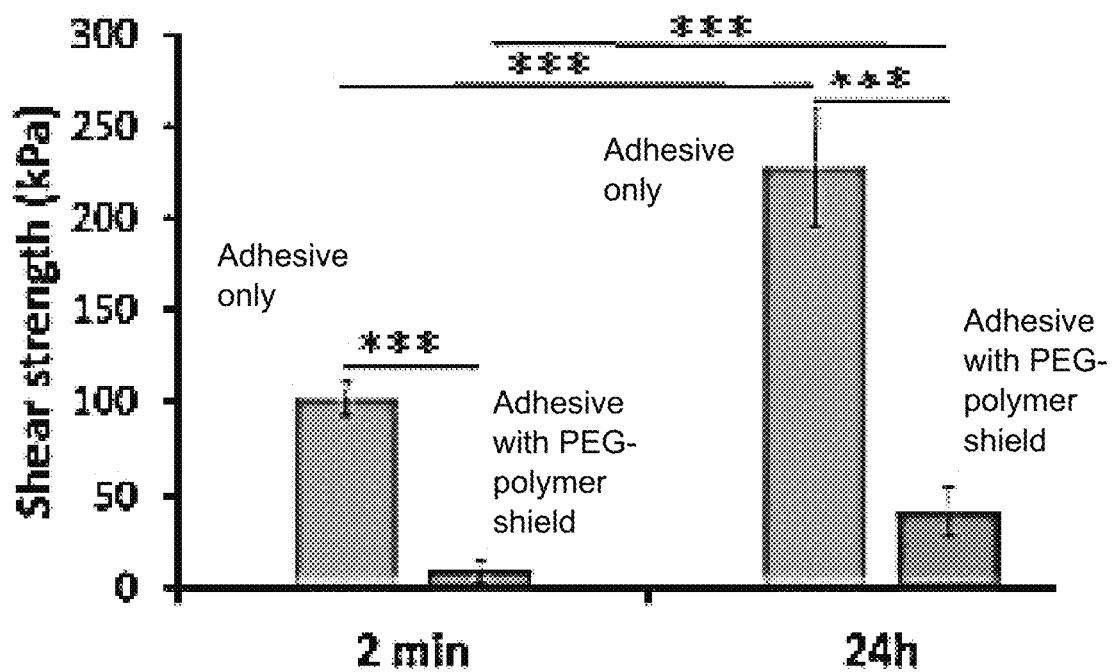
FIG. 3G illustrates a comparison of shear strength comparison with and without non-adhesive spray containing a PEG-derivatized poly(α-lipoic acid) on a wet bovine pericardium after an incubation of 2 minutes in PBS and an incubation of 24 hours in PBS, in some embodiments. The p value was calculated with a student's t-test in Microsoft Excel (2 array, 2 tails, 2 type). * p>0.05,  p≤0.05, * p≤0.01. The data shows at least that use of a lipoic-acid-functionalized, antifouling polymer, on top of an in-situ formed poly(α-lipoic acid) adhesive could be used to prevent unwanted biofouling or post-surgical adhesion formation.
Figure 3H:
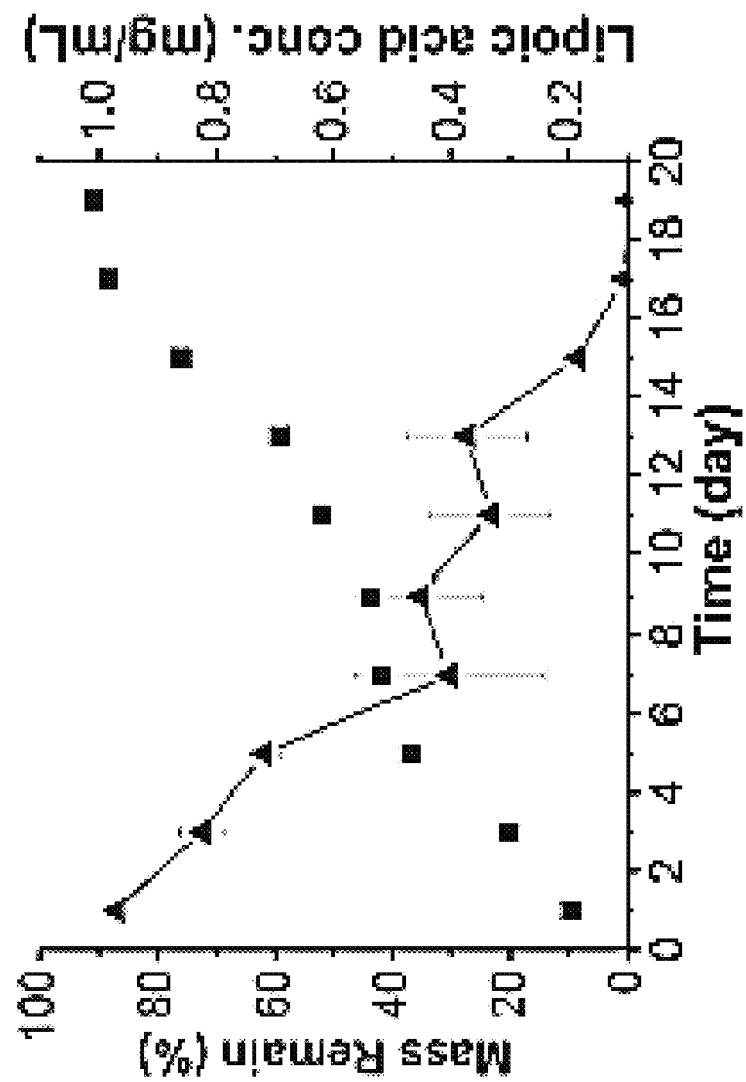
FIG. 3H illustrates the polymerization and depolymerization of poly(α-lipoic acid) using glutathione (GSH)-mediated degradation of the polymer, in some embodiments. The p value was calculated with a student's t-test in Microsoft Excel (2 array, 2 tails, 2 type). * p>0.05,  p≤0.05, * p≤0.01. The data shows at least that the polymers are recyclable, and can be recycled efficiently due to the ability to degrade efficiently from the polymer form to the individual monomers.
Figure 3J:
FIGS. 3I and 3J illustrate effective patching of a punctured porcine stomach with a solid adhesive patch, in some embodiments.
Figure 3I:
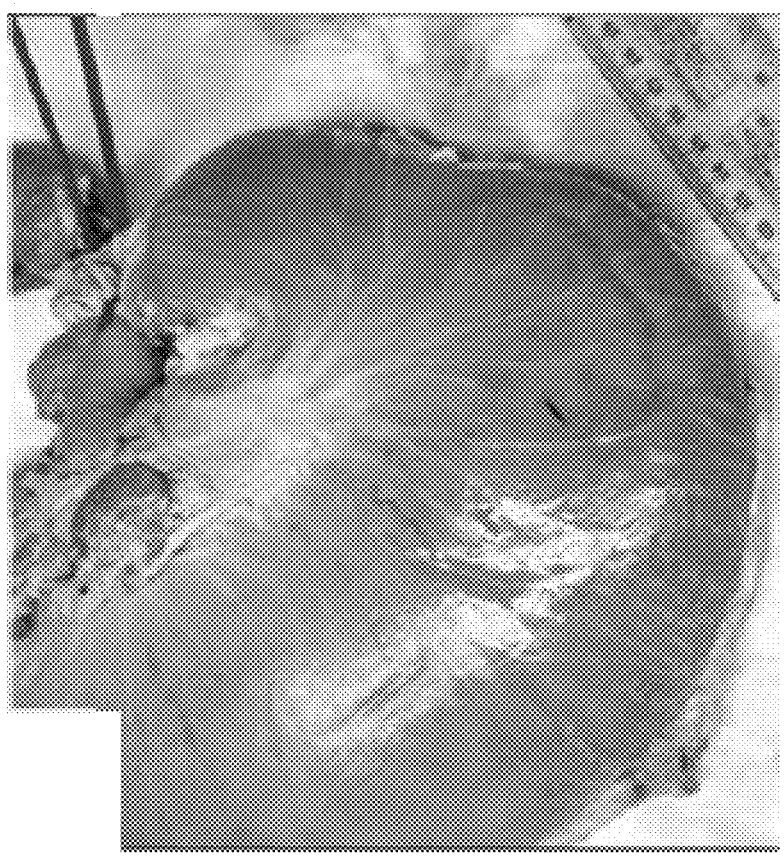
Figure 3L:
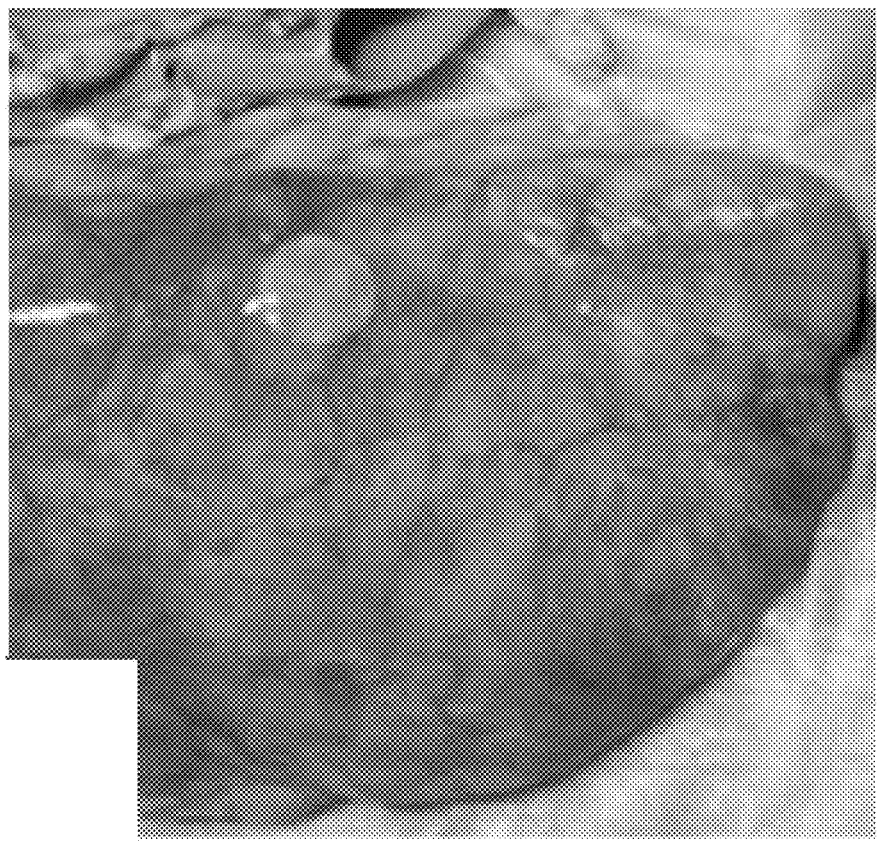
FIGS. 3K and 3L illustrate effective patching of a punctured porcine lung with a solid adhesive patch, in some embodiments.
Figure 3K:

Experimental:

A range of ex-vivo sealing experiments with fresh porcine stomach and lung were performed. The solid polymer patch (diameter 15 mm) combined with the spray can successfully form an airtight seal of a 5 mm incision in a damaged lung lobe (see FIG. 3K, 3L). Furthermore, to mimic an injury model, a fresh and highly perforated porcine lung was obtained from a slaughterhouse and repaired with bovine pericardium patch grafted to the lung with the aid of adhesive precursor spray. The spray adhesive shows excellent efficacy in sealing the air leaks within 2 min of application, as verified with soap water spray. Similar experiments were also performed with a liquid-filled stomach and solid adhesive patch obtained from L1 and L2 mixture. The spray (L1, L3 mixture), in combination with the solid adhesive patch, bovine pericardium, and PTFE films, provided leakage-free sealing of the damaged stomach.

Example 14. Sealing Skin, Intestine, and Stomach Tissue with the Solid Polymer Patch Made from a Solution of the α-Lipoic Acid (L1) Monomer in Absolute Ethanol Added to a Solution of the NHS-Derivatized α-Lipoic Acid (L2) in DMSO The combined solution of the α-lipoic acid (L1) monomer in absolute ethanol added to a solution of the NHS-derivatized α-lipoic acid (L2) in DMSO was added to PBS, dried, and formed as a patch as described above. The patch was tested with and without the addition of a liquid adhesive spray. Burst pressure was tested at 2 minutes and 24 hours incubation time in PBS, and the data shows that the patch, with or without the addition of liquid adhesive before application, provides a rapid and effective tissue adhesion and sealing without burst.

Experimental:

The burst strength of the solid adhesive patch (L1 and L2) with and without spray was investigated on wet porcine skin, small intestine, and stomach. The pristine patch exhibits 123±32 mmHg burst pressure on wet porcine skin after 2 min of pressing time, increasing to 195±12 mmHg after 24 h incubation in PBS at 37° C. (see FIG. 3F). On the other hand, the patch with spray shows 184±10 mmHg and 237±20 mmHg burst pressure on wet porcine skin, 146±4 mmHg and 180±9 mmHg burst pressure on the porcine small intestine, 252±43 mmHg and 268±45 mmHg burst pressure on the porcine stomach after 2 min and 24 h incubation in PBS respectively (see FIG. 3F). Altogether, these data establish the excellent potential of the newly developed adhesive to provide rapid and effective tissue adhesion and sealing.

Example 15. Block Undesired Adhesion from Targeted Areas of a Solid Adhesive Patch This example shows that portions of the polymer patch can be coated with PEG-polymer derivatized with a disulfide monomer to block undesired adhesion from targeted areas of the patch. A telechelic PEG polymer was derivatized with α-lipoic acid monomer and sprayed on an otherwise adhesive surface of a solid polymer patch made from a solution of the α-lipoic acid (L1) monomer in absolute ethanol added to a solution of the NHS-derivatized α-lipoic acid (L2) in DMSO. After spraying on the PEG polymer, a lap joint was formed with the solid patch and incubated in PBS at 37° C. Effective and targeted shielding of the adhesive occurred with use of the PEG layer at both 2 minutes and 24 hours. It was demonstrated that the dynamic property of the polymer could be exploited to prepare a non-adhesive free surface to avoid undesired tissue bonding to the free surface of the adhesive. The application of a lipoic-acid-functionalized, antifouling polymer, on top of an in-situ formed poly(α-lipoic acid) adhesive could be used to prevent unwanted biofouling or post-surgical adhesion formation.

Experimental:

A telechelic PEG polymer was functionalized with α-lipoic acid and sprayed on top of a newly formed adhesive layer before forming the lap joints and incubating in PBS at 37° C. Interestingly, lap shear measurement after 2 min and 24 hours incubation shows significantly lower shear strength, indicating efficient shielding of the adhesive layer and successful incorporation of the non-adhesive PEG layer (see FIG. 3G).

Example 16. Testing Biocompatibility of the Adhesives

The following adhesives were biocompatible with NIH 3T3 cells (mouse fibroblast) and human amniotic cells:
1. a solution of the α-lipoic acid (L1) monomer in absolute ethanol added to a solution of the NHS-derivatized α-lipoic acid (L2) in DMSO;
2. α-lipoic acid (L1) monomer in absolute ethanol with a solution of the Gly-OSu-derivatized α-lipoic acid (L3) in DMSO;
3. α-lipoic acid (L1) monomer in a small amount of DMSO, the NHS-derivatized α-lipoic acid monomer (L2), and sodium lipoate (L4) which is a conjugate base of the α-lipoic acid (L1) monomer (L1); and,
4. a solid patch made from a solution of the α-lipoic acid (L1) monomer in absolute ethanol added to a solution of the NHS-derivatized α-lipoic acid (L2) in DMSO, excess phosphate-buffered saline (PBS) was added to create a stable polymer, and the polymer was freeze-dried and compression molded between polydimethylsiloxane (PDMS) coated paper to create the thin film solid adhesive patch.

Figure 4A:
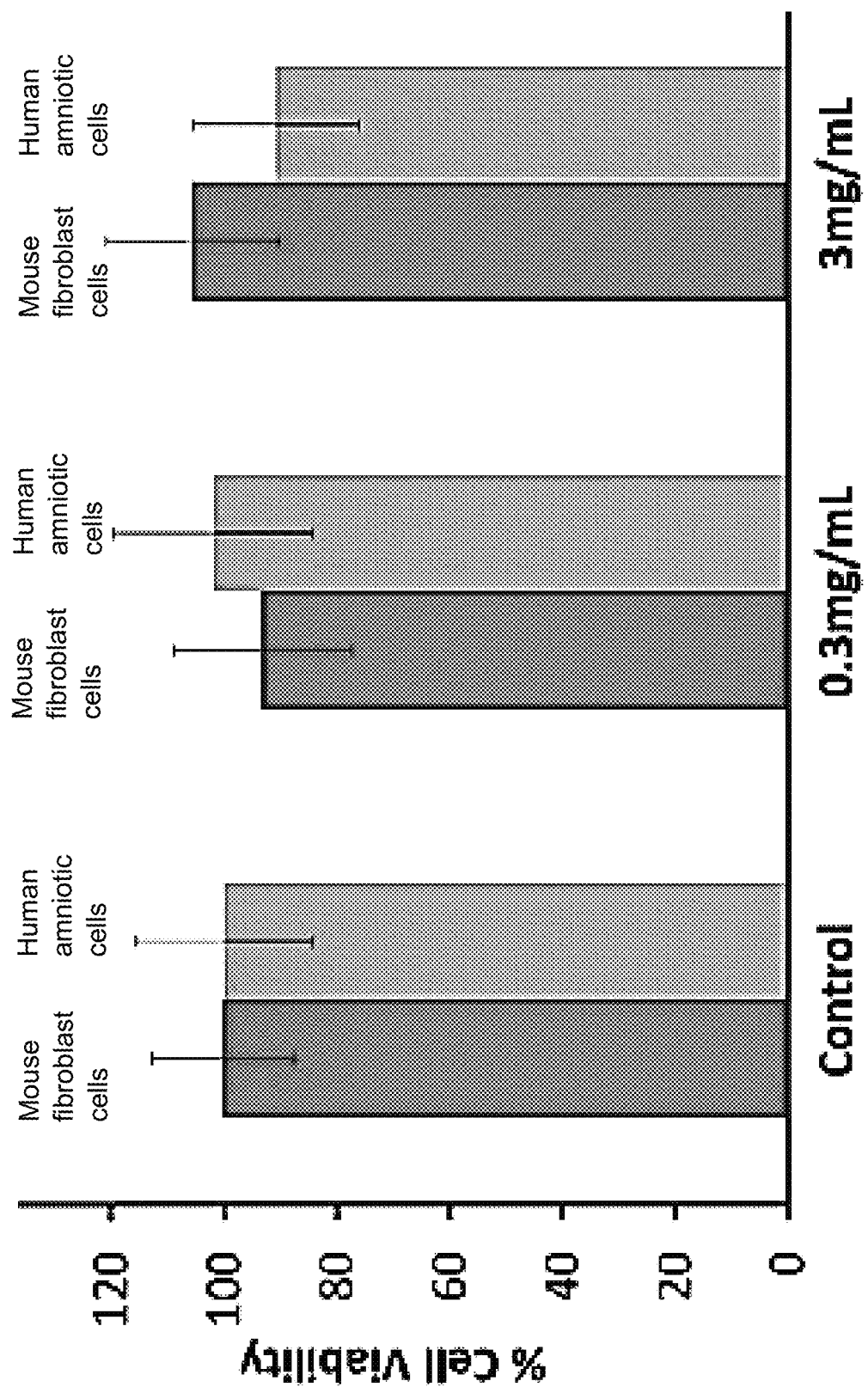
FIG. 4A illustrates an in-vitro biocompatibility profile of in-situ polymerized spray adhesive with mouse fibroblast cells (NIH 3T3) and human amniotic cells after 24 hrs co-culture of the cells with the poly(α-lipoic acid) polymers, in some embodiments. A high density of cells, comparable to growth media controls was observed after the 24 h co-culture with the synthesized polymers, indicating a high biocompatibility of the polymers with the cells.
Figure 4C:
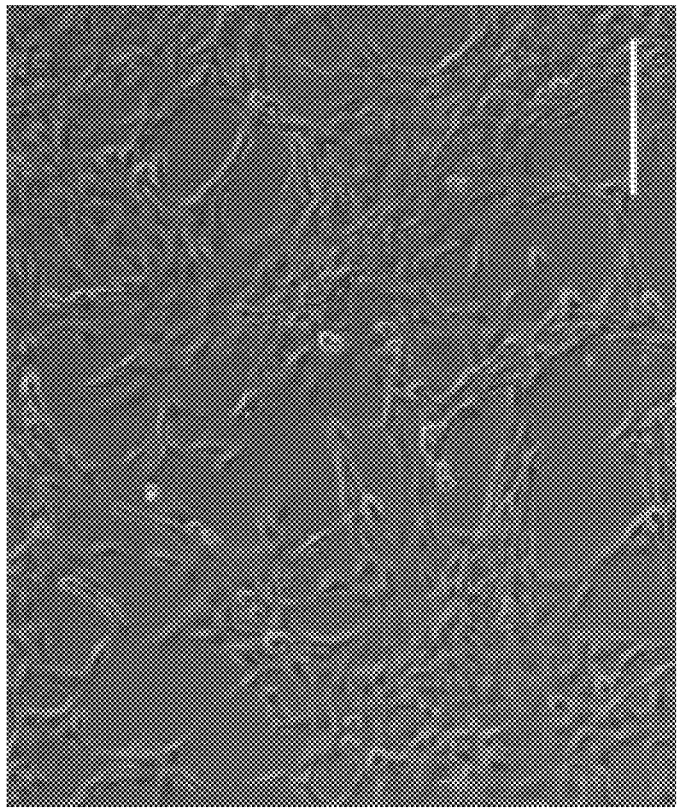
FIGS. 4B and 4C illustrates comparison images of an in-vitro biocompatibility profile of in-situ polymerized spray adhesive with mouse fibroblast cells (NIH 3T3) and human amniotic cells after 24 hrs co-culture of the cells with the 3 mg/ml concentration of poly(α-lipoic acid) polymers, in some embodiments. The images also show a high density of cells, comparable to growth media controls was observed after the 24 h co-culture with the synthesized polymers, indicating a high biocompatibility of the polymers with the cells. The scale bar is 200 um.
Figure 4B:
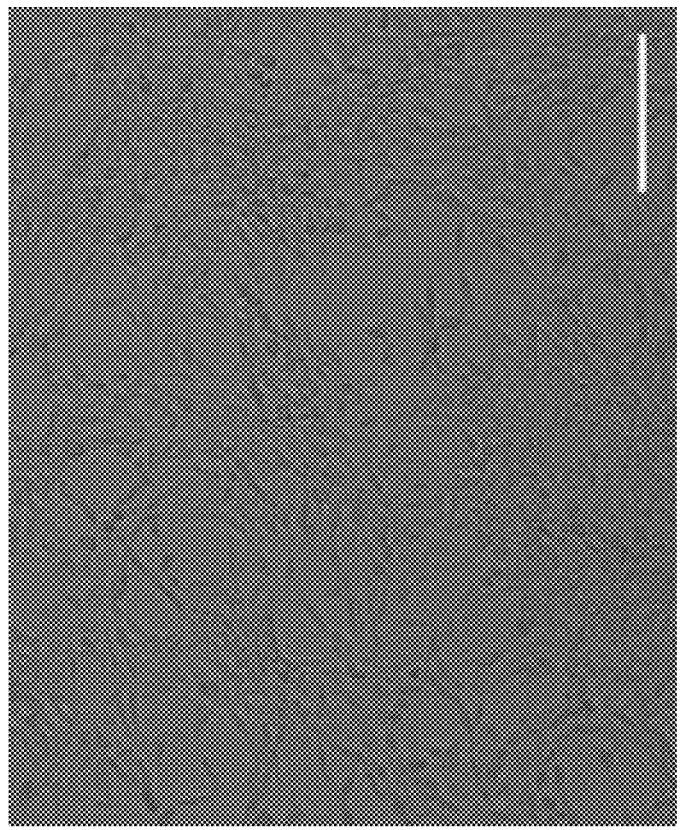
Figure 4D:
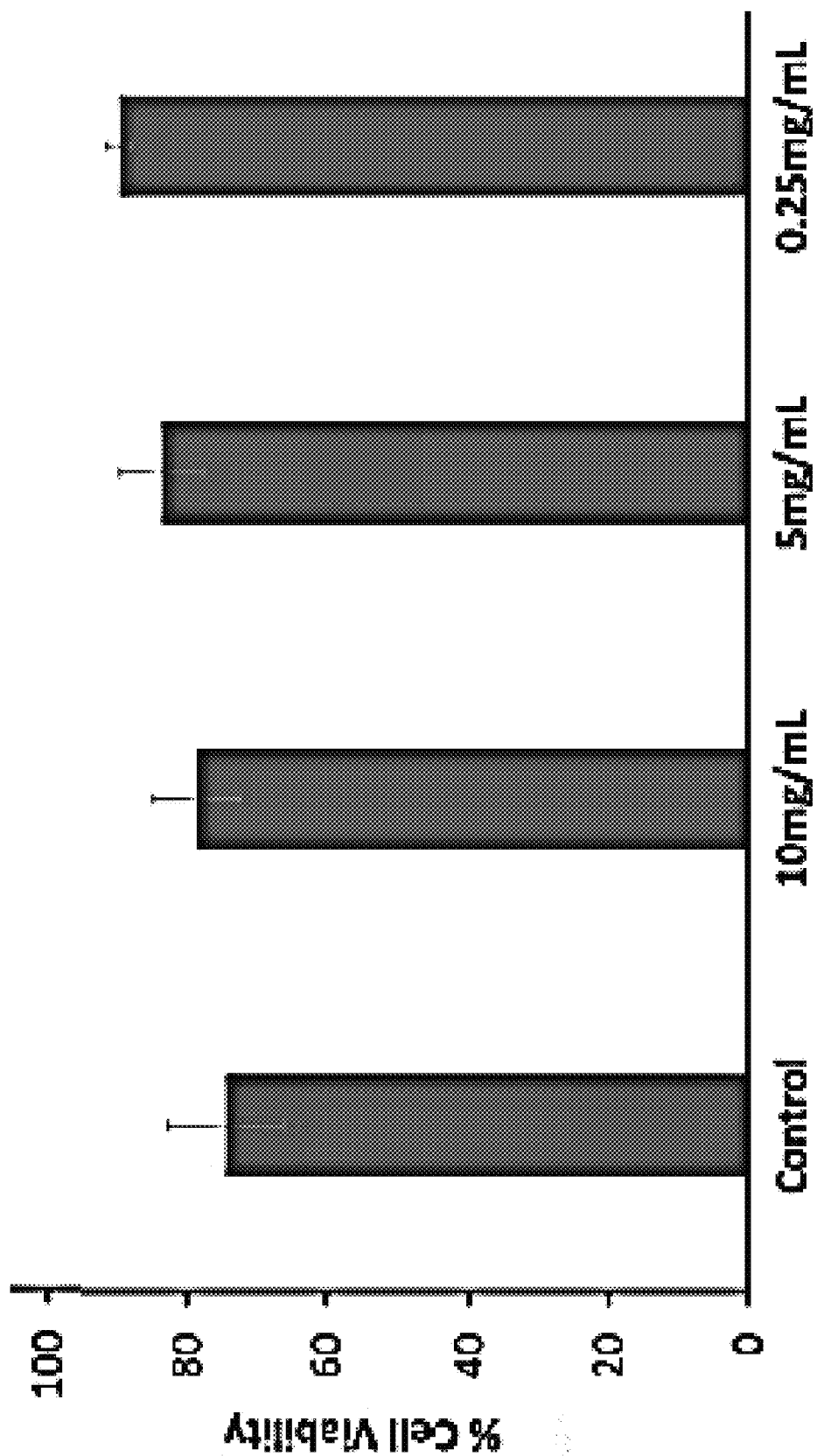
FIG. 4D illustrates a relative cell viability in an in-vitro biocompatibility profile of a solid adhesive patch with mouse fibroblast cells (NIH 3T3) and human amniotic cells after 24 hrs co-culture of the cells with the solid adhesive patch, in some embodiments. A high density of cells, comparable to growth media controls was observed after the 24 h co-culture with the synthesized polymers, indicating a high biocompatibility of the polymers with the cells.

Experimental:

In-vitro cytotoxicity studies of (i) the ethanolic precursor solutions of L1 and L2, (ii) the ethanolic precursor solutions of L1 and L3, (iii) the ethanol-free liquid precursor solutions of L1, L2, and L4, and (iv) the solid polymer (L1 and L2 mixture). The tests were performed on NIH 3T3 cells and human amniotic cells. A high density of cells, comparable to growth media controls was observed after a 24 h coculture with the synthesized polymers (see FIG. 4A, 4B, 4C, 4D). Moreover, a Nile red uptake and live dead assay shows excellent biocompatibility of the solid and in-situ polymerized polymers after 24 h incubation. The in-vitro cytotoxicity study of the in-situ polymerized adhesive with human amniotic cells also confirmed the high biocompatibility of each of the adhesives (see FIG. 4A).

Example 17. Testing Antioxidant Activity of the Adhesives

This example shows that the adhesive solution created from a solution of the α-lipoic acid (L1) monomer in absolute ethanol added to a solution of the NHS-derivatized α-lipoic acid (L2) in DMSO has antioxidant activity. Macrophages were treated with lipopolysaccharide (LPS) in an LPS-induced oxidative stress model, and the macrophages generated reactive oxygen species (ROS) for 1 hour. The ROS formation was completely suppressed, however, when the LPS treatment was combined with the adhesive solution generating polymer in situ with the treated macrophages. This shows that the adhesives have excellent antioxidant activity and efficacy at neutralizing oxidative stress in cells.

Figure 4F:
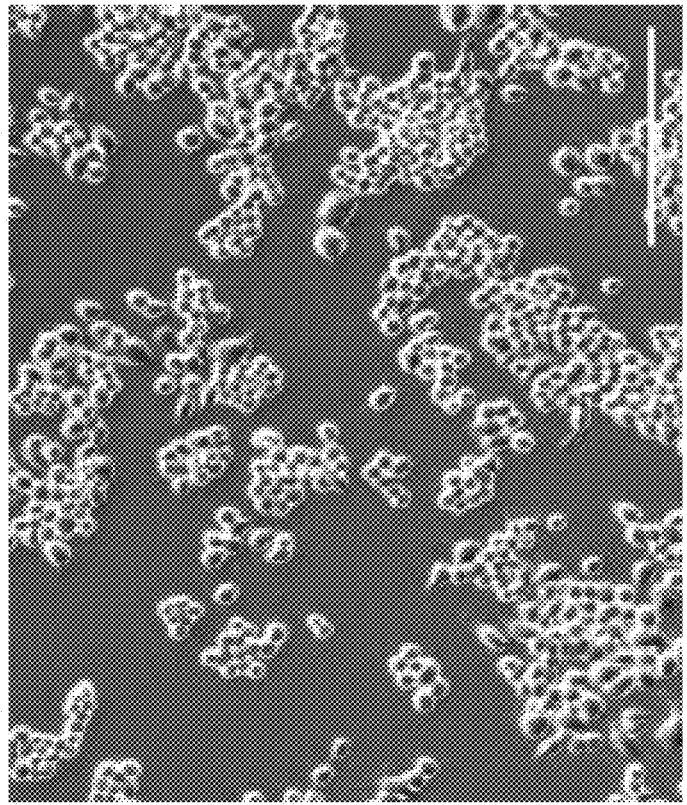
FIGS. 4E and 4F tests the antioxidant property of in-situ synthesized poly(α-lipoic acid) polymers in the presence of macrophages in an lipopolysaccharide (LPS)-induced oxidative stress model, in some embodiments. The macrophages were treated with LPS for 1 hour and imaged for the presence of reactive oxygen species (ROS) as shown FIG. 4E, and that image was compared to an image in FIG. 4F of the macrophages treated with LPS in the presence of the poly(α-lipoic acid) for 1 hour. Green dots are seen in FIG. 4E which is a formation of reactive oxygen species (ROS), whereas the formation of the ROS was completed suppressed in the presence of the poly(α-lipoic acid) as shown by the absence of the green dots in FIG. 4F. The scale bar is 200 um.
Figure 4E:
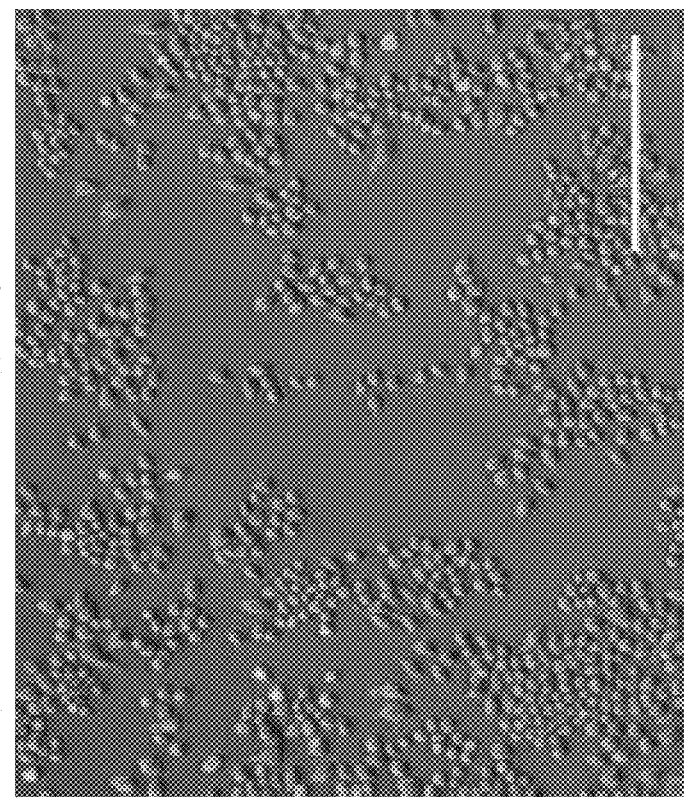
Figure 4J:
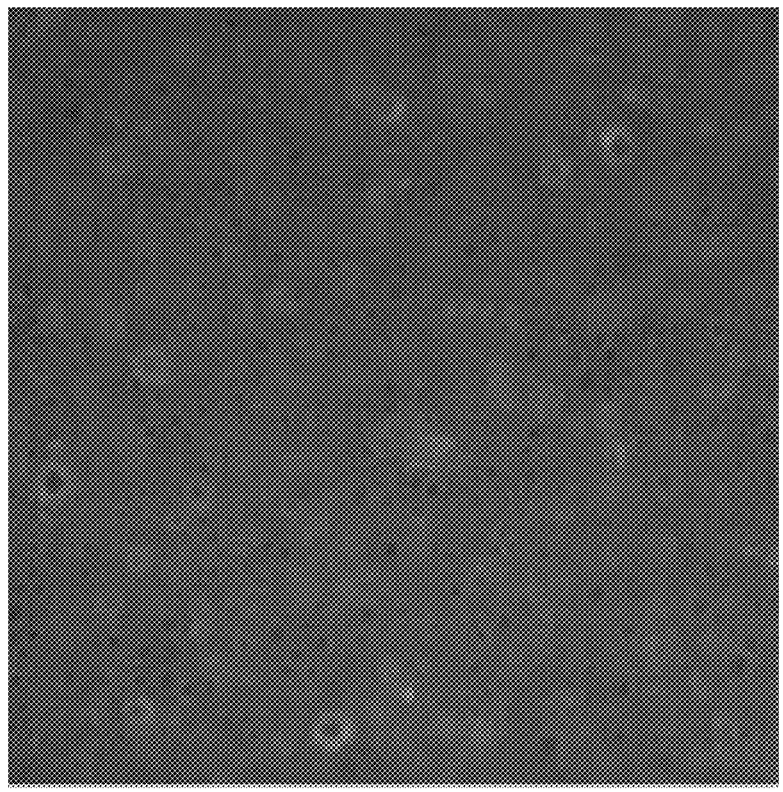
Figure 4I:
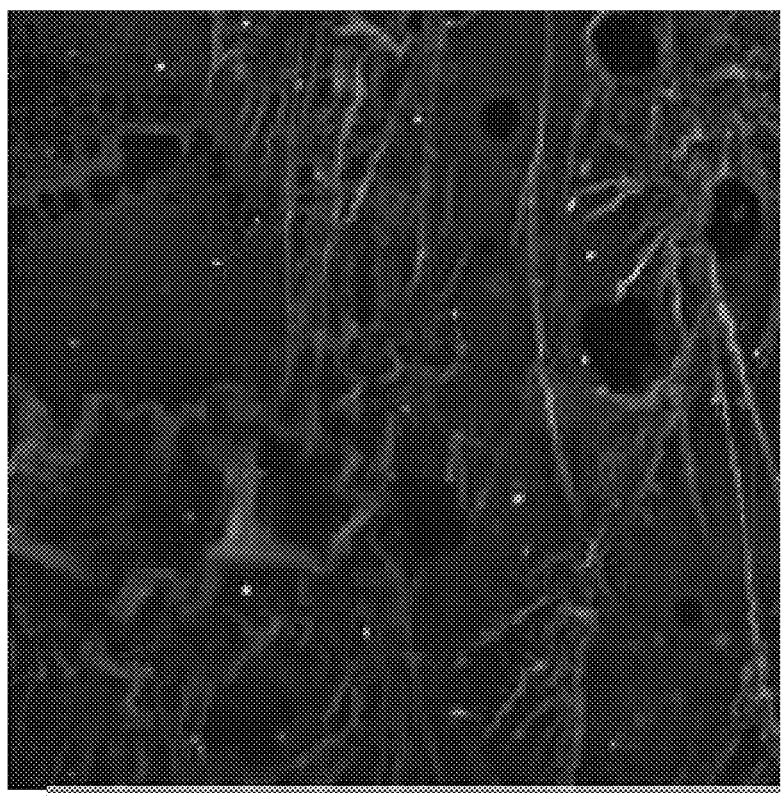

Experimental:

The antioxidant property of the in-situ synthesized polymer from L1 and L2 mixture was investigated using macrophages and an LPS-induced oxidative stress model. The generation of reactive oxygen species (ROS) was observed after the macrophages were treated with LPS for 1 hour (see FIG. 4E). However, the ROS formation was completely suppressed when the macrophages were treated with LPS together with in-situ synthesized polymer (see FIG. 4F). This result indicates the excellent efficacy of the polymer in neutralizing the oxidative stress in cells.

Example 18. Testing the Adhesives as Bacterial Barriers that can Help Prevent Bacterial Infections This example tests the following two adhesives with *Escherichia coli* (*E. coli*):
1. a solid patch made from a solution of the α-lipoic acid (L1) monomer in absolute ethanol added to a solution of the NHS-derivatized α-lipoic acid (L2) in DMSO, excess phosphate-buffered saline (PBS) was added to create a stable polymer, and the polymer was freeze-dried and compression molded between polydimethylsiloxane (PDMS) coated paper to create the thin film solid adhesive patch; and,
2. α-lipoic acid (L1) monomer in absolute ethanol with a solution of the Gly-OSu-derivatized α-lipoic acid (L3) in DMSO.

Adhesive 1 was co-cultured with *E. Coli*, and adhesive 2 formed a polymer in situ that was co-cultured with *E. Coli*. Both of the adhesives showed a significantly lower density of bacteria on the adhesives in their co-cultures than a control culture plate over 24 hours. This shows that the adhesives have excellent barrier efficacy with *E. Coli* and would provide a very desirable antibacterial feature to a wound dressing.

Experimental:

Bacterial infection is one of the major concerns after any surgical intervention or traumatic injuries, and is especially critical for external wound closure to prevent infection into a wound, and for certain internal applications like intestinal perforations and anastomoses, where the repair site must constitute an effective bacterial barrier. Such infections can be avoided by tissue adhesives with bacterial barrier properties. In this context, sulfur is historically known for its excellent antibacterial properties. Hence, we investigated the bacteria barrier properties of the synthesized adhesives with *Escherichia coli*. Interestingly, the coculture of *E. Coli* with solid polymer patch synthesized with L1, L2 mixture and in-situ obtained polymer from ethanolic precursor solution of L1 and L3 exhibits a significantly lower density of bacteria on the polymer compared to the control culture plates (see FIG. 4G, 4H, 4I, 4J). Furthermore, a bacteria barrier study of the polymer shows excellent barrier efficacy after 72 h coculture with *E. Coli*, establishing the potential benefit of the adhesive for wound dressing.

Example 19. Testing the Adhesives for Undesirable Swelling

This example tests the swelling of adhesives. Swelling of tissue adhesives can create problems in some procedures, and the swelling can reduce adhesive strength. This example tests the following two adhesives for mass swelling ratio in an in vitro environment, $(m_s-m_d)/m_d$, where $m_s$ is the swollen mass and $m_d$ is the dry mass:
1. a solid patch made from a solution of the α-lipoic acid (L1) monomer in absolute ethanol added to a solution of the NHS-derivatized α-lipoic acid (L2) in DMSO, excess phosphate-buffered saline (PBS) was added to create a stable polymer, and the polymer was freeze-dried and compression molded between polydimethylsiloxane (PDMS) coated paper to create the thin film solid adhesive patch; and,
2. α-lipoic acid (L1) monomer in absolute ethanol with a solution of the Gly-OSu derivatized α-lipoic acid (L3) in DMSO.

Experimental:

Adhesive 1 was incubated in PBS at 37° C. for 24 hrs. The mass of the wet solid patch of Adhesive 1 was recorded before and after freeze-drying and had a swelling ratio of 1.1. Adhesive 2 was polymerized in situ in excess PBS and also incubated in the PBS at 37° C. for 24 hrs. The mass of the wet polymer of Adhesive 2 was recorded before and after freeze-drying and had a swelling ratio of 0.3. This is quite favorable over hydrogel adhesives for biomedical applications, as many hydrogel medical adhesives, unfortunately, swell by several hundred percent.

Example 20. Testing the Adhesives for Desirable Biodegradation

Biodegradation of the tissue adhesives is crucial for internal medical applications, and it's desired that toxic degradation products are avoided as thy result in acute inflammation and toxicity. This example is an in vitro study of the biodegradation of the polymers in, or produced by, the adhesives.

Experimental:

Glutathione (GSH)-mediated degradation was used as the model to degrade the poly(α-lipoic acid) polymers, in which the thiolate of the GSH was expected to react with the disulfide bond in the polymer backbone and generate an active thiol group which initiates depolymerization of the polymer. High pressure liquid chromatography was used to verify that the α-lipoic acid monomers (L1) were reformed as desired.

Example 21. Making and Testing a Pressure Sensitive Adhesive (PSA) System from the α-Lipoic Acid Monomer (L1)

This example coats one of the adhesives onto a polyethylene terepthalate (PET) substrate to illustrate use of the adhesives as a pressure sensitive adhesive. Most commonly used PSAs are based on polyacrylates. In addition to being fossil fuel sourced, these polyacrylates have poor recyclability, reusability, and degradability. In sharp contrast, we show that the instant poly(α-lipoic acid) adhesives can potentially be sustainably produced, are biodegradable, and can also be recycled to monomeric feedstock by depolymerization under basic conditions.

Experimental:

The α-lipoic acid (L1) monomer in absolute ethanol was combined with the Gly-OSu-derivatized α-lipoic acid (L3) to form the adhesive for coating onto the PET substrate, a Hostaphan RN36 PET film using a solution coater with a wet thickness of 200 pm to obtain a final coating thickness of 33 g/m². The coated PET was heated at 100° C. for 4 hrs under vacuum. The heat created a stable, sticky viscoelastic polymer, showing that the stabilizer molecules are also effective at high temperatures. By comparison, for example, pure α-lipoic acid treated under similar conditions also forms a sticky polymer, but within 2-3 days becomes a solid crystalline spot indicating depolymerization of the polymer.

Paper coated with polydimethylsiloxane (PDMS) was used as a release paper for the adhesive. The combined result is a PSA system. The system was stored at ambient conditions for testing.

To test performance as a PSA, industry standard static shear tests were performed on the PSA system against stainless steel (SS), high density polyethylene (HDPE), and polytetrafluoroethylene (PTFE) under dry and wet conditions. Static loads are used because PSAs are expected to perform without rupture for a long time while under static stress. Surprisingly, no shear failure was observed over 7 days when the synthesized PSA tapes were applied on SS and HDPE under dry and wet conditions with a 1 kg hanging weight. A similar static shear test of PSA on PTFE showed stable loading of a 500 g load for over 24 hours in dry and over 7 days in wet conditions. Moreover, a separate shear test showed that the PSA tape could hold over 6 kg of weight when applied on SS under dry and wet conditions. Another underwater experiment showed that a sticky note prepared with our PSA can be repositioned at least three times and can bear a 500 gm static load after each repositioning. Moreover, a freshly positioned sticky note with a contact area of 2.5*3 $cm^2$ can hold a 500 gm load over 7 days while submerged under water. These data confirm the attractive adhesion strength of the synthesized PSA under both dry and wet conditions.

Figure 5A:
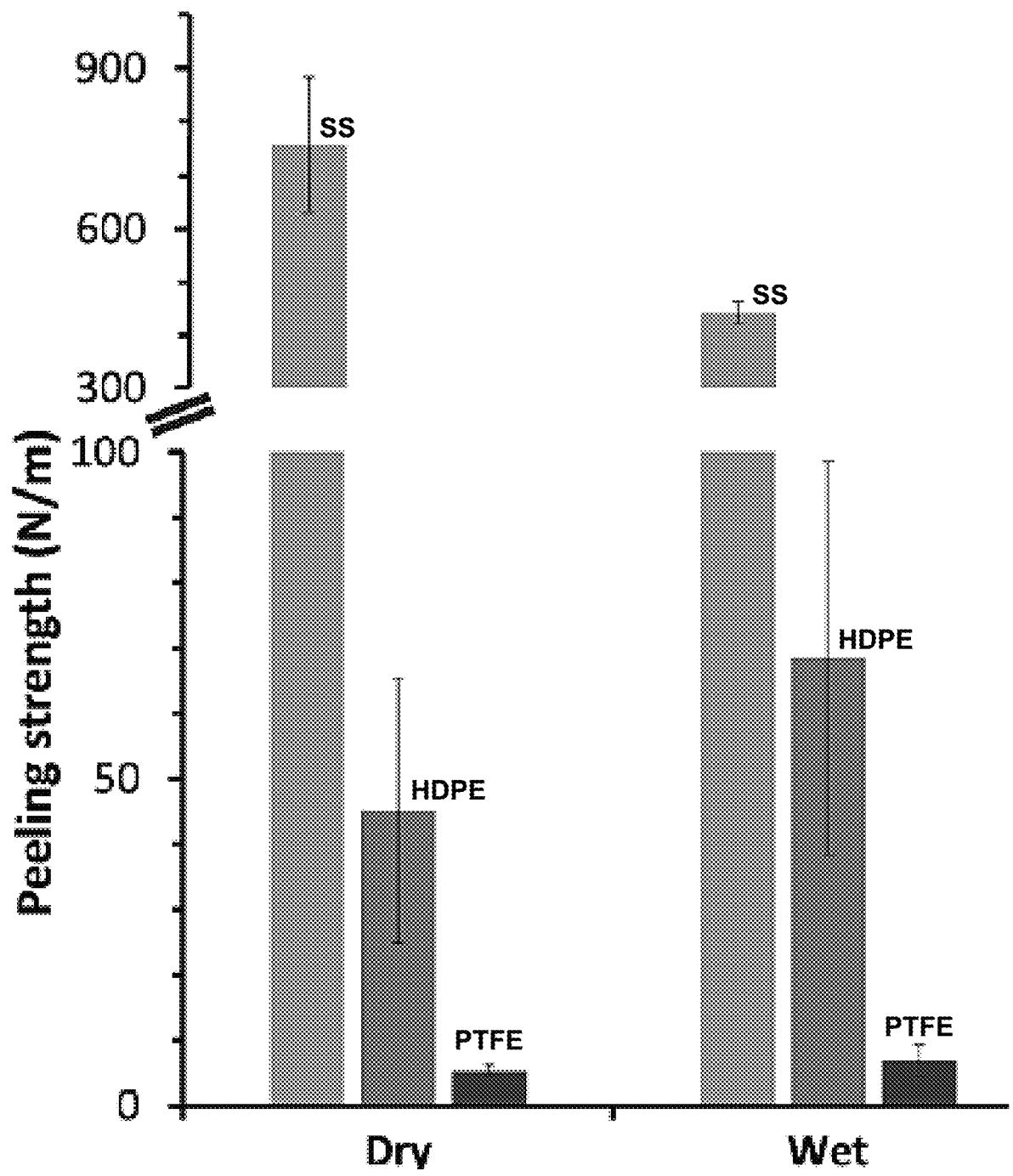

The adhesion strength of the synthesized PSA was also evaluated using a 180° peel test. The dry samples for peeling were prepared by adhering the PSA tape to different substrates, then stored for 24 hours at ambient conditions before measurement. The wet samples were assembled and stored underwater for 24 hours before analysis. The PSA tape achieved peel strength of 760+/−127 N/m, 45+/−20 N/m, and 5+/−0.8 N/m against SS, HDPE, and PTFE, respectively, under dry conditions (see FIG. 5A). Underwater, the peel strength was 441+/−21 N/m on SS, 68+/−30 N/m on HDPE, and 6.9+/−2.4 N/m on PTFE (see FIG. 5A). Although a reduction in peel strength was observed in water for SS, an opposite trend was detected for HDPE and PTFE, indicating excellent underwater adhesion performance of the synthesized PSA. Investigation of the failure mechanism showed cohesive failure in SS, whereas adhesive failure was observed in HDPE and PTFE.

Figure 5C:
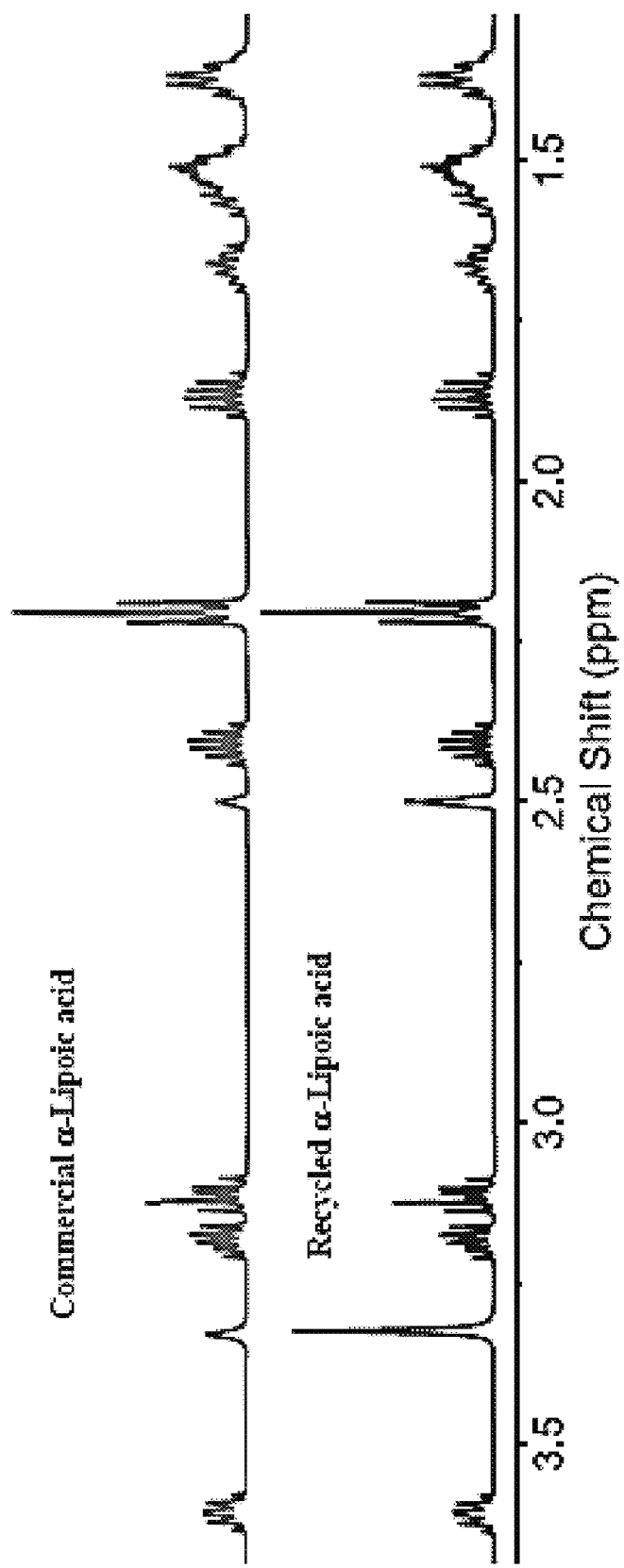
FIG. 5C provides an $^1$H NMR comparison between the chemical spectra of commercial vs. recycled α-lipoic acid, showing the recycling process is successful.

To demonstrate recyclability of the PSA adhesive, the PSA tape was treated with 0.5M NaOH for 2 hours, and the backing PET was removed by filtration (see FIG. 5B). Subsequent acidification of the aqueous solution with 6M HCl leads to α-lipoic acid in solid form with an excellent yield (see FIG. 5B). HPLC and 1H NMR analysis confirmed the high purity of the recycled α-lipoic acid (see FIG. 5C).

Examples 22-25 are Polymers of Poly(Asparagusic Acid) and Methods of Making the Polymers and Products of the Polymers The following examples show that the instant technology provides a poly(asparagusic acid), with and without addition of a stabilizer molecule, that has features that are also desirable, including excellent mechanical properties, adhesion strength, cost-effective production, depolymerization into therapeutic monomers, and closed-loop chemical recycling. This is the first report of a poly(asparagusic acid) at all and, as such, it is also the first report of it's desirable characteristics, features, and uses in the medical field and beyond through poly(asparagusic acid) compositions, methods of making, and products. These examples teach that a poly(asparagusic acid) can be provided as (i) a precursor solution of monomer used to form the poly(asparagusic acid); (ii) a solution of poly(asparagusic acid); (iii) a freeze-dried form of the poly(asparagusic acid) that can be reconstituted as a spray in solution or formed into a solid adhesive product; (iv) a combination of a poly(asparagusic acid) and asparagusic acid monomer in solution; or any combination thereof. It should be appreciated that the terms "macromolecular" and "polymeric" can be used interchangeably in some embodiments.

Example 22. Testing the Stabilizer on a Different Polydisulfide Polymer, Namely Asparagusic Acid This example is comparing the stabilization of a polymer created from the α-lipoic acid (L1) monomer to a novel polymer created from an asparagusic acid monomer (L8). The asparagusic acid monomer (L8) is added to glycine N-hydroxysuccinimide ester (Gly-OSu) to create a stabilizer molecule (L9), an Gly-OSu-derivatized asparagusic acid monomer. The stabilizer is added to an absolute ethanol solution of the asparagusic acid (L8) that includes a catalytic amount of DMSO for a slow polymerization system that shows a successful creation of a stable polymer with the Gly-OSu-derivatized asparagusic acid monomer.

Experimental:

An ethanolic solution of a mixture of asparagusic acid (L8) and a stabilizer (L9) was prepared with a mol ratio L8:L3 of 93:7, and a catalytic amount of DMSO was added to ensure the solubility of the NHS esters. The ethanolic adhesive precursor solution prepared in this manner had a total concentration (L8+L3) of 500 mg/ml. The precursor solution was exposed to water to trigger dithiolane polymerization to obtain a stable sticky solid.

Example 23. Poly(Asparaqusic Acid) Will Self-Polymerize in Absolute Ethanol and is More Stable than Poly(α-Lipoic Acid) in the Absence of a Stabilizer Although a stabilizer is needed in many applications that require a prolonged stability, the poly(asparagusic acid) without the stabilizer is sufficiently stable for some uses. This example shows that
1. asparagusic acid monomer (L8) will self-polymerize, in the absence of water, in absolute ethanol when concentrated to 600 mg/ml, is set-aside at room temperature for 30 minutes, and the solvent is evaporate under vacuum at 45° C. The poly(asparagusic acid) remained stable for at least 24 hours at room temperature before it is used.
2. the poly(asparagusic acid) can be mixed with pure water to increase polymerization, washed 1× with PBS to mimic human body conditions, and freeze-dried before it is used.
3. the asparagusic acid monomer in pure ethanol can be mixed with acid to speed polymer formation, and the poly(asparagusic acid) can then be mixed with pure water to increase polymerization, washed 1× with PBS to mimic human body conditions, and freeze-dried before it is used.

Experimental:

Asparagusic acid (500 mg) was dissolved in pure ethanol at a concentration of 600 mg/mL. The clear solution was left aside for 30 min at room temperature, followed by evaporation of the solvent at reduced pressure at 45° C. to obtain a "macromolecular" precursor. The gel-like precursor was stored at room temperature for at least 24 h before use.

Asparagusic acid (500 mg) was dissolved in pure ethanol at a concentration of 600 mg/mL. The clear solution was left aside for 30 min at room temperature, followed by evaporation of the solvent at reduced pressure at 45° C. to obtain a "macromolecular" precursor. The "macromolecular" precursor was further polymerized by adding milliQ water (3 mL), and obtained solid polymer was washed with 1×PBS (pH 7.4). The polymer was freeze-dried to form a dry solid before use.

Asparagusic acid (500 mg) was dissolved in pure ethanol at a concentration of 600 mg/mL, and 5 mol % HCl (4M in dioxane) was added. The clear solution was left aside for 30 min at room temperature, followed by evaporation of the solvent at reduced pressure at 30° C. to obtain a "macromolecular" precursor. The "macromolecular" precursor was further polymerized by adding milliQ water (3 mL), and obtained solid polymer was washed with milliQ water until the pH of the water became 6. Afterward, the solid polymer was washed with excess 1×PBS (pH 7.4). The polymer was freeze-dried to form a dry solid before use.

It was discovered that, although the asparagusic acid will self-polymerize, it is beneficial to the amount and speed of polymerization to add water and acid to the reaction.

Adhesive Sprays

It was discovered that the above compositions can be formulated as desirable adhesive sprays. Namely, (i) the poly(asparagusic acid) in pure ethanol solution can be diluted 600 mg/ml to 300 mg/ml to form a useful adhesive spray; and (ii) the freeze-dried poly(asparagusic acid), whether or not formed in the acid-catalyzed reaction, can be redissolved into a pure ethanol solution to a concentration of 300 mg/ml to form a useful adhesive spray.

Solid Adhesive Patches

It was also discovered that the above freeze-dried compositions can be (i) molded, (ii) thermally polymerized, or (iii) solution cast, into desirable solid adhesive patches. Namely, the freeze-dried poly(asparagusic acid), whether or not formed in the acid-catalyzed reaction, can be used to form a solid adhesive patch by (i) compression molding at 75° C. for 15 min between PDMS backing paper to obtain a homogeneous thin film (thickness 250±50 pm); (ii) thermal polymerization by dissolving the freeze-dried polymer in pure ethanol to a concentration of 600 mg/ml, pouring the solution into a PDMS mold, and heating for 3 hours at 80° C. to form the solid adhesive patch; or, (iii) solution cast by dissolving the freeze-dried polymer in pure ethanol to a concentration of 400 mg/mL. pouring the solution into a PDMS mold, and evaporating the solution away at ambient temperature to form the solid adhesive patch. The solvent was evaporated at ambient temperature to obtain an adhesive patch. The solid adhesive patches were rested overnight before further use.

Pure ethanol was the solvent of choice for these experiments. However, the skilled artisan will appreciate that any suitable solvent for the poly(asparagusic acid) can be used for the sprays and the patches. Suitable solvents for example, can be selected from the group consisting of ethanol, methanol, water, DMSO, any combination thereof, and the like.

Example 24. Testing Adhesion Between Biological Tissues Using Poly(Asparaqusic Acid) as a Replacement for Medical Grade Cyanoacrylate Superglues Dry solid poly(asparagusic acid) can be created using the methods taught herein. The freeze-dried solid poly(asparagusic acid), whether or not produced from an acid-catalyzed reaction, can be used to adhere animal tissue together. In this example, the freeze-dried poly(asparagusic acid) from the acid-catalyzed reaction method was dissolved in pure ethanol, an adhesive spray was created, and the spray was used to adhere two pieces of bovine pericardium tissue. After incubation in PBS at 37° C. for 2 minutes and 24 hours, it was discovered that the strength of adhesion was twice as strong after 24 hours.

Experimental:

The dry solid polymer obtained from acid-catalyzed polymerization of asparagusic acid was dissolved in pure ethanol at a concentration of 300 mg/mL. The liquid precursor was sprayed on two pieces of bovine pericardium tissue surfaces (40 μL in 1 cm$^2$), and the two pieces were immediately brought into contact. After forming the lap joints, they were incubated for 2 minutes in PBS at 37° C. The lap shear strength after 2 minutes on wet bovine pericardium tissue was 121±21 kPa. Interestingly, when the lap joints were incubated for 24 hours in PBS at 37° C., the shear strength increased to 150±8 kPa. A mixed failure (both cohesive and adhesive failure) was observed in 5 repetitions, and adhesive failure were observed after 2 minutes and 24 h of incubation, respectively. A "cohesive failure" means the adhesive stays attached to both sides of the lap joints after breaking the joints, such that the rupture occurs in the adhesive itself, leaving the interface between the substrate and the adhesive intact. An "adhesive failure" means the adhesive stays attached only on one side of the joint after breaking the joints, such that the bond fails between the adhesive and the substrate upon which the adhesive is attached. A "mixed failure" means that the bond breaks in the adhesive itself in some places and where the adhesive bonds to the substrate in other places.

Example 25. Making a Pressure Sensitive Adhesive (PSA) System from the Asparagusic Acid Monomer (L8)

This example coats a poly(asparagusic acid) adhesive onto a polyethylene terepthalate (PET) substrate to illustrate use of the adhesive as a pressure sensitive adhesive. Most commonly used PSAs are based on polyacrylates. In addition to being fossil fuel sourced, these polyacrylates have poor recyclability, reusability, and degradability. In sharp contrast, we the instant poly(asparagusic acid) adhesives can potentially be sustainably produced with or without stabilizer for this application, are biodegradable, and can also be recycled to monomeric feedstock by depolymerization under basic conditions.

Experimental:

Asparagusic acid (500 mg) was dissolved in pure ethanol at a concentration of 600 mg/mL. The clear solution was left aside for 30 min at room temperature, followed by evaporation of the solvent at reduced pressure at 45° C. to obtain a gel-like precursor. No stabilizer was added. The gel-like precursor was stored at room temperature for at least 24 h before use. Afterwards, gel-like precursor was diluted with pure ethanol to obtained a concentration of 300 mg/mL. The obtained homogeneous precursor solution was coated onto Hostaphan RN36 PET films using a solution coater with a wet thickness of 200 pm to obtain a final coating thickness of 15 g/m$^2$. Then the monomer mixture-coated PET was heated to 80° C. for 3 hours to obtain PET tape coated with PSA. PDMS release paper was applied on the top of the adhesive layer to protect the adhesive layer as a PSA system temporarily and, finally, the PSA system was stored at ambient conditions for later use.

Examples 26-35 are Free-Flowing Solids of the Polymers and Methods of Making the Polymers and Products of the Free-Flowing Solids of the Polymers Above, we taught how the polydisulfide polymers taught herein can be presented in liquid form as precursors to the formation of sticky polymers, either as solutions of monomers, solutions of macromolecules, or combinations thereof. We also showed how to produce spray adhesive products of the liquid forms, and freeze-dried solids of the liquid forms, as well as solid adhesive products that may or may not include a liquid adhesive coating added to the solid adhesive product. The following examples show how to make free-flowing solid products, such as powders, and how to make products directly from the free-flowing form.

Example 26. Making and drying a stabilized form of poly(α-lipoic acid) in aqueous solution from coniugate base monomer sodium lipoate (L4), the stabilizer being the Gly-OSu-derivatized α-lipoic acid (L3)

This example shows that a poly(α-lipoic acid) can be stabilized and dried to create a purified powder of the sticky polymer.
Experimental:
Sodium lipoate (L4) was dissolved in miliQ at 400 mg/mL, and OSu-derivatized α-lipoic acid (L3) was added with a mol ratio L4:L3 of 90:10. The mixture was stirred overnight before precipitating into ethanol. The solid polymer was freeze-dried to obtain purified "macromolecular" sodium lipoate.

Example 27. Making a Stabilized Form of Poly(α-Lipoic Acid) in Pure Ethanol Solution with DMSO Using α-Lipoic Acid (L1) as the Monomer, the Stabilizer being the Gly-OSu-Derivatized α-Lipoic Acid (L3)

Experimental:
A pure ethanol solution of a mixture of α-lipoic acid (L1) and glycine N-hydroxysuccinimide ester of lipoic acid (L3) was prepared at a mol ratio of 93:7, and a catalytic amount of DMSO was added to aid in the polymerization and create an ethanolic adhesive precursor solution with a total monomer concentration of 400 mg/ml and a gelation time of 30 minutes. The solid polymer was dried to obtain purified "macromolecular" poly(α-lipoic acid).

Example 28. Making a Stabilized Form of Poly(α-Lipoic Acid) from α-Lipoic Acid, Calcium Lipoate, and NHS-Derivatized-α-Lipoic Acid (L2), and Converting the Poly(α-Lipoic Acid) into a Powder Adhesive for Thermal Polymerization into a Solid Adhesive Product This example shows that ambient moisture and compression temperature and pressure facilitate the formation of the poly (α-lipoic acid) as a homogeneous solid adhesive product.
Experimental:
A mixture of α-lipoic acid (L1), the conjugate base calcium lipoate, and NHS-derivatized-α-lipoic acid (L2) was prepared at a mol ratio of 75:19:6, was ground together in a porcelain mortar to obtain a homogeneous powder. The powder was used to prepare lap joints and thin film preparation. The thin film was obtained by compression molding the powder mixture at 100° C., 2000 psi for 10 min. Without intending to be bound by any theory or mechanism of action, it is believed that the ambient moisture and compression temperature and pressure facilitate the formation of the poly (α-lipoic acid) as a homogeneous solid adhesive product, which is the solid adhesive patch.

Example 29. Making a Solid Adhesive Patch of Poly(α-Lipoic Acid) Using a Thermal Polymerization of α-Lipoic Acid, Sodium Lipoate, and NHS-Derivatized-α-Lipoic Acid (L2)

This example shows that a mixture of dry α-lipoic acid (L1), dry conjugate base monomer sodium lipoate (L4), and dry NHS-derivatized-α-lipoic acid (L2) can form a solid adhesive product from thermal polymerization faster, and at a lower temperature, than in the prior example.
Experimental:
A mixture of dry α-lipoic acid (L1), dry conjugate base monomer sodium lipoate (L4), and dry NHS-derivatized-α-lipoic acid (L2) at a mol ratio of 52:42:6 was ground together to obtain a sticky solid that was compression molded at 55° C. and 2000 psi for 5 min. A homogeneous solid, adhesive product, which is the solid adhesive patch. Notably, this product was polymerized in nearly half the temperature and half the time of the compressed product made in the prior example.

Example 30. Making a Free-Flowing Powder Adhesive of Poly(α-Lipoic Acid) from a Mixture of Dry α-Lipoic Acid (L1), Dry Conjugate Base Monomer Sodium Lipoate (L4), and Dry NHS-Derivatized-α-Lipoic Acid (L2)

This example shows that a free-flowing powder of monomer, conjugate base of the monomer, and a stabilizer made from the monomer polymerizes quickly in when placed in contact with a wet surface,
Experimental:
A mixture of dry α-lipoic acid (L1), dry conjugate base monomer sodium lipoate (L4), and dry NHS-derivatized-α-lipoic acid (L2) at a ratio of 45:45:10 were ground separately and together into a homogeneously mixed, free-flowing powder. The free-flowing powder polymerized quickly to poly(α-lipoic acid) when applied to a wet surface.

Example 31. A Stable Aqueous Solution of Macromolecular Precursor that can be Activated with an Acidic Activator to Induce Fast Polymerization into a Solid Adhesive Composition of Poly(α-Lipoic Acid)

This example shows that a polymerization in aqueous solution can occur faster with an acidic activator. It should be appreciated that water-based precursors may be more easily implemented, in some embodiments, than pure ethanol solutions.
Experimental:
Macromolecular sodium lipoate (L4) was prepared as described herein and dissolved in milliQ at 200 mg/mL. Separately, 33 mol % citric acid was dissolved in milliQ at a concentration of 400 mg/mL. The macromolecular sodium lipoate (L4) forms a sticky elastic solid once mixed with a citric acid solution as an activator.

In another experiment, macromolecular sodium lipoate (L4) was prepared as described herein and dissolved in milliQ at 200 mg/mL. Separately, 90 mol % ascorbic acid was dissolved in milliQ at a concentration of 400 mg/mL. The macromolecular sodium lipoate (L4) forms a sticky elastic solid once mixed with an ascorbic acid solution as an activator.

Example 32. A Stable, Dry and Free-Flowing Solid Adhesive Composition Including Mixture of Dry Monomers and Dry Stabilizers, and Including a Dry Acidic Activator The free-flowing solid polymerizes quickly into a solid adhesive composition of poly(α-lipoic acid) upon contact with a wet surface. It should be appreciated that stable, dry precursors may be more easily implemented, in some embodiments, than solutions.

Experimental:

A blend of (i) a dry monomeric sodium lipoate (L4) and (ii) a dry NHS-derivatized-α-lipoic acid (L2) were ground into a fine powder at a ratio of 90:10, and then homogeneously mixed with (iii) 33 mol % fine citric acid powder. The result is a dry and free-flowing, stable monomeric precursor that is stored in an air-tight vial for use as a free-flowing powder adhesive. The free-flowing powder polymerized quickly to poly(α-lipoic acid) when applied to a wet surface.

Example 33. A Stable, Dry and Free-Flowing Solid Hemostat and Adhesive Composition that Includes a Mixture of Dry Monomeric α-Lipoic Acid (L1), and a Dry Stabilizer of α-Lipoic Acid (L2) and Macromolcular Sodium Lipoate (L4)

The free-flowing solid polymerizes quickly into a solid adhesive composition of poly(α-lipoic acid) upon contact with a wet surface. It should be appreciated that stable, dry precursors may be more easily implemented, in some embodiments, than solutions.

Experimental:

Macromolecular sodium lipoate (L4) was prepared as described herein and ground into fine dry powder. Then, the powder macromolecular sodium lipoate (L4) powder was mixed with dry lipoic acid monomer (L1) and a dry NHS-derivatized-α-lipoic acid (L2) at a mol ratio of (45:45:10) as a free-flowing solid adhesive and stored in a moisture-free environment. The free-flowing solid adheisive polymerized into a sticky solid when exposed to a wet environment. Moreover, over 100 wt % water absorption was observed, indicating that the free-flowing solid will function well as a hemostat in addition to an adhesive.

Example 34. Mixing Dry Poly(α-Lipoic Acid) with a Polylysine, which can Add an Antimicrobial Activity, Improve Cell Adherence, and Facilitate Delivery of a Negatively Therapeutic Active Agent by Attaching to the Positive Charges on the Polylysine In this example, a dry ε-polylysine, aka poly(ε-lysine), was added to dry poly(sodium lipoate) to form a homogeneous, free-flowing adhesive powder having the properties added by the ε-polylysine.

Experimental:

Macromolecular sodium lipoate (L4) was prepared as described herein and ground into fine dry powder. Separately, the poly(ε-lysine) was grounded into a fine powder and mixed with the macromolecular sodium lipoate (L4) with a 1:1 weight ratio. The obtained powder mixture forms a sticky polymer when exposed to a wet environment, such as a contact with a wet surface.

In another experiment, the macromolecular sodium lipoate (L4) was again prepared as described herein and dissolved in milliQ at a concentration of 200 mg/mL to form a macromolecular sodium lipoate (L4) solution. Separately, ε-polylysine, aka poly(ε-lysine), was dissolved in milliQ to form a poly(ε-lysine) solution, and the pH of the poly(ε-lysine) solution was adjusted to 7.2 with a 1M NaOH solution. Then, the macromolecular sodium lipoate (L4) solution was mixed with the poly(epsilon-lysine) solution at a 1:1 weight ratio to obtain a sticky elastic solid. The sticky elastic solid was freeze-dried and ground to obtain free-flowing powder for use as a free-flowing powder adhesive having the functionality added by the poly(ε-lysine).

Example 35. Testing the Adhesive Strength of a Free-Flowing Powder Adhesive Made from a Dry α-Lipoic Acid Monomer (L1), a Dry Calcium Lipoate Monomer, and a Dry NHS-Derivatized-α-Lipoic Acid Monomer (L2)

Experimental:

20 mg of a mixture of α-lipoic acid monomer (L1), a dry calcium lipoate monomer, and a dry NHS-derivatized-α-lipoic acid monomer (L2) powder was applied as a single strip on one surface of a first aluminum bar for an overlap area of 1×1 cm to create an adhesive-containing strip, and a lap joint was formed by hand-pressing the adhesive-containing strip with an adhesive-free strip on a second aluminum bar. The lap joint was held together with pressure applied from two mini binder clips (available from Office Depot). The lap joint was cured at 100° C. for 10 min and rested 24 hours before being subjected to a lap shear tensile test at a rate of 50 mm/min until failure.

The Adhesive Strength was Strong and Maintained Between Dry and Wet Conditions.

The lap shear strength of the bond formed between the aluminum bars bonded by the powder adhesive was surprisingly high (10.5±7 MPa). The adhesive strength realized no significant change (10.1±1.9 MPa), even after submerging in water for 24 h.

The Adhesive Strength was Repeatable on Several Tested Substrates.

This method was repeated on different substrates, including SS (dry 6.1±2.3 MPa; wet 7.6±2.4 MPa), wood (dry 6.1±0.5 MPa; wet 2±0.15 MPa), and PTFE (dry 0.57±0.14 MPa; wet 0.56±0.03 MPa), all of which maintained excellent adhesion strength in both dry and wet conditions.

Any Ruptured Joint could be Easily Re-Established by Rejoining and Reheating, and the Strength was Maintained Over Several Cycles of Rupture, Rejoining, and Reheating.

Moreover, we observed another surprising and unexpected result: lap shear joints were ruptured intentionally and found to be easily rejoined by reheating at 100° C. for 10 min. After the rupture and rejoining, there was no significant reduction in strength from the original measurements, and this was repeated and observed over 5 cycles of rupturing and rejoining. As an alternative to powders, the solid adhesive patches formed as thin films of thermally polymerized structural adhesive were made from the powder mixture and showed comparable adhesion strength to powder in both dry and wet conditions.

We claim:
1. An adhesive composition, comprising
   a plurality of substituted 1,2-dithiolane monomers, the substituted 1,2-dithiolane monomers functional to polymerize through a ring-opening reaction to form a polydisulfide polymer having
   a first active thiol end and a second active thiol end; and, a plurality of repeating units having a substituted dithioalkyl structure from the ring opening reaction as follows

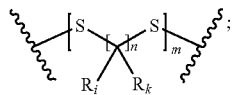

wherein, n is 3;

each $R_i$ and $R_k$ is independently selected from the group consisting of H; alkyl, cycloalkyl, alkenyl, alkynyl, and aryl groups, each of the groups having from 1-8 carbons; hydroxylated alkyl, cycloalkyl, alkenyl, alkynyl, and aryl groups, each of the groups having from 1-8 carbons; and, carboxylated alkyl, cycloalkyl, alkenyl, alkynyl, and aryl groups, each of the groups having from 1-8 carbons; wherein, i and k are integers, and at least one $R_i$ or $R_k$ in each repeating unit includes a carbonyl functionality;

and, m is an integer selected to match a desired molecular weight of the polymer;

and, a plurality of stabilizer molecules configured to stabilize the first active thiol end of the polymer, the plurality of stabilizer molecules being the substituted cyclic disulfide molecules derivatized to include a functional group that forms a first labile bond with the first active thiol end, the first labile bond selected from the group consisting of a thioester bond, a thiocarbamate bond, and a thioether bond;

wherein, the repeating units and the stabilizer molecules are the same, or substantially the same, chemical moieties following a depolymerization of the polymer.

2. The adhesive composition of claim 1, further including a plurality of terminator molecules for forming a labile bond with the second active thiol group, the plurality of terminator molecules selected from the group consisting of R'OH, R'CO$_2$H, and R'SH, and R' is selected from the group consisting of alkyl, cycloalkyl, alkenyl, cycloalkenyl, alkynyl, cycloalkynyl, and aryl groups, each of the groups having from 1-8 carbons; and, the second labile bond is selected from the group consisting of thioethers, thioesters, and disulfides.

3. The adhesive composition of claim 1, further including a plurality of terminator molecules for forming a labile bond with the second active thiol group, the plurality of terminator molecules selected from the group consisting of alkanols having from 1-8 carbons, alkanoic acids having from 1-8 carbons, and alkylthiols having from 1-8 carbons, and the second labile bond is selected from the group consisting of thioethers, thioesters, and disulfides.

4. The adhesive composition of claim 1, further including a plurality of terminator molecules for forming a labile bond with the second active thiol group, the plurality of terminator molecules selected from the group consisting of ethanol, and a substituted 1,2-dithiolane with a hydroxyl functionality.

5. The adhesive composition of claim 1, wherein:
the repeating unit is a substituted 1,3-dithiopropyl structure as follows

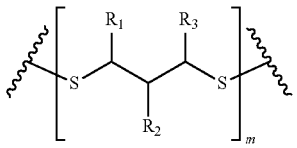

wherein, m is an integer;

$R_i$ includes $R_1$, $R_2$, and $R_3$; and, each $R_k$ is H;

and, each stabilizer molecule includes the substituted 1,3-dithiopropyl structure.

6. The adhesive composition of claim 5, wherein:
the repeating unit is a substituted 1,3-dithiopropyl structure as follows

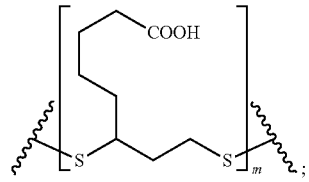

wherein, m is an integer;

$R_1$ is a pentanoic acid group, and $R_2$ and $R_3$ are each H;

and, each stabilizer molecule includes the substituted 1,3-dithiopropyl structure, wherein $R_1$ is a pentanoic acid group, and $R_2$ and $R_3$ are each H.

7. The adhesive composition of claim 5, further including a plurality of terminator molecules selected from the group consisting of ethanol and a substituted 1,2-dithiolane with a hydroxyl functionality, the terminator molecules functioning to form a second labile bond with the second active thiol end of the polymer to further stabilize the polymer.

8. The adhesive composition of claim 5, wherein:
the repeating unit has a substituted 1,3-dithiopropyl structure

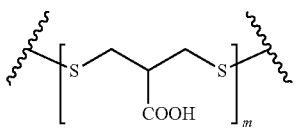

wherein, m is an integer;

$R_1$ and $R_3$ are H, and $R_2$ is a carboxylic acid group;

and, each stabilizer molecule includes the substituted 1,3-dithiopropyl structure, wherein $R_1$ and $R_3$ are H and $R_2$ is a carboxylic acid group.

9. A stabilized and recyclable polydisulfide polymer, comprising:

a plurality of substituted 1,2-dithiolane monomers, the substituted 1,2-dithiolane monomers functional to polymerize through a ring-opening reaction to form a polydisulfide polymer having
a first active thiol end and a second active thiol end; and,
a plurality of repeating units having a substituted dithioalkyl structure from the ring opening reaction as follows

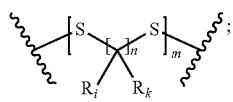

wherein,
n is 3;
each $R_i$ and $R_k$ is independently selected from the group consisting of H; alkyl, cycloalkyl, alkenyl, alkynyl, and aryl groups, each of the groups having from 1-8 carbons; hydroxylated alkyl, cycloalkyl, alkenyl, alkynyl, and aryl groups, each of the groups having from 1-8 carbons; and, carboxylated alkyl, cycloalkyl, alkenyl, alkynyl, and aryl groups, each of the groups having from 1-8 carbons; wherein, i and k are integers, and at least one $R_i$ or $R_k$ in each repeating unit includes a carbonyl functionality;
and,
m is an integer selected to match a desired molecular weight of the polymer;
and,
a plurality of stabilizer molecules configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioester bond;
wherein, the repeating units and the stabilizer molecules are the same, or substantially the same, chemical moieties following a degradation of the polymer during a recycling of the polymer.

10. The stabilized and recyclable polydisulfide polymer of claim 9, further including a plurality of terminator molecules for forming a labile bond with the second active thiol group, the plurality of terminator molecules selected from the group consisting of R'OH, R'CO$_2$H, and R'SH, and R' is selected from the group consisting of alkyl, cycloalkyl, alkenyl, cycloalkenyl, alkynyl, cycloalkynyl, and aryl groups, each of the groups having from 1-8 carbons; and, the second labile bond is selected from the group consisting of thioethers, thioesters, and disulfides.

11. The stabilized and recyclable polydisulfide polymer of claim 9, further including a plurality of terminator molecules for forming a labile bond with the second active thiol group, the plurality of terminator molecules selected from the group consisting of alkanols having from 1-8 carbons, alkanoic acids having from 1-8 carbons, and alkylthiols having from 1-8 carbons, the second labile bond selected from the group consisting of thioethers, thioesters, and disulfides.

12. The stabilized and recyclable polydisulfide polymer of claim 9, further including a plurality of terminator molecules for forming a labile bond with the second active thiol group, the plurality of terminator molecules selected from the group consisting of ethanol and a substituted 1,2-dithiolane with a hydroxyl functionality, the terminator molecules functioning to form a second labile bond with the second active thiol end of the polymer to further stabilize the polymer.

13. The stabilized and recyclable polydisulfide polymer of claim 9, wherein:
the dithioalkyl repeating unit is a substituted 1,3-dithiopropyl structure as follows

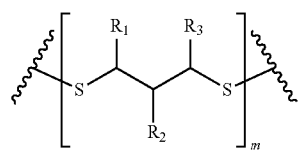

wherein,
$R_i$ includes $R_1$, $R_2$, and $R_3$; and,
each $R_k$ is H; and,
m is an integer selected to match a desired molecular weight of the polymer;
and,
each stabilizer group in the plurality of stabilizer groups includes the substituted 1,3-dithiopropyl structure.

14. The stabilized and recyclable polydisulfide polymer of claim 13, wherein:
the repeating unit is a substituted 1,3-dithiopropyl structure as follows

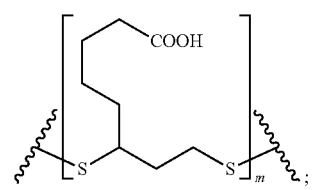

wherein,
m is an integer selected to match a desired molecular weight of the polymer; and,
$R_1$ is a pentanoic acid group, and $R_2$ and $R_3$ are each H;
and,
each of the stabilizer groups includes the 1,3-dithiopropyl structure in which $R_1$ is a pentanoic acid group, and $R_2$ and $R_3$ are each H.

15. The stabilized and recyclable polydisulfide polymer of claim 13, wherein:
the repeating unit is a substituted 1,3-dithiopropyl structure as follows

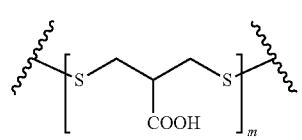

wherein,
m is an integer selected to match a desired molecular weight of the polymer;
$R_1$ and $R_3$ are H, and $R_2$ is a carboxylic acid group;
and,
each of the stabilizer groups includes the 1,3-dithiopropyl repeating unit in which $R_1$ and $R_3$ are H, and $R_2$ is a carboxylic acid group.

16. A method of making an adhesive composition, comprising obtaining a plurality of substituted dithiolane monomers, the substituted dithiolane monomers functional to polymerize through a ring-opening reaction to form a polydisulfide polymer having
a first active thiol end and a second active thiol end; and,
a plurality of repeating units having a substituted dithioalkyl structure from the ring opening reaction as follows

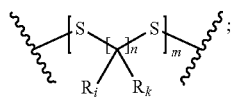

wherein,
n is 3;
each $R_i$ and $R_k$ is independently selected from the group consisting of H; alkyl, cycloalkyl, alkenyl, alkynyl, and aryl groups, each of the groups having from 1-8 carbons; hydroxylated alkyl, cycloalkyl, alkenyl, alkynyl, and aryl groups, each of the groups having from 1-8 carbons; and, carboxylated alkyl, cycloalkyl, alkenyl, alkynyl, and aryl groups, each of the groups having from 1-8 carbons; wherein, i and k are integers, and at least one $R_i$ or $R_k$ in each repeating unit includes a carbonyl functionality;
and,
m is an integer selected to match a desired molecular weight of the polymer;
obtaining a plurality of stabilizer molecules configured to stabilize the first active thiol end of the polymer, the plurality of stabilizer molecules being the substituted cyclic disulfide molecules derivatized to include a functional group that forms a first labile bond with the first active end, the first labile bond selected from the group consisting of a thioester bond, a thiocarbamate bond, and a thioether bond;
polymerizing the plurality of the substituted cyclic disulfide molecules to create the polymer; and,
stabilizing the polymer by reacting the plurality of stabilizer molecules with the first active end;
wherein, the repeating units and the stabilizer molecules are the same, or substantially the same, chemical moieties following a degradation of the polymer during a recycling of the polymer.

17. The method of claim 16, wherein the polymerizing includes reacting the monomers in a solvent selected from the group consisting of polar protic solvent, a polar aprotic solvent, pure ethanol, an aqueous reaction solvent including water, ethanol, DMSO, and combinations thereof.

18. The method of claim 16, further comprising
stabilizing the polymer by reacting a plurality of terminator molecules for forming a labile bond with the second active thiol group, the plurality of terminator molecules selected from the group consisting of R'OH, R'CO$_2$H, and R'SH, and R' is selected from the group consisting of alkyl, cycloalkyl, alkenyl, cycloalkenyl, alkynyl, cycloalkynyl, and aryl groups, each of the groups having from 1-8 carbons; and, the second labile bond is selected from the group consisting of thioethers, thioesters, and disulfides.

19. The method of claim 16, further comprising
stabilizing the polymer by reacting a plurality of terminator molecules for forming a labile bond with the second active thiol group, the plurality of terminator molecules selected from the group consisting of selected from the group consisting of alkanols having from 1-8 carbons, alkanoic acids having from 1-8 carbons, and alkylthiols having from 1-8 carbons, the second labile bond selected from the group consisting of thioethers, thioesters, and disulfides.

20. The method of claim 16, further comprising
stabilizing the polymer by reacting a plurality of terminator molecules for forming a labile bond with the second active thiol group, the plurality of terminator molecules selected from the group consisting of ethanol and a substituted 1,2-dithiolane with a hydroxyl functionality, the terminator molecules functioning to form a second labile bond with the second active thiol end of the polymer to further stabilize the polymer.

21. A method of using the adhesive composition of claim 1 as a non-medical adhesive, comprising adhering a non-medical material to a substrate using the adhesive composition.

22. A method of using the adhesive composition of claim 1 as a medical tissue adhesive in a method of treatment of a subject, comprising adhering a biological tissue to a substrate using the adhesive composition.

* * * * *